US009783820B2

(12) United States Patent
Cong et al.

(10) Patent No.: US 9,783,820 B2
(45) Date of Patent: Oct. 10, 2017

(54) METHODS AND COMPOSITIONS TO ENHANCE ACTIVITY OF CRY ENDOTOXINS

(71) Applicant: PIONEER HI BRED INTERNATIONAL INC, Johnston, IA (US)

(72) Inventors: Ruth Cong, Palo Alto, CA (US); Takashi Yamamoto, Dublin, CA (US); Yi Zheng, Palo Alto, CA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 14/435,381

(22) PCT Filed: Oct. 14, 2013

(86) PCT No.: PCT/US2013/064784

§ 371 (c)(1),
(2) Date: Apr. 13, 2015

(87) PCT Pub. No.: WO2014/062544

PCT Pub. Date: Apr. 24, 2014

(65) Prior Publication Data

US 2015/0232877 A1 Aug. 20, 2015

Related U.S. Application Data

(60) Provisional application No. 61/713,844, filed on Oct. 15, 2012.

(51) Int. Cl.
*C07K 14/325* (2006.01)
*C12N 15/82* (2006.01)
*C07K 14/245* (2006.01)

(52) U.S. Cl.
CPC ........ *C12N 15/8286* (2013.01); *C07K 14/245* (2013.01); *C07K 14/325* (2013.01); *C07K 2319/35* (2013.01); *C07K 2319/55* (2013.01)

(58) Field of Classification Search
None
See application file for complete search history.

(56) References Cited

U.S. PATENT DOCUMENTS 9,109,231 B2 * 8/2015 Bermudez ............ C07K 14/325
2011/0223686 A1 9/2011 Sakai et al.

FOREIGN PATENT DOCUMENTS

WO 2008121633 A1 9/2008
WO 2012135436 A1 4/2012
WO 2012109515 A1 8/2012

OTHER PUBLICATIONS

Pardo-Lopez et al. Peptides (2009) 30, pp. 589-595.*
Griko et al. Biochemistry (2007), vol. 46, pp. 10001-10007.*
Hire, R.S. et al; "Expression, purification and characterization of the Cry2Aa14 toxin from *Bacillus thuringiensis* subsp. *kenyae*", Toxicon, vol. 54, No. 4 ; pp. 519-524 (2009).
Vazquez-Padron, R.I. et al; "Cryptic endotoxic nature of Bacillus thuringiensis Cry1Ab insecticidal crystal protein", FEBS Letters, vol. 570, No. 1-3, pp. 30-36 (2004).
Sachdev, D. et al; "Solubility of Proteins Isolated from Inclusion Bodies is Enhanced by Fusion to Maltose-Binding Protein or Thioredoxin", Protein Expression and Purification Academic Press; vol. 12, No. 1, pp. 122-132 (1998).
International Search Report and Written Opinion for International Application No. PCT/US2013/064784 completed Aug. 4, 2014.

* cited by examiner

*Primary Examiner* — Medina A Ibrahim
(74) *Attorney, Agent, or Firm* — Pioneer Hi-Bred Int'l

(57) ABSTRACT

Methods and compositions for enhancing the resistance of plants to plant pests are provided. Chimeric pesticidal polypeptides and nucleic acid molecules encoding the chimeric pesticidal polypeptides are provided. The chimeric pesticidal polypeptides comprising a solubility-enhancing polypeptide operably linked to a polypeptide comprising pesticidal activity. The nucleic acid molecules can be used in expression cassettes for making transformed plants with enhanced resistance to plant pests. Further provided are transformed plants, plant tissues, plant cells, other host cells, and seeds as well as pesticidal compositions.

3 Claims, 1 Drawing Sheet

*E. coli* MBP-BT Cry protein fusion

SEQUENCE LISTING

```
<160> NUMBER OF SEQ ID NOS: 36

<210> SEQ ID NO 1
<211> LENGTH: 3093
<212> TYPE: DNA
<213> ORGANISM: Artificial Sequence
<220> FEATURE:
<223> OTHER INFORMATION: MBP-SA-IP3-1
<220> FEATURE:
<221> NAME/KEY: misc_feature
<222> LOCATION: (1)...(1104)
<223> OTHER INFORMATION: MBP
<220> FEATURE:
<221> NAME/KEY: misc_feature
<222> LOCATION: (1105)...(1161)
<223> OTHER INFORMATION: Linker
<220> FEATURE:
<221> NAME/KEY: misc_feature
<222> LOCATION: (1162)...(3093)
<223> OTHER INFORMATION: IP3-1

<400> SEQUENCE: 1

atggacaaaa tcgaagaagg taaactggta atctggatta acggcgataa aggctataac      60

ggtctcgctg aagtcggtaa gaaattcgag aaagataccg gaattaaagt caccgttgag     120

catccggata aactggaaga gaaattccca caggttgcgg caactggcga tggccctgac     180

attatcttct gggcacacga ccgctttggt ggctacgctc aatctggcct gttggctgaa     240

atcaccccgg acaaagcgtt ccaggacaag ctgtatccgt ttacctggga tgccgtacgt     300

tacaacggca agctgattgc ttacccgatc gctgttgaag cgttatcgct gatttataac     360

aaagatctgc tgccgaaccc gccaaaaacc tgggaagaga tcccggcgct ggataaagaa     420

ctgaaagcga aaggtaagag cgcgctgatg ttcaacctgc aagaaccgta cttcacctgg     480

ccgctgattg ctgctgacgg gggttatgcg ttcaagtatg aaaacggcaa gtacgacatt     540

aaagacgtgg gcgtggataa cgctggcgcg aaagcgggtc tgaccttcct ggttgacctg     600

attaaaaaca aacacatgaa tgcagacacc gattactcca tcgcagaagc tgcctttaat     660

aaaggcgaaa cagcgatgac catcaacggc ccgtgggcat ggtccaacat cgacaccagc     720
```

```
aaagtgaatt atggtgtaac ggtactgccg accttcaagg gtcaaccatc caaaccgttc    780
gttggcgtgc tgagcgcagg tattaacgcc gccagtccga acaaagagct ggcaaaagag    840
ttcctcgaaa actatctgct gactgatgaa ggtctggaag cggttaataa agacaaaccg    900
ctgggtgccg tagcgctgaa gtcttacgag gaagagttgg cgaaagatcc acgtattgcc    960
gccactatgg aaaacgccca gaaaggtgaa atcatgccga acatcccgca gatgtccgct   1020
ttctggtatg ccgtgcgtac tgcggtgatc aacgccgcca gcggtcgtca gactgtcgat   1080
gaagccctga aagacgcgca gactcgtatc accaagagca tgtctgcatc tgcatctgca   1140
tctgcatctg catctgcacg catgaaccct aacaacaggt cagagcacga cacgatcaag   1200
acaaccgaga acaacgaggt gccgacgaac cacgtccagt acccactcgc cgaaacaccg   1260
aaccctaccc tggaggacct caactacaag gagttcctga ggatgacagc ggacaacaac   1320
accgaagccc tcgactctag cacgaccaag gacgtgattc agaagggcat ctctgtggtc   1380
ggcgacctgc ttggcgttgt cgggttcccg ttcggcggcg ctctcgtcag cttctacacg   1440
aacttcttga acaccatctg gccgtccgaa gacccccctca aggcgttcat ggagcaggtg   1500
gaggccctca tcgaccagaa gatcgctgac tatgccaaga acaaggctct ggcggagctg   1560
caaggcctgc agaacaactt cgaggactat gtgagcgccc tcagctcttg gcagaagaac   1620
ccagtcagct cccgcaaccc gcacagccag ggccgcatca gggagctgtt cagccaggcc   1680
gagagccact tccgcaactc catgccgagc ttcgccgtga gcggctacga ggtcctcttc   1740
ctgactacct atgcccaggc tgccaacacc cacttgcttc tcctgaagga cgcccagatc   1800
tacggcgaag agtggggcta cgagaaggag gacatcgccg agttctacca caggcagctc   1860
aagctgacgc aggagtacac cgaccactgc gtgaagtggt acaacgtcgg ccttgacaag   1920
ctgagagggt ctacatacga gagctgggtc aacttcaacc gctataggcg cgagatgaca   1980
cttaccgtcc tcgacctgat cgcgctcttc cctctgtacg acgtcagact ttactcgaag   2040
ggtgtcaaga ccgagttgac cagggacgtg cttaccgacc caatcgtcgg cgtcaacaac   2100
ctgcgcggct acgggaccac cttcagcaac atcgagaact acatcaggaa gccgcacctg   2160
ttcgactacc tgcaccgcat tcagttccac accaggctgc agcccggcta ctacggcaac   2220
gacagcttca actactggag cggcaactac gtgtctacca gacccagcat cggctccaac   2280
gacatcatca cgtccccgtt ctacggcaac aagagcagcg agccggtcca gaacctggag   2340
ttcaacggcg agaaggtcta tcgcgctgtc gccaacacca acctcgcggt ctggccgagc   2400
gcggtgtaca gcggcgtcac taaggtcgag ttcagccagt acaacgacca gaccgacgag   2460
gcgtccacgc agacctacga cagcaagagg aacgttggcg ccgtctcctg ggacagcatc   2520
gaccagctcc cgccagagac cactgacgag ccacttgaga aggcttatag ccaccagctg   2580
aactacgtca tgtgcttcct catgcaaggc tctcgcggca ccattccggt gttcacctgg   2640
acacacaaga gcgttgactt cttcaacacc atcgacagca agaagatcac ccagctcccg   2700
cttgtgaagg cctacaagct ccagagcggc gcgagcgtgg tcgccgggcc tggtttcaca   2760
ggcggcgaca tcattcagtg tacggagaac ggcagcgcgg ccaccatcta cgtcacgccg   2820
gacgtgagct actcccagaa gtacagagcc cgcatccact acgcctccac gagccagatc   2880
accttcaccc tgagcctcga cggcgcgccc ttcaaccagt actacttcga caagaccatg   2940
aacaagggcg acacactgac ctacaacagc ttcaacctgg ctagcttctc taccccattc   3000
gagctgagcg gcaacaacct gcagatcggc gtcacaggcc tcagcgccgg cgacaaggtg   3060
```

```
tacatcgaca agattgagtt catcccggtc tga                                  3093


<210> SEQ ID NO 2
<211> LENGTH: 1030
<212> TYPE: PRT
<213> ORGANISM: Artificial Sequence
<220> FEATURE:
<223> OTHER INFORMATION: MBP-SA-IP3-1

<400> SEQUENCE: 2

Met Asp Lys Ile Glu Glu Gly Lys Leu Val Ile Trp Ile Asn Gly Asp
 1               5                  10                  15

Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
        35                  40                  45

Phe Pro Gln Val Ala Ala Thr Gly Asp Gly Pro Asp Ile Ile Phe Trp
    50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
            100                 105                 110

Glu Ala Leu Ser Leu Ile Tyr Asn Lys Asp Leu Leu Pro Asn Pro Pro
        115                 120                 125

Lys Thr Trp Glu Glu Ile Pro Ala Leu Asp Lys Glu Leu Lys Ala Lys
    130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
            180                 185                 190

Gly Leu Thr Phe Leu Val Asp Leu Ile Lys Asn Lys His Met Asn Ala
        195                 200                 205

Asp Thr Asp Tyr Ser Ile Ala Glu Ala Ala Phe Asn Lys Gly Glu Thr
    210                 215                 220

Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
            260                 265                 270

Pro Asn Lys Glu Leu Ala Lys Glu Phe Leu Glu Asn Tyr Leu Leu Thr
        275                 280                 285

Asp Glu Gly Leu Glu Ala Val Asn Lys Asp Lys Pro Leu Gly Ala Val
    290                 295                 300

Ala Leu Lys Ser Tyr Glu Glu Glu Leu Ala Lys Asp Pro Arg Ile Ala
305                 310                 315                 320

Ala Thr Met Glu Asn Ala Gln Lys Gly Glu Ile Met Pro Asn Ile Pro
                325                 330                 335

Gln Met Ser Ala Phe Trp Tyr Ala Val Arg Thr Ala Val Ile Asn Ala
            340                 345                 350

Ala Ser Gly Arg Gln Thr Val Asp Glu Ala Leu Lys Asp Ala Gln Thr
```

```
        355                 360                 365

Arg Ile Thr Lys Ser Met Ser Ala Ser Ala Ser Ala Ser Ala Ser Ala
    370                 375                 380

Ser Ala Arg Met Asn Pro Asn Asn Arg Ser Glu His Asp Thr Ile Lys
385                 390                 395                 400

Thr Thr Glu Asn Asn Glu Val Pro Thr Asn His Val Gln Tyr Pro Leu
                405                 410                 415

Ala Glu Thr Pro Asn Pro Thr Leu Glu Asp Leu Asn Tyr Lys Glu Phe
            420                 425                 430

Leu Arg Met Thr Ala Asp Asn Asn Thr Glu Ala Leu Asp Ser Ser Thr
        435                 440                 445

Thr Lys Asp Val Ile Gln Lys Gly Ile Ser Val Val Gly Asp Leu Leu
    450                 455                 460

Gly Val Val Gly Phe Pro Phe Gly Gly Ala Leu Val Ser Phe Tyr Thr
465                 470                 475                 480

Asn Phe Leu Asn Thr Ile Trp Pro Ser Glu Asp Pro Leu Lys Ala Phe
                485                 490                 495

Met Glu Gln Val Glu Ala Leu Ile Asp Gln Lys Ile Ala Asp Tyr Ala
            500                 505                 510

Lys Asn Lys Ala Leu Ala Glu Leu Gln Gly Leu Gln Asn Asn Phe Glu
        515                 520                 525

Asp Tyr Val Ser Ala Leu Ser Ser Trp Gln Lys Asn Pro Val Ser Ser
    530                 535                 540

Arg Asn Pro His Ser Gln Gly Arg Ile Arg Glu Leu Phe Ser Gln Ala
545                 550                 555                 560

Glu Ser His Phe Arg Asn Ser Met Pro Ser Phe Ala Val Ser Gly Tyr
                565                 570                 575

Glu Val Leu Phe Leu Thr Thr Tyr Ala Gln Ala Ala Asn Thr His Leu
            580                 585                 590

Leu Leu Leu Lys Asp Ala Gln Ile Tyr Gly Glu Glu Trp Gly Tyr Glu
        595                 600                 605

Lys Glu Asp Ile Ala Glu Phe Tyr His Arg Gln Leu Lys Leu Thr Gln
    610                 615                 620

Glu Tyr Thr Asp His Cys Val Lys Trp Tyr Asn Val Gly Leu Asp Lys
625                 630                 635                 640

Leu Arg Gly Ser Thr Tyr Glu Ser Trp Val Asn Phe Asn Arg Tyr Arg
                645                 650                 655

Arg Glu Met Thr Leu Thr Val Leu Asp Leu Ile Ala Leu Phe Pro Leu
            660                 665                 670

Tyr Asp Val Arg Leu Tyr Ser Lys Gly Val Lys Thr Glu Leu Thr Arg
        675                 680                 685

Asp Val Leu Thr Asp Pro Ile Val Gly Val Asn Asn Leu Arg Gly Tyr
    690                 695                 700

Gly Thr Thr Phe Ser Asn Ile Glu Asn Tyr Ile Arg Lys Pro His Leu
705                 710                 715                 720

Phe Asp Tyr Leu His Arg Ile Gln Phe His Thr Arg Leu Gln Pro Gly
                725                 730                 735

Tyr Tyr Gly Asn Asp Ser Phe Asn Tyr Trp Ser Gly Asn Tyr Val Ser
            740                 745                 750

Thr Arg Pro Ser Ile Gly Ser Asn Asp Ile Ile Thr Ser Pro Phe Tyr
        755                 760                 765

Gly Asn Lys Ser Ser Glu Pro Val Gln Asn Leu Glu Phe Asn Gly Glu
    770                 775                 780
```

```
Lys Val Tyr Arg Ala Val Ala Asn Thr Asn Leu Ala Val Trp Pro Ser
785                 790                 795                 800

Ala Val Tyr Ser Gly Val Thr Lys Val Glu Phe Ser Gln Tyr Asn Asp
                805                 810                 815

Gln Thr Asp Glu Ala Ser Thr Gln Thr Tyr Asp Ser Lys Arg Asn Val
            820                 825                 830

Gly Ala Val Ser Trp Asp Ser Ile Asp Gln Leu Pro Pro Glu Thr Thr
        835                 840                 845

Asp Glu Pro Leu Glu Lys Ala Tyr Ser His Gln Leu Asn Tyr Val Met
    850                 855                 860

Cys Phe Leu Met Gln Gly Ser Arg Gly Thr Ile Pro Val Phe Thr Trp
865                 870                 875                 880

Thr His Lys Ser Val Asp Phe Phe Asn Thr Ile Asp Ser Lys Lys Ile
                885                 890                 895

Thr Gln Leu Pro Leu Val Lys Ala Tyr Lys Leu Gln Ser Gly Ala Ser
            900                 905                 910

Val Val Ala Gly Pro Gly Phe Thr Gly Gly Asp Ile Ile Gln Cys Thr
        915                 920                 925

Glu Asn Gly Ser Ala Ala Thr Ile Tyr Val Thr Pro Asp Val Ser Tyr
    930                 935                 940

Ser Gln Lys Tyr Arg Ala Arg Ile His Tyr Ala Ser Thr Ser Gln Ile
945                 950                 955                 960

Thr Phe Thr Leu Ser Leu Asp Gly Ala Pro Phe Asn Gln Tyr Tyr Phe
                965                 970                 975

Asp Lys Thr Met Asn Lys Gly Asp Thr Leu Thr Tyr Asn Ser Phe Asn
            980                 985                 990

Leu Ala Ser Phe Ser Thr Pro Phe Glu Leu Ser Gly Asn Asn Leu Gln
        995                 1000                1005

Ile Gly Val Thr Gly Leu Ser Ala Gly Asp Lys Val Tyr Ile Asp Lys
    1010                1015                1020

Ile Glu Phe Ile Pro Val
1025                1030
```

<210> SEQ ID NO 3
<211> LENGTH: 1179
<212> TYPE: DNA
<213> ORGANISM: Artificial Sequence
<220> FEATURE:
<223> OTHER INFORMATION: NEB- pMAL-MBP
<220> FEATURE:
<221> NAME/KEY: misc_feature
<222> LOCATION: (1)...(1104)
<223> OTHER INFORMATION: MBP
<220> FEATURE:
<221> NAME/KEY: misc_feature
<222> LOCATION: (1105)...(1179)
<223> OTHER INFORMATION: Linker

<400> SEQUENCE: 3

```
atggacaaaa tcgaagaagg taaactggta atctggatta acggcgataa aggctataac      60

ggtctcgctg aagtcggtaa gaaattcgag aaagataccg gaattaaagt caccgttgag     120

catccggata aactggaaga gaaattccca caggttgcgg caactggcga tggccctgac     180

attatcttct gggcacacga ccgctttggt ggctacgctc aatctggcct gttggctgaa     240

atcaccccgg acaaagcgtt ccaggacaag ctgtatccgt ttacctggga tgccgtacgt     300

tacaacggca agctgattgc ttacccgatc gctgttgaag cgttatcgct gatttataac     360
```

```
aaagatctgc tgccgaaccc gccaaaaacc tgggaagaga tcccggcgct ggataaagaa    420

ctgaaagcga aaggtaagag cgcgctgatg ttcaacctgc aagaaccgta cttcacctgg    480

ccgctgattg ctgctgacgg gggttatgcg ttcaagtatg aaaacggcaa gtacgacatt    540

aaagacgtgg gcgtggataa cgctggcgcg aaagcgggtc tgaccttcct ggttgacctg    600

attaaaaaca aacacatgaa tgcagacacc gattactcca tcgcagaagc tgcctttaat    660

aaaggcgaaa cagcgatgac catcaacggc ccgtgggcat ggtccaacat cgacaccagc    720

aaagtgaatt atggtgtaac ggtactgccg accttcaagg gtcaaccatc caaaccgttc    780

gttggcgtgc tgagcgcagg tattaacgcc gccagtccga acaaagagct ggcaaaagag    840

ttcctcgaaa actatctgct gactgatgaa ggtctggaag cggttaataa agacaaaccg    900

ctgggtgccg tagcgctgaa gtcttacgag gaagagttgg cgaaagatcc acgtattgcc    960

gccactatgg aaaacgccca gaaaggtgaa atcatgccga acatcccgca gatgtccgct   1020

ttctggtatg ccgtgcgtac tgcggtgatc aacgccgcca gcggtcgtca gactgtcgat   1080

gaagccctga aagacgcgca gactaattcg agctcgaaca acaacaacaa taacaataac   1140

aacaacctcg ggatcgaggg aaggatttca gaattaggc                          1179
```

<210> SEQ ID NO 4
<211> LENGTH: 393
<212> TYPE: PRT
<213> ORGANISM: Artificial Sequence
<220> FEATURE:
<223> OTHER INFORMATION: NEB-pMAL-MBP

<400> SEQUENCE: 4

```
Met Asp Lys Ile Glu Glu Gly Lys Leu Val Ile Trp Ile Asn Gly Asp
 1               5                  10                  15

Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
        35                  40                  45

Phe Pro Gln Val Ala Ala Thr Gly Asp Gly Pro Asp Ile Ile Phe Trp
    50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
            100                 105                 110

Glu Ala Leu Ser Leu Ile Tyr Asn Lys Asp Leu Leu Pro Asn Pro Pro
        115                 120                 125

Lys Thr Trp Glu Glu Ile Pro Ala Leu Asp Lys Glu Leu Lys Ala Lys
    130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
            180                 185                 190

Gly Leu Thr Phe Leu Val Asp Leu Ile Lys Asn Lys His Met Asn Ala
        195                 200                 205

Asp Thr Asp Tyr Ser Ile Ala Glu Ala Ala Phe Asn Lys Gly Glu Thr
    210                 215                 220
```

```
Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
            260                 265                 270

Pro Asn Lys Glu Leu Ala Lys Glu Phe Leu Glu Asn Tyr Leu Leu Thr
        275                 280                 285

Asp Glu Gly Leu Glu Ala Val Asn Lys Asp Lys Pro Leu Gly Ala Val
    290                 295                 300

Ala Leu Lys Ser Tyr Glu Glu Glu Leu Ala Lys Asp Pro Arg Ile Ala
305                 310                 315                 320

Ala Thr Met Glu Asn Ala Gln Lys Gly Glu Ile Met Pro Asn Ile Pro
                325                 330                 335

Gln Met Ser Ala Phe Trp Tyr Ala Val Arg Thr Ala Val Ile Asn Ala
            340                 345                 350

Ala Ser Gly Arg Gln Thr Val Asp Glu Ala Leu Lys Asp Ala Gln Thr
        355                 360                 365

Asn Ser Ser Ser Asn Asn Asn Asn Asn Asn Asn Asn Asn Asn Leu Gly
    370                 375                 380

Ile Glu Gly Arg Ile Ser Glu Leu Gly
385                 390
```

<210> SEQ ID NO 5
<211> LENGTH: 1161
<212> TYPE: DNA
<213> ORGANISM: Artificial Sequence
<220> FEATURE:
<223> OTHER INFORMATION: MBP-SA
<220> FEATURE:
<221> NAME/KEY: misc_feature
<222> LOCATION: (1)...(1104)
<223> OTHER INFORMATION: MBP
<220> FEATURE:
<221> NAME/KEY: misc_feature
<222> LOCATION: (1105)...(1161)
<223> OTHER INFORMATION: Linker

<400> SEQUENCE: 5

```
atggacaaaa tcgaagaagg taaactggta atctggatta acggcgataa aggctataac     60

ggtctcgctg aagtcggtaa gaaattcgag aaagataccg gaattaaagt caccgttgag    120

catccggata aactggaaga gaaattccca caggttgcgg caactggcga tggccctgac    180

attatcttct gggcacacga ccgctttggt ggctacgctc aatctggcct gttggctgaa    240

atcaccccgg acaaagcgtt ccaggacaag ctgtatccgt ttacctggga tgccgtacgt    300

tacaacggca agctgattgc ttacccgatc gctgttgaag cgttatcgct gatttataac    360

aaagatctgc tgccgaaccc gccaaaaacc tgggaagaga tcccggcgct ggataaagaa    420

ctgaaagcga aaggtaagag cgcgctgatg ttcaacctgc aagaaccgta cttcacctgg    480

ccgctgattg ctgctgacgg gggttatgcg ttcaagtatg aaaacggcaa gtacgacatt    540

aaagacgtgg gcgtggataa cgctggcgcg aaagcgggtc tgaccttcct ggttgacctg    600

attaaaaaca aacacatgaa tgcagacacc gattactcca tcgcagaagc tgcctttaat    660

aaaggcgaaa cagcgatgac catcaacggc ccgtgggcat ggtccaacat cgacaccagc    720

aaagtgaatt atggtgtaac ggtactgccg accttcaagg gtcaaccatc caaaccgttc    780

gttggcgtgc tgagcgcagg tattaacgcc gccagtccga acaaagagct ggcaaaagag    840
```

```
ttcctcgaaa actatctgct gactgatgaa ggtctggaag cggttaataa agacaaaccg    900

ctgggtgccg tagcgctgaa gtcttacgag gaagagttgg cgaaagatcc acgtattgcc    960

gccactatgg aaaacgccca gaaaggtgaa atcatgccga acatcccgca gatgtccgct   1020

ttctggtatg ccgtgcgtac tgcggtgatc aacgccgcca gcggtcgtca gactgtcgat   1080

gaagccctga aagacgcgca gactcgtatc accaagagca tgtctgcatc tgcatctgca   1140

tctgcatctg catctgcacg c                                              1161


<210> SEQ ID NO 6
<211> LENGTH: 387
<212> TYPE: PRT
<213> ORGANISM: Artificial Sequence
<220> FEATURE:
<223> OTHER INFORMATION: MBP-SA

<400> SEQUENCE: 6

Met Asp Lys Ile Glu Glu Gly Lys Leu Val Ile Trp Ile Asn Gly Asp
 1               5                  10                  15

Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
        35                  40                  45

Phe Pro Gln Val Ala Ala Thr Gly Asp Gly Pro Asp Ile Ile Phe Trp
    50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
            100                 105                 110

Glu Ala Leu Ser Leu Ile Tyr Asn Lys Asp Leu Leu Pro Asn Pro Pro
        115                 120                 125

Lys Thr Trp Glu Glu Ile Pro Ala Leu Asp Lys Glu Leu Lys Ala Lys
    130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
            180                 185                 190

Gly Leu Thr Phe Leu Val Asp Leu Ile Lys Asn Lys His Met Asn Ala
        195                 200                 205

Asp Thr Asp Tyr Ser Ile Ala Glu Ala Ala Phe Asn Lys Gly Glu Thr
    210                 215                 220

Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
            260                 265                 270

Pro Asn Lys Glu Leu Ala Lys Glu Phe Leu Glu Asn Tyr Leu Leu Thr
        275                 280                 285

Asp Glu Gly Leu Glu Ala Val Asn Lys Asp Lys Pro Leu Gly Ala Val
    290                 295                 300
```

```
Ala Leu Lys Ser Tyr Glu Glu Glu Leu Ala Lys Asp Pro Arg Ile Ala
305                 310                 315                 320

Ala Thr Met Glu Asn Ala Gln Lys Gly Glu Ile Met Pro Asn Ile Pro
                325                 330                 335

Gln Met Ser Ala Phe Trp Tyr Ala Val Arg Thr Ala Val Ile Asn Ala
            340                 345                 350

Ala Ser Gly Arg Gln Thr Val Asp Glu Ala Leu Lys Asp Ala Gln Thr
        355                 360                 365

Arg Ile Thr Lys Ser Met Ser Ala Ser Ala Ser Ala Ser Ala Ser Ala
    370                 375                 380

Ser Ala Arg
385
```

<210> SEQ ID NO 7
<211> LENGTH: 1932
<212> TYPE: DNA
<213> ORGANISM: Artificial Sequence
<220> FEATURE:
<223> OTHER INFORMATION: IP3-1

<400> SEQUENCE: 7

```
atgaacccta acaacaggtc agagcacgac acgatcaaga caaccgagaa caacgaggtg     60
ccgacgaacc acgtccagta cccactcgcc gaaacaccga accctaccct ggaggacctc    120
aactacaagg agttcctgag gatgacagcg gacaacaaca ccgaagccct cgactctagc    180
acgaccaagg acgtgattca gaagggcatc tctgtggtcg gcgacctgct tggcgttgtc    240
gggttcccgt tcggcggcgc tctcgtcagc ttctacacga acttcttgaa caccatctgg    300
ccgtccgaag accccctcaa ggcgttcatg gagcaggtgg aggccctcat cgaccagaag    360
atcgctgact atgccaagaa caaggctctg gcggagctgc aaggcctgca gaacaacttc    420
gaggactatg tgagcgccct cagctcttgg cagaagaacc cagtcagctc ccgcaacccg    480
cacagccagg gccgcatcag ggagctgttc agccaggccg agagccactt ccgcaactcc    540
atgccgagct tcgccgtgag cggctacgag gtcctcttcc tgactaccta tgcccaggct    600
gccaacaccc acttgcttct cctgaaggac gcccagatct acggcgaaga gtggggctac    660
gagaaggagg acatcgccga gttctaccac aggcagctca agctgacgca ggagtacacc    720
gaccactgcg tgaagtggta caacgtcggc cttgacaagc tgagagggtc tacatacgag    780
agctgggtca acttcaaccg ctataggcgc gagatgacac ttaccgtcct cgacctgatc    840
gcgctcttcc ctctgtacga cgtcagactt tactcgaagg gtgtcaagac cgagttgacc    900
agggacgtgc ttaccgaccc aatcgtcggc gtcaacaacc tgcgcggcta cgggaccacc    960
ttcagcaaca tcgagaacta catcaggaag ccgcacctgt tcgactacct gcaccgcatt   1020
cagttccaca ccaggctgca gcccggctac tacggcaacg acagcttcaa ctactggagc   1080
ggcaactacg tgtctaccag acccagcatc ggctccaacg acatcatcac gtccccgttc   1140
tacggcaaca agagcagcga gccggtccag aacctggagt tcaacggcga gaaggtctat   1200
cgcgctgtcg ccaacaccaa cctcgcggtc tggccgagcg cggtgtacag cggcgtcact   1260
aaggtcgagt tcagccagta caacgaccag accgacgagg cgtccacgca gacctacgac   1320
agcaagagga acgttggcgc cgtctcctgg gacagcatcg accagctccc gccagagacc   1380
actgacgagc cacttgagaa ggcttatagc caccagctga actacgtcat gtgcttcctc   1440
atgcaaggct ctcgcggcac cattccggtg ttcacctgga cacacaagag cgttgacttc   1500
```

```
ttcaacacca tcgacagcaa gaagatcacc cagctcccgc ttgtgaaggc ctacaagctc   1560

cagagcggcg cgagcgtggt cgccgggcct ggtttcacag gcggcgacat cattcagtgt   1620

acggagaacg gcagcgcggc caccatctac gtcacgccgg acgtgagcta ctcccagaag   1680

tacagagccc gcatccacta cgcctccacg agccagatca ccttcaccct gagcctcgac   1740

ggcgcgccct tcaaccagta ctacttcgac aagaccatga acaagggcga cacactgacc   1800

tacaacagct tcaacctggc tagcttctct accccattcg agctgagcgg caacaacctg   1860

cagatcggcg tcacaggcct cagcgccggc gacaaggtgt acatcgacaa gattgagttc   1920

atcccggtct ga                                                         1932
```

```
<210> SEQ ID NO 8
<211> LENGTH: 643
<212> TYPE: PRT
<213> ORGANISM: Artificial Sequence
<220> FEATURE:
<223> OTHER INFORMATION: IP3-1

<400> SEQUENCE: 8

Met Asn Pro Asn Asn Arg Ser Glu His Asp Thr Ile Lys Thr Thr Glu
 1               5                  10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
    50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Leu Lys Ala Phe Met Glu Gln
            100                 105                 110

Val Glu Ala Leu Ile Asp Gln Lys Ile Ala Asp Tyr Ala Lys Asn Lys
        115                 120                 125

Ala Leu Ala Glu Leu Gln Gly Leu Gln Asn Asn Phe Glu Asp Tyr Val
    130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Val Ser Gly Tyr Glu Val Leu
            180                 185                 190

Phe Leu Thr Thr Tyr Ala Gln Ala Ala Asn Thr His Leu Leu Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr His Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Thr Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285
```

```
Arg Leu Tyr Ser Lys Gly Val Lys Thr Glu Leu Thr Arg Asp Val Leu
    290                 295                 300

Thr Asp Pro Ile Val Gly Val Asn Asn Leu Arg Gly Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Leu Gln Pro Gly Tyr Tyr Gly
            340                 345                 350

Asn Asp Ser Phe Asn Tyr Trp Ser Gly Asn Tyr Val Ser Thr Arg Pro
        355                 360                 365

Ser Ile Gly Ser Asn Asp Ile Ile Thr Ser Pro Phe Tyr Gly Asn Lys
    370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro
    450                 455                 460

Leu Glu Lys Ala Tyr Ser His Gln Leu Asn Tyr Val Met Cys Phe Leu
465                 470                 475                 480

Met Gln Gly Ser Arg Gly Thr Ile Pro Val Phe Thr Trp Thr His Lys
                485                 490                 495

Ser Val Asp Phe Phe Asn Thr Ile Asp Ser Lys Lys Ile Thr Gln Leu
            500                 505                 510

Pro Leu Val Lys Ala Tyr Lys Leu Gln Ser Gly Ala Ser Val Val Ala
        515                 520                 525

Gly Pro Gly Phe Thr Gly Gly Asp Ile Ile Gln Cys Thr Glu Asn Gly
    530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Met Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val
```

<210> SEQ ID NO 9
<211> LENGTH: 2049
<212> TYPE: DNA
<213> ORGANISM: Artificial Sequence
<220> FEATURE:
<223> OTHER INFORMATION: 2A-12

<400> SEQUENCE: 9

```
atgcgaatga gtccaaataa tcaaaatgaa tatgaaatta tagatgcgac accttctact     60
tctgtatcca atgattctaa cagataccct tttgcgaatg agccaacaaa tgcgctacaa    120
aatatggatt ataaagatta tttaaaaatg tctgcgggaa atgctagtga ataccctggt    180
tcacctgaag tacttgtcag cggacaagat gcagctaagg ccgcaattga tatagtaggt    240
aaattactat caggtttagg ggtcccattt gttgggccga tagtgagtct ttatactcaa    300
cttattgata ttctgtggcc ttcagggcaa aagagtcaat gggagatttt tatggaacaa    360
gtagaagaac tcataaatca aaaaatagca gaatatgcaa ggaataaagc gctttcggaa    420
ttagaaggat taggtaataa ttaccaatta tatctaaccg cgcttgaaga atggaaagaa    480
aatccatttc gtagaggatt tagaagaggt gccttacgag atgcgcgaaa tcgatttgaa    540
atcctggata gtttatttac gcaatatatg ccatctttta gagtgacaaa ttttgaagta    600
ccattcctta ctgtatatgc aatggcagcc aaccttcatt tactgttatt aaaggacgcg    660
tcaatttttg gagaagaatg ggatggtca acaactacta ttaataacta ttatgatcgt    720
caaatgaaac ttactgcaga atattctgat cactgtgtaa agtggtatga aactggttta    780
gcaaaattaa aaggcacgag cgctaaacaa tgggtcgact acaaccaatt ccgtagagaa    840
atgacactga cggttttaga tgttgttgca ttattcccaa attatgacac acgcacgtac    900
ccaatggaaa cgaaagcaca actaacaagg gaagtatata cagatccact gggcgcggta    960
aacgtgtctt caattggttc ctggtatgac aaagcacctt ctttcggagt gatagaatca   1020
tccgttattc gaccacccca tgtatttgat tatataacgg gactcacagt gtatacacaa   1080
tcaagaagca tttcttccgc tcgctatata agacattggg ctggtcatca aataagctac   1140
catcgtgtca gtaggggtag taatcttcaa caaatgtatg gaactaatca aaatctacac   1200
agcaccagta cctttgattt tacgaattat gatatttaca agacgttatc aaaagatgcg   1260
gtgctccttg atattgtttt tcctggttat acgtatatat tttttggaat gccagaagtc   1320
gagtttttca tggtaaacca attgaataat accagaaaga cgttaaagta taatccggtt   1380
tccaaagata ttatagcggg gacaagagat tcggaattag aattgcctcc agaaacttca   1440
gatcaaccaa attatgagtc aaatagccat agattatgtc atatcacaag tattcccgcg   1500
acgggtaaca ctaccggatt agtgcctgta ttttcttgga cacatcgaag tgcagattta   1560
aacaatacaa tatattcaga taaaatcact caaattccgg ccgttaaatg ttgggataat   1620
ttaccgtttg ttccagtggt aaaaggacca ggacatacag gaggggattt attacagtat   1680
aatagaagta ctggttctgt aggaacctta tttctagctc gatatggcct agcattagaa   1740
aaagcaggaa aatatcgtgt aagactgaga tatgctactg atgcagatat tgtattgcat   1800
gtaaacgatg ctcagattca gatgccaaaa acaatgaacc caggtgagga tctgacatct   1860
aaaactttta aagttgcaga tgctatcaca acagttaatt tagcaacaga tagttcggtt   1920
gcagttaaac ataatgttgg tgaagaccct aattcaacag tttctggtat agtttacgtt   1980
gaccgaatcg aattcatccc agtagatgag acatatgaag cggaacaaga tttagaagcg   2040
gccaaatga                                                           2049
```

<210> SEQ ID NO 10
<211> LENGTH: 682
<212> TYPE: PRT
<213> ORGANISM: Artificial Sequence
<220> FEATURE:
<223> OTHER INFORMATION: 2A-12

<400> SEQUENCE: 10

```
Met Arg Met Ser Pro Asn Asn Gln Asn Glu Tyr Glu Ile Ile Asp Ala
 1               5                  10                  15

Thr Pro Ser Thr Ser Val Ser Asn Asp Ser Asn Arg Tyr Pro Phe Ala
            20                  25                  30

Asn Glu Pro Thr Asn Ala Leu Gln Asn Met Asp Tyr Lys Asp Tyr Leu
        35                  40                  45

Lys Met Ser Ala Gly Asn Ala Ser Glu Tyr Pro Gly Ser Pro Glu Val
    50                  55                  60

Leu Val Ser Gly Gln Asp Ala Ala Lys Ala Ala Ile Asp Ile Val Gly
65                  70                  75                  80

Lys Leu Leu Ser Gly Leu Gly Val Pro Phe Val Gly Pro Ile Val Ser
                85                  90                  95

Leu Tyr Thr Gln Leu Ile Asp Ile Leu Trp Pro Ser Gly Gln Lys Ser
            100                 105                 110

Gln Trp Glu Ile Phe Met Glu Gln Val Glu Glu Leu Ile Asn Gln Lys
        115                 120                 125

Ile Ala Glu Tyr Ala Arg Asn Lys Ala Leu Ser Glu Leu Glu Gly Leu
    130                 135                 140

Gly Asn Asn Tyr Gln Leu Tyr Leu Thr Ala Leu Glu Glu Trp Lys Glu
145                 150                 155                 160

Asn Pro Phe Arg Arg Gly Phe Arg Arg Gly Ala Leu Arg Asp Ala Arg
                165                 170                 175

Asn Arg Phe Glu Ile Leu Asp Ser Leu Phe Thr Gln Tyr Met Pro Ser
            180                 185                 190

Phe Arg Val Thr Asn Phe Glu Val Pro Phe Leu Thr Val Tyr Ala Met
        195                 200                 205

Ala Ala Asn Leu His Leu Leu Leu Leu Lys Asp Ala Ser Ile Phe Gly
    210                 215                 220

Glu Glu Trp Gly Trp Ser Thr Thr Thr Ile Asn Asn Tyr Tyr Asp Arg
225                 230                 235                 240

Gln Met Lys Leu Thr Ala Glu Tyr Ser Asp His Cys Val Lys Trp Tyr
                245                 250                 255

Glu Thr Gly Leu Ala Lys Leu Lys Gly Thr Ser Ala Lys Gln Trp Val
            260                 265                 270

Asp Tyr Asn Gln Phe Arg Arg Glu Met Thr Leu Thr Val Leu Asp Val
        275                 280                 285

Val Ala Leu Phe Pro Asn Tyr Asp Thr Arg Thr Tyr Pro Met Glu Thr
    290                 295                 300

Lys Ala Gln Leu Thr Arg Glu Val Tyr Thr Asp Pro Leu Gly Ala Val
305                 310                 315                 320

Asn Val Ser Ser Ile Gly Ser Trp Tyr Asp Lys Ala Pro Ser Phe Gly
                325                 330                 335

Val Ile Glu Ser Ser Val Ile Arg Pro Pro His Val Phe Asp Tyr Ile
            340                 345                 350

Thr Gly Leu Thr Val Tyr Thr Gln Ser Arg Ser Ile Ser Ser Ala Arg
        355                 360                 365

Tyr Ile Arg His Trp Ala Gly His Gln Ile Ser Tyr His Arg Val Ser
    370                 375                 380

Arg Gly Ser Asn Leu Gln Gln Met Tyr Gly Thr Asn Gln Asn Leu His
385                 390                 395                 400

Ser Thr Ser Thr Phe Asp Phe Thr Asn Tyr Asp Ile Tyr Lys Thr Leu
                405                 410                 415
```

```
Ser Lys Asp Ala Val Leu Leu Asp Ile Val Phe Pro Gly Tyr Thr Tyr
            420                 425                 430

Ile Phe Phe Gly Met Pro Glu Val Glu Phe Phe Met Val Asn Gln Leu
        435                 440                 445

Asn Asn Thr Arg Lys Thr Leu Lys Tyr Asn Pro Val Ser Lys Asp Ile
    450                 455                 460

Ile Ala Gly Thr Arg Asp Ser Glu Leu Glu Leu Pro Pro Glu Thr Ser
465                 470                 475                 480

Asp Gln Pro Asn Tyr Glu Ser Asn Ser His Arg Leu Cys His Ile Thr
                485                 490                 495

Ser Ile Pro Ala Thr Gly Asn Thr Thr Gly Leu Val Pro Val Phe Ser
            500                 505                 510

Trp Thr His Arg Ser Ala Asp Leu Asn Asn Thr Ile Tyr Ser Asp Lys
        515                 520                 525

Ile Thr Gln Ile Pro Ala Val Lys Cys Trp Asp Asn Leu Pro Phe Val
    530                 535                 540

Pro Val Val Lys Gly Pro Gly His Thr Gly Gly Asp Leu Leu Gln Tyr
545                 550                 555                 560

Asn Arg Ser Thr Gly Ser Val Gly Thr Leu Phe Leu Ala Arg Tyr Gly
                565                 570                 575

Leu Ala Leu Glu Lys Ala Gly Lys Tyr Arg Val Arg Leu Arg Tyr Ala
            580                 585                 590

Thr Asp Ala Asp Ile Val Leu His Val Asn Asp Ala Gln Ile Gln Met
        595                 600                 605

Pro Lys Thr Met Asn Pro Gly Glu Asp Leu Thr Ser Lys Thr Phe Lys
    610                 615                 620

Val Ala Asp Ala Ile Thr Thr Val Asn Leu Ala Thr Asp Ser Ser Val
625                 630                 635                 640

Ala Val Lys His Asn Val Gly Glu Asp Pro Asn Ser Thr Val Ser Gly
                645                 650                 655

Ile Val Tyr Val Asp Arg Ile Glu Phe Ile Pro Val Asp Glu Thr Tyr
            660                 665                 670

Glu Ala Glu Gln Asp Leu Glu Ala Ala Lys
        675                 680
```

<210> SEQ ID NO 11
<211> LENGTH: 2010
<212> TYPE: DNA
<213> ORGANISM: Artificial Sequence
<220> FEATURE:
<223> OTHER INFORMATION: RX002-truncated

<400> SEQUENCE: 11

```
atgcgtccaa ataatcaaaa tgaatatgaa attatagata caccatctcg tacgtctgta      60

tctaatgatt ctgtcagata tccttttgcg aatgaaccaa caactgattt aaacaatatg     120

aattataaag atttccttaa aacagtaaat ggttacaata ctggagatct ttctggatct     180

gaagcattta tcagtcaaac agcaattagt actgcaggta aagctgtggg tacagtacta     240

gggttattgg gtgttccatt agccggagca gttggcccct taataacctt ctatggtacc     300

atcgcactat tattctgggg gccgggagat ccatggcaag cttttatgac ccaagtagag     360

gcattagtta accaaaaaat agcagattat gcaagaagta aagcaatctc agaattacaa     420

ggattaagga atattctcga tttatatcgt tcagcactta tagattggca agagaaccca     480

acaagaacaa gatcagtaac aaatatccgt tctcaatttg aaactgtaaa taattttttc     540
```

-continued

```
gaatatcaaa tgccatcttt tgcagtggca ggttatgagg ttccattgtt agcagtatat    600
gcacaggcgg caaatcttca tttatcaata ttaagagatg ccgcgacatt cggagcacaa    660
tggggaatgt ctcaaactgc tattaataac atatatgacc ttcagcagag aagaactgct    720
gagtatacta atcattgtgt gaaatggtat aataatggtt tagataaatt aagaggttcg    780
aatgctgggc aatgggttaa ttttaatcgc taccgtagag agatgacact aatggtattg    840
gatattgtag cgatatttcc aaactatgat acacgtacgt atccaagtgg aattggaact    900
agtgtccaac ttacaagaga agtatatacg gatcctattg gttcgacagc aacacaaggt    960
ggcgtttctt ggtatgacga agcaccttct tttacagcta ttgaaagttc cgtggttcga   1020
ccacttcact tatttgattt actaacaggc gttacagtct atgccgctag tagttcttgg   1080
gattcaagtc attattttag attttggaat gggcataaag tagacacaaa gggaattaat   1140
agttctattc aatatagtaa tgtatatggt tctactagta atgcggttag tacaactact   1200
atatcatttt cgggttttga agtttttaaa accatttcaa tagctggtgt actatttgct   1260
tggacaacaa ggtattttgg agtccctaaa gttcttttt ctaaaataga ccctatttct   1320
ggtattggaa gggattcaga atttagcgaa aggtatgcag ggattggaga acaaataaag   1380
aattcacttg aggaattacc tttacaaaca gaagatgagc cggattataa atcttatagt   1440
cataaattga atcatatttc aatggttcca caaactgtac gaacacggaa tgtacctgta   1500
ttttcttggt cgcatcggag tgcggatatt gacaatagaa tttttcagga tagaattaat   1560
caaattccgg tagtaaaggg acatacatta ggtccaggtg cttctgttat ggcaggtcct   1620
ggatttacag gaggaaatat agttactaga accagtccag gtgtagtagt tttttctgga   1680
gttactataa ataacgcatt atcacaaaga tatcgtgtga gaatacggta tgcttctact   1740
actgacttcc gatttttctc tacactttca ggaactcgtc tttatgccac tcaggctact   1800
aaaactatga ataaaggaca acaattaaca tatgaatcat ttcagtatgc aacaattaat   1860
tctacattta catttgagaa tataaatgat agtttgacaa taggtgcaga tcaatttcta   1920
agtggtgagc aagtctatgt agatagatat gaagtaatcc cagtggatgc aacgtttgag   1980
gcggagaacg atttagaggt ggcaaagtag                                    2010
```

<210> SEQ ID NO 12
<211> LENGTH: 669
<212> TYPE: PRT
<213> ORGANISM: Artificial Sequence
<220> FEATURE:
<223> OTHER INFORMATION: RX002-truncated

<400> SEQUENCE: 12

```
Met Arg Pro Asn Asn Gln Asn Glu Tyr Glu Ile Ile Asp Thr Pro Ser
 1               5                  10                  15

Arg Thr Ser Val Ser Asn Asp Ser Val Arg Tyr Pro Phe Ala Asn Glu
            20                  25                  30

Pro Thr Thr Asp Leu Asn Asn Met Asn Tyr Lys Asp Phe Leu Lys Thr
        35                  40                  45

Val Asn Gly Tyr Asn Thr Gly Asp Leu Ser Gly Ser Glu Ala Phe Ile
    50                  55                  60

Ser Gln Thr Ala Ile Ser Thr Ala Gly Lys Ala Val Gly Thr Val Leu
65                  70                  75                  80

Gly Leu Leu Gly Val Pro Leu Ala Gly Ala Val Gly Pro Leu Ile Thr
                85                  90                  95

Phe Tyr Gly Thr Ile Ala Leu Leu Phe Trp Gly Pro Gly Asp Pro Trp
```

```
            100                 105                 110

Gln Ala Phe Met Thr Gln Val Glu Ala Leu Val Asn Gln Lys Ile Ala
        115                 120                 125

Asp Tyr Ala Arg Ser Lys Ala Ile Ser Glu Leu Gln Gly Leu Arg Asn
    130                 135                 140

Ile Leu Asp Leu Tyr Arg Ser Ala Leu Ile Asp Trp Gln Glu Asn Pro
145                 150                 155                 160

Thr Arg Thr Arg Ser Val Thr Asn Ile Arg Ser Gln Phe Glu Thr Val
                165                 170                 175

Asn Asn Phe Phe Glu Tyr Gln Met Pro Ser Phe Ala Val Ala Gly Tyr
            180                 185                 190

Glu Val Pro Leu Leu Ala Val Tyr Ala Gln Ala Ala Asn Leu His Leu
        195                 200                 205

Ser Ile Leu Arg Asp Ala Ala Thr Phe Gly Ala Gln Trp Gly Met Ser
    210                 215                 220

Gln Thr Ala Ile Asn Asn Ile Tyr Asp Leu Gln Gln Arg Arg Thr Ala
225                 230                 235                 240

Glu Tyr Thr Asn His Cys Val Lys Trp Tyr Asn Asn Gly Leu Asp Lys
                245                 250                 255

Leu Arg Gly Ser Asn Ala Gly Gln Trp Val Asn Phe Asn Arg Tyr Arg
            260                 265                 270

Arg Glu Met Thr Leu Met Val Leu Asp Ile Val Ala Ile Phe Pro Asn
        275                 280                 285

Tyr Asp Thr Arg Thr Tyr Pro Ser Gly Ile Gly Thr Ser Val Gln Leu
    290                 295                 300

Thr Arg Glu Val Tyr Thr Asp Pro Ile Gly Ser Thr Ala Thr Gln Gly
305                 310                 315                 320

Gly Val Ser Trp Tyr Asp Glu Ala Pro Ser Phe Thr Ala Ile Glu Ser
                325                 330                 335

Ser Val Val Arg Pro Leu His Leu Phe Asp Leu Leu Thr Gly Val Thr
            340                 345                 350

Val Tyr Ala Ala Ser Ser Ser Trp Asp Ser Ser His Tyr Phe Arg Phe
        355                 360                 365

Trp Asn Gly His Lys Val Asp Thr Lys Gly Ile Asn Ser Ser Ile Gln
    370                 375                 380

Tyr Ser Asn Val Tyr Gly Ser Thr Ser Asn Ala Val Ser Thr Thr Thr
385                 390                 395                 400

Ile Ser Phe Ser Gly Phe Glu Val Phe Lys Thr Ile Ser Ile Ala Gly
                405                 410                 415

Val Leu Phe Ala Trp Thr Thr Arg Tyr Phe Gly Val Pro Lys Val Leu
            420                 425                 430

Phe Ser Lys Ile Asp Pro Ile Ser Gly Ile Gly Arg Asp Ser Glu Phe
        435                 440                 445

Ser Glu Arg Tyr Ala Gly Ile Gly Glu Gln Ile Lys Asn Ser Leu Glu
    450                 455                 460

Glu Leu Pro Leu Gln Thr Glu Asp Glu Pro Asp Tyr Lys Ser Tyr Ser
465                 470                 475                 480

His Lys Leu Asn His Ile Ser Met Val Pro Gln Thr Val Arg Thr Arg
                485                 490                 495

Asn Val Pro Val Phe Ser Trp Ser His Arg Ser Ala Asp Ile Asp Asn
            500                 505                 510

Arg Ile Phe Gln Asp Arg Ile Asn Gln Ile Pro Val Val Lys Gly His
        515                 520                 525
```

```
Thr Leu Gly Pro Gly Ala Ser Val Met Ala Gly Pro Gly Phe Thr Gly
    530                 535                 540

Gly Asn Ile Val Thr Arg Thr Ser Pro Gly Val Val Val Phe Ser Gly
545                 550                 555                 560

Val Thr Ile Asn Asn Ala Leu Ser Gln Arg Tyr Arg Val Arg Ile Arg
                565                 570                 575

Tyr Ala Ser Thr Thr Asp Phe Arg Phe Phe Ser Thr Leu Ser Gly Thr
            580                 585                 590

Arg Leu Tyr Ala Thr Gln Ala Thr Lys Thr Met Asn Lys Gly Gln Gln
        595                 600                 605

Leu Thr Tyr Glu Ser Phe Gln Tyr Ala Thr Ile Asn Ser Thr Phe Thr
    610                 615                 620

Phe Glu Asn Ile Asn Asp Ser Leu Thr Ile Gly Ala Asp Gln Phe Leu
625                 630                 635                 640

Ser Gly Glu Gln Val Tyr Val Asp Arg Tyr Glu Val Ile Pro Val Asp
                645                 650                 655

Ala Thr Phe Glu Ala Glu Asn Asp Leu Glu Val Ala Lys
            660                 665
```

```
<210> SEQ ID NO 13
<211> LENGTH: 1974
<212> TYPE: DNA
<213> ORGANISM: Artificial Sequence
<220> FEATURE:
<223> OTHER INFORMATION: Cry1Bd-4c6-truncated

<400> SEQUENCE: 13

atgacttcaa ataggaaaaa tgagaatgaa attataaatg ccttatcgat tccagctgta      60

tcgaatcatt ccgcacaaat ggatctatcg ctagatgctc gtattgagga ttctttgtgt     120

atagccgagg ggaataatat caatccactt gttagcgcat caacagtcca aacgggtata     180

aacatagctg gtagaatatt gggcgtatta ggtgtgccgt ttgctggaca actagctagt     240

ttttatagtt ttcttgttgg ggaattatgg cctagtggca gagatccatg ggaaattttc     300

ctggaacatg tagaacaact tataagacaa caagtaacag aaaatactag gaatacggct     360

attgctcgat tagaaggtct aggaaaaggc tatagatctt accagcaggc tcttgaaact     420

tggttagata accgaaatga tgcaagatca agaagcatta ttcttgagcg ctatgttgct     480

ttagaacttg acattactac tgctataccg cttttcagaa tacgaaatga agaagttcca     540

ttattaatgg tatatgctca agctgcaaat ttacacctat tattattgag agacgcatcc     600

ctttttggta gtgaatgggg gatggcatct tccgatgtta accaatatta ccaagaacaa     660

atcaggtata cagaggaata ttctaaccat tgcgtacaat ggtataatac agggctaaat     720

aacttaagag ggacaaatgc tgaaagttgg ctgcggtata atcaattccg tagagaccta     780

acgttagggg tattagattt agtagcccta ttcccaagct atgatactcg cacttatcca     840

atcaatacga gtgctcagtt aacaagagaa atttatacag atccaattgg gagaacaaat     900

gcaccttcag gatttgcaag tacgaattgg tttaataata atgcaccatc gttttctgcc     960

atagaggctg ccattttcag gcctccgcat ctacttgatt ttccagaaca acttacaatt    1020

tacagtgcat caagccgttg gagtagcact caacatatga attattgggt gggacatagg    1080

cttaacttcc gcccaatagg agggacatta aatacctcaa cacaaggact tactaataat    1140

acttcaatta atcctgtaac attacagttt acgtctcgtg acgtttatag aacagaatca    1200

aatgcaggga caaatatact atttactact cctgtgaatg gagtaccttg ggctagattt    1260
```

```
aattttataa accctcagaa tatttatgaa agaggcgcca ctacctacag tcaaccgtat   1320

cagggagttg ggattcaatt atttgattca gaaactgaat taccaccaga aacaacagaa   1380

cgaccaaatt atgaatcata tagtcataga ttatctcata taggactaat cataggaaac   1440

actttgagag caccagtcta ttcttggacg catcgtagtg cagatcgtac gaatacgatt   1500

ggaccaaata gaattactca aattcctgca gtgaagggaa gatttctttt taatggttct   1560

gtaatttcag gaccaggatt tactggtgga gacgtagtta gattgaatag gaataatggt   1620

aatattcaaa atagagggta tattgaagtt ccaattcaat tcacgtcgac atctaccaga   1680

tatcgagttc gagtacgtta tgcttctgta acctcgattg agctcaatgt taatttgggc   1740

aattcatcaa tttttacgaa cacattacca gcaacagctg catcattaga taatctacaa   1800

tcaggggatt ttggttatgt tgaaatcaac aatgctttta catccgcaac aggtaatata   1860

gtaggtgcta gaaattttag tgcaaatgca gaagtaataa tagacagatt tgaatttatc   1920

ccagttactg caaccttcga ggcagaatat gatttagaaa gagcacaaaa gtga         1974
```

<210> SEQ ID NO 14
<211> LENGTH: 657
<212> TYPE: PRT
<213> ORGANISM: Artificial Sequence
<220> FEATURE:
<223> OTHER INFORMATION: Cry1Bd-4c6-truncated

<400> SEQUENCE: 14

```
Met Thr Ser Asn Arg Lys Asn Glu Asn Glu Ile Ile Asn Ala Leu Ser
 1               5                  10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asn Thr Ala Ile Ala Arg Leu Glu Gly Leu Gly
        115                 120                 125

Arg Gly Tyr Arg Ser Tyr Gln Gln Ala Leu Glu Thr Trp Leu Asp Asn
    130                 135                 140

Arg Asn Asp Ala Arg Ser Arg Ser Ile Ile Leu Glu Arg Tyr Val Ala
145                 150                 155                 160

Leu Glu Leu Asp Ile Thr Thr Ala Ile Pro Leu Phe Arg Ile Arg Asn
                165                 170                 175

Glu Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Met
        195                 200                 205

Ala Ser Ser Asp Val Asn Gln Tyr Tyr Gln Glu Gln Ile Arg Tyr Thr
    210                 215                 220

Glu Glu Tyr Ser Asn His Cys Val Gln Trp Tyr Asn Thr Gly Leu Asn
225                 230                 235                 240
```

```
Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr Gln Gly Leu Thr Asn Asn Thr Ser Ile Asn
    370                 375                 380

Pro Val Thr Leu Gln Phe Thr Ser Arg Asp Val Tyr Arg Thr Glu Ser
385                 390                 395                 400

Asn Ala Gly Thr Asn Ile Leu Phe Thr Thr Pro Val Asn Gly Val Pro
                405                 410                 415

Trp Ala Arg Phe Asn Phe Ile Asn Pro Gln Asn Ile Tyr Glu Arg Gly
            420                 425                 430

Ala Thr Thr Tyr Ser Gln Pro Tyr Gln Gly Val Gly Ile Gln Leu Phe
        435                 440                 445

Asp Ser Glu Thr Glu Leu Pro Pro Glu Thr Thr Glu Arg Pro Asn Tyr
    450                 455                 460

Glu Ser Tyr Ser His Arg Leu Ser His Ile Gly Leu Ile Ile Gly Asn
465                 470                 475                 480

Thr Leu Arg Ala Pro Val Tyr Ser Trp Thr His Arg Ser Ala Asp Arg
                485                 490                 495

Thr Asn Thr Ile Gly Pro Asn Arg Ile Thr Gln Ile Pro Ala Val Lys
            500                 505                 510

Gly Arg Phe Leu Phe Asn Gly Ser Val Ile Ser Gly Pro Gly Phe Thr
        515                 520                 525

Gly Gly Asp Val Val Arg Leu Asn Arg Asn Asn Gly Asn Ile Gln Asn
    530                 535                 540

Arg Gly Tyr Ile Glu Val Pro Ile Gln Phe Thr Ser Thr Ser Thr Arg
545                 550                 555                 560

Tyr Arg Val Arg Val Arg Tyr Ala Ser Val Thr Ser Ile Glu Leu Asn
                565                 570                 575

Val Asn Leu Gly Asn Ser Ser Ile Phe Thr Asn Thr Leu Pro Ala Thr
            580                 585                 590

Ala Ala Ser Leu Asp Asn Leu Gln Ser Gly Asp Phe Gly Tyr Val Glu
        595                 600                 605

Ile Asn Asn Ala Phe Thr Ser Ala Thr Gly Asn Ile Val Gly Ala Arg
    610                 615                 620

Asn Phe Ser Ala Asn Ala Glu Val Ile Ile Asp Arg Phe Glu Phe Ile
625                 630                 635                 640

Pro Val Thr Ala Thr Phe Glu Ala Glu Tyr Asp Leu Glu Arg Ala Gln
                645                 650                 655
```

Lys

<210> SEQ ID NO 15
<211> LENGTH: 3570
<212> TYPE: DNA
<213> ORGANISM: Artificial Sequence
<220> FEATURE:
<223> OTHER INFORMATION: NusA-IP3-1
<220> FEATURE:
<221> NAME/KEY: misc_feature
<222> LOCATION: (1)...(1485)
<223> OTHER INFORMATION: NusA
<220> FEATURE:
<221> NAME/KEY: misc_feature
<222> LOCATION: (1486)...(1638)
<223> OTHER INFORMATION: Linker
<220> FEATURE:
<221> NAME/KEY: misc_feature
<222> LOCATION: (1639)...(3570)
<223> OTHER INFORMATION: IP3-1

<400> SEQUENCE: 15
atgaacaaag aaattttggc tgtagttgaa gccgtatcca atgaaaaggc gctacctcgc 60
gagaagattt tcgaagcatt ggaaagcgcg ctggcgacag caacaaagaa aaaatatgaa 120
caagagatcg acgtccgcgt acagatcgat cgcaaaagcg gtgattttga cactttccgt 180
cgctggttag ttgttgatga agtcacccag ccgaccaagg aaatcaccct tgaagccgca 240
cgttatgaag atgaaagcct gaacctgggc gattacgttg aagatcagat tgagtctgtt 300
acctttgacc gtatcactac ccagacggca aaacaggtta tcgtgcagaa agtgcgtgaa 360
gccgaacgtg cgatggtggt tgatcagttc cgtgaacacg aaggtgaaat catcaccggc 420
gtggtgaaaa aagtaaaccg cgacaacatc tctctggatc tgggcaacaa cgctgaagcc 480
gtgatcctgc gcgaagatat gctgccgcgt gaaaacttcc gccctggcga ccgcgttcgt 540
ggcgtgctct attccgttcg cccggaagcg cgtggcgcgc aactgttcgt cactcgttcc 600
aagccggaaa tgctgatcga actgttccgt attgaagtgc cagaaatcgg cgaagaagtg 660
attgaaatta aagcagcggc tcgcgatccg ggttctcgtg cgaaaatcgc ggtgaaaacc 720
aacgataaac gtatcgatcc ggtaggtgct tgcgtaggta tgcgtggcgc gcgtgttcag 780
gcggtgtcta ctgaactggg tggcgagcgt atcgatatcg tcctgtggga tgataacccg 840
gcgcagttcg tgattaacgc aatggcaccg gcagacgttg cttctatcgt ggtggatgaa 900
gataaacaca ccatggacat cgccgttgaa gccggtaatc tggcgcaggc gattggccgt 960
aacggtcaga acgtgcgtct ggcttcgcaa ctgagcggtt gggaactcaa cgtgatgacc 1020
gttgacgacc tgcaagctaa gcatcaggcg gaagcgcacg cagcgatcga caccttcacc 1080
aaatatctcg acatcgacga agacttcgcg actgttctgg tagaagaagg cttctcgacg 1140
ctggaagaat tggcctatgt gccgatgaaa gagctgttgg aaatcgaagg ccttgatgag 1200
ccgaccgttg aagcactgcg cgagcgtgct aaaaatgcac tggccaccat tgcacaggcc 1260
caggaagaaa gcctcggtga taacaaaccg gctgacgatc tgctgaacct tgaaggggta 1320
gatcgtgatt tggcattcaa actggccgcc cgtggcgttt gtacgctgga agatctcgcc 1380
gaacagggca ttgatgatct ggctgatatc gaagggttga ccgacgaaaa agccggagca 1440
ctgattatgg ctgcccgtaa tatttgctgg ttcggtgacg aagcgactag tggttctggt 1500
catcaccatc accatcactc cgcgggtaaa gaaaccgctg ctgcgaaatt tgaacgccag 1560
cacatggact cgccaccgcc aactggtctg gtcccccggg gcagcgcggg ttctggtacg 1620
attgatgacg acgacaagat gaaccctaac aacaggtcag agcacgacac gatcaagaca 1680

```
accgagaaca acgaggtgcc gacgaaccac gtccagtacc cactcgccga aacaccgaac   1740

cctaccctgg aggacctcaa ctacaaggag ttcctgagga tgacagcgga caacaacacc   1800

gaagccctcg actctagcac gaccaaggac gtgattcaga agggcatctc tgtggtcggc   1860

gacctgcttg gcgttgtcgg gttcccgttc ggcggcgctc tcgtcagctt ctacacgaac   1920

ttcttgaaca ccatctggcc gtccgaagac cccctcaagg cgttcatgga gcaggtggag   1980

gccctcatcg accagaagat cgctgactat gccaagaaca aggctctggc ggagctgcaa   2040

ggcctgcaga acaacttcga ggactatgtg agcgccctca gctcttggca gaagaaccca   2100

gtcagctccc gcaacccgca cagccagggc cgcatcaggg agctgttcag ccaggccgag   2160

agccacttcc gcaactccat gccgagcttc gccgtgagcg gctacgaggt cctcttcctg   2220

actacctatg cccaggctgc caacacccac ttgcttctcc tgaaggacgc ccagatctac   2280

ggcgaagagt ggggctacga gaaggaggac atcgccgagt tctaccacag gcagctcaag   2340

ctgacgcagg agtacaccga ccactgcgtg aagtggtaca acgtcggcct tgacaagctg   2400

agagggtcta catacgagag ctgggtcaac ttcaaccgct ataggcgcga gatgacactt   2460

accgtcctcg acctgatcgc gctcttccct ctgtacgacg tcagacttta ctcgaagggt   2520

gtcaagaccg agttgaccag ggacgtgctt accgacccaa tcgtcggcgt caacaacctg   2580

cgcggctacg ggaccacctt cagcaacatc gagaactaca tcaggaagcc gcacctgttc   2640

gactacctgc accgcattca gttccacacc aggctgcagc ccggctacta cggcaacgac   2700

agcttcaact actggagcgg caactacgtg tctaccagac ccagcatcgg ctccaacgac   2760

atcatcacgt ccccgttcta cggcaacaag agcagcgagc cggtccagaa cctggagttc   2820

aacggcgaga aggtctatcg cgctgtcgcc aacaccaacc tcgcggtctg gccgagcgcg   2880

gtgtacagcg gcgtcactaa ggtcgagttc agccagtaca acgaccagac cgacgaggcg   2940

tccacgcaga cctacgacag caagaggaac gttggcgccg tctcctggga cagcatcgac   3000

cagctcccgc cagagaccac tgacgagcca cttgagaagg cttatagcca ccagctgaac   3060

tacgtcatgt gcttcctcat gcaaggctct cgcggcacca ttccggtgtt cacctggaca   3120

cacaagagcg ttgacttctt caacaccatc gacagcaaga agatcaccca gctcccgctt   3180

gtgaaggcct acaagctcca gagcggcgcg agcgtggtcg ccgggcctgg tttcacaggc   3240

ggcgacatca ttcagtgtac ggagaacggc agcgcggcca ccatctacgt cacgccggac   3300

gtgagctact cccagaagta cagagcccgc atccactacg cctccacgag ccagatcacc   3360

ttcaccctga gcctcgacgg cgcgcccttc aaccagtact acttcgacaa gaccatgaac   3420

aagggcgaca cactgaccta caacagcttc aacctggcta gcttctctac cccattcgag   3480

ctgagcggca acaacctgca gatcggcgtc acaggcctca gcgccggcga caaggtgtac   3540

atcgacaaga ttgagttcat cccggtctga                                    3570
```

<210> SEQ ID NO 16
<211> LENGTH: 1189
<212> TYPE: PRT
<213> ORGANISM: Artificial Sequence
<220> FEATURE:
<223> OTHER INFORMATION: NusA-IP3-1
<220> FEATURE:
<221> NAME/KEY: DOMAIN
<222> LOCATION: (1)...(495)
<223> OTHER INFORMATION: NusA
<220> FEATURE:
<221> NAME/KEY: DOMAIN
<222> LOCATION: (496)...(546)

```
<223> OTHER INFORMATION: Linker
<220> FEATURE:
<221> NAME/KEY: DOMAIN
<222> LOCATION: (547)...(1189)
<223> OTHER INFORMATION: IP3-1

<400> SEQUENCE: 16

Met Asn Lys Glu Ile Leu Ala Val Val Glu Ala Val Ser Asn Glu Lys
 1               5                  10                  15

Ala Leu Pro Arg Glu Lys Ile Phe Glu Ala Leu Glu Ser Ala Leu Ala
            20                  25                  30

Thr Ala Thr Lys Lys Lys Tyr Glu Gln Glu Ile Asp Val Arg Val Gln
        35                  40                  45

Ile Asp Arg Lys Ser Gly Asp Phe Asp Thr Phe Arg Arg Trp Leu Val
    50                  55                  60

Val Asp Glu Val Thr Gln Pro Thr Lys Glu Ile Thr Leu Glu Ala Ala
65                  70                  75                  80

Arg Tyr Glu Asp Glu Ser Leu Asn Leu Gly Asp Tyr Val Glu Asp Gln
                85                  90                  95

Ile Glu Ser Val Thr Phe Asp Arg Ile Thr Thr Gln Thr Ala Lys Gln
            100                 105                 110

Val Ile Val Gln Lys Val Arg Glu Ala Glu Arg Ala Met Val Val Asp
        115                 120                 125

Gln Phe Arg Glu His Glu Gly Glu Ile Ile Thr Gly Val Val Lys Lys
    130                 135                 140

Val Asn Arg Asp Asn Ile Ser Leu Asp Leu Gly Asn Asn Ala Glu Ala
145                 150                 155                 160

Val Ile Leu Arg Glu Asp Met Leu Pro Arg Glu Asn Phe Arg Pro Gly
                165                 170                 175

Asp Arg Val Arg Gly Val Leu Tyr Ser Val Arg Pro Glu Ala Arg Gly
            180                 185                 190

Ala Gln Leu Phe Val Thr Arg Ser Lys Pro Glu Met Leu Ile Glu Leu
        195                 200                 205

Phe Arg Ile Glu Val Pro Glu Ile Gly Glu Glu Val Ile Glu Ile Lys
    210                 215                 220

Ala Ala Ala Arg Asp Pro Gly Ser Arg Ala Lys Ile Ala Val Lys Thr
225                 230                 235                 240

Asn Asp Lys Arg Ile Asp Pro Val Gly Ala Cys Val Gly Met Arg Gly
                245                 250                 255

Ala Arg Val Gln Ala Val Ser Thr Glu Leu Gly Gly Glu Arg Ile Asp
            260                 265                 270

Ile Val Leu Trp Asp Asp Asn Pro Ala Gln Phe Val Ile Asn Ala Met
        275                 280                 285

Ala Pro Ala Asp Val Ala Ser Ile Val Val Asp Glu Asp Lys His Thr
    290                 295                 300

Met Asp Ile Ala Val Glu Ala Gly Asn Leu Ala Gln Ala Ile Gly Arg
305                 310                 315                 320

Asn Gly Gln Asn Val Arg Leu Ala Ser Gln Leu Ser Gly Trp Glu Leu
                325                 330                 335

Asn Val Met Thr Val Asp Asp Leu Gln Ala Lys His Gln Ala Glu Ala
            340                 345                 350

His Ala Ala Ile Asp Thr Phe Thr Lys Tyr Leu Asp Ile Asp Glu Asp
        355                 360                 365

Phe Ala Thr Val Leu Val Glu Glu Gly Phe Ser Thr Leu Glu Glu Leu
    370                 375                 380
```

-continued

```
Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
            420                 425                 430

Asp Leu Leu Asn Leu Glu Gly Val Asp Arg Asp Leu Ala Phe Lys Leu
        435                 440                 445

Ala Ala Arg Gly Val Cys Thr Leu Glu Asp Leu Ala Glu Gln Gly Ile
    450                 455                 460

Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly Asp Glu Ala Thr
                485                 490                 495

Ser Gly Ser Gly His His His His His His Ser Ala Gly Lys Glu Thr
            500                 505                 510

Ala Ala Ala Lys Phe Glu Arg Gln His Met Asp Ser Pro Pro Pro Thr
        515                 520                 525

Gly Leu Val Pro Arg Gly Ser Ala Gly Ser Gly Thr Ile Asp Asp Asp
    530                 535                 540

Asp Lys Met Asn Pro Asn Asn Arg Ser Glu His Asp Thr Ile Lys Thr
545                 550                 555                 560

Thr Glu Asn Asn Glu Val Pro Thr Asn His Val Gln Tyr Pro Leu Ala
                565                 570                 575

Glu Thr Pro Asn Pro Thr Leu Glu Asp Leu Asn Tyr Lys Glu Phe Leu
            580                 585                 590

Arg Met Thr Ala Asp Asn Asn Thr Glu Ala Leu Asp Ser Ser Thr Thr
        595                 600                 605

Lys Asp Val Ile Gln Lys Gly Ile Ser Val Val Gly Asp Leu Leu Gly
    610                 615                 620

Val Val Gly Phe Pro Phe Gly Gly Ala Leu Val Ser Phe Tyr Thr Asn
625                 630                 635                 640

Phe Leu Asn Thr Ile Trp Pro Ser Glu Asp Pro Leu Lys Ala Phe Met
                645                 650                 655

Glu Gln Val Glu Ala Leu Ile Asp Gln Lys Ile Ala Asp Tyr Ala Lys
            660                 665                 670

Asn Lys Ala Leu Ala Glu Leu Gln Gly Leu Gln Asn Asn Phe Glu Asp
        675                 680                 685

Tyr Val Ser Ala Leu Ser Ser Trp Gln Lys Asn Pro Val Ser Ser Arg
    690                 695                 700

Asn Pro His Ser Gln Gly Arg Ile Arg Glu Leu Phe Ser Gln Ala Glu
705                 710                 715                 720

Ser His Phe Arg Asn Ser Met Pro Ser Phe Ala Val Ser Gly Tyr Glu
                725                 730                 735

Val Leu Phe Leu Thr Thr Tyr Ala Gln Ala Ala Asn Thr His Leu Leu
            740                 745                 750

Leu Leu Lys Asp Ala Gln Ile Tyr Gly Glu Glu Trp Gly Tyr Glu Lys
        755                 760                 765

Glu Asp Ile Ala Glu Phe Tyr His Arg Gln Leu Lys Leu Thr Gln Glu
    770                 775                 780

Tyr Thr Asp His Cys Val Lys Trp Tyr Asn Val Gly Leu Asp Lys Leu
785                 790                 795                 800
```

```
Arg Gly Ser Thr Tyr Glu Ser Trp Val Asn Phe Asn Arg Tyr Arg Arg
            805                 810                 815

Glu Met Thr Leu Thr Val Leu Asp Leu Ile Ala Leu Phe Pro Leu Tyr
            820                 825                 830

Asp Val Arg Leu Tyr Ser Lys Gly Val Lys Thr Glu Leu Thr Arg Asp
        835                 840                 845

Val Leu Thr Asp Pro Ile Val Gly Val Asn Asn Leu Arg Gly Tyr Gly
    850                 855                 860

Thr Thr Phe Ser Asn Ile Glu Asn Tyr Ile Arg Lys Pro His Leu Phe
865                 870                 875                 880

Asp Tyr Leu His Arg Ile Gln Phe His Thr Arg Leu Gln Pro Gly Tyr
            885                 890                 895

Tyr Gly Asn Asp Ser Phe Asn Tyr Trp Ser Gly Asn Tyr Val Ser Thr
            900                 905                 910

Arg Pro Ser Ile Gly Ser Asn Asp Ile Ile Thr Ser Pro Phe Tyr Gly
        915                 920                 925

Asn Lys Ser Ser Glu Pro Val Gln Asn Leu Glu Phe Asn Gly Glu Lys
    930                 935                 940

Val Tyr Arg Ala Val Ala Asn Thr Asn Leu Ala Val Trp Pro Ser Ala
945                 950                 955                 960

Val Tyr Ser Gly Val Thr Lys Val Glu Phe Ser Gln Tyr Asn Asp Gln
            965                 970                 975

Thr Asp Glu Ala Ser Thr Gln Thr Tyr Asp Ser Lys Arg Asn Val Gly
            980                 985                 990

Ala Val Ser Trp Asp Ser Ile Asp Gln Leu Pro Pro Glu Thr Thr Asp
        995                 1000                1005

Glu Pro Leu Glu Lys Ala Tyr Ser His Gln Leu Asn Tyr Val Met Cys
    1010                1015                1020

Phe Leu Met Gln Gly Ser Arg Gly Thr Ile Pro Val Phe Thr Trp Thr
1025                1030                1035                1040

His Lys Ser Val Asp Phe Phe Asn Thr Ile Asp Ser Lys Lys Ile Thr
            1045                1050                1055

Gln Leu Pro Leu Val Lys Ala Tyr Lys Leu Gln Ser Gly Ala Ser Val
            1060                1065                1070

Val Ala Gly Pro Gly Phe Thr Gly Gly Asp Ile Ile Gln Cys Thr Glu
        1075                1080                1085

Asn Gly Ser Ala Ala Thr Ile Tyr Val Thr Pro Asp Val Ser Tyr Ser
    1090                1095                1100

Gln Lys Tyr Arg Ala Arg Ile His Tyr Ala Ser Thr Ser Gln Ile Thr
1105                1110                1115                1120

Phe Thr Leu Ser Leu Asp Gly Ala Pro Phe Asn Gln Tyr Tyr Phe Asp
            1125                1130                1135

Lys Thr Met Asn Lys Gly Asp Thr Leu Thr Tyr Asn Ser Phe Asn Leu
            1140                1145                1150

Ala Ser Phe Ser Thr Pro Phe Glu Leu Ser Gly Asn Asn Leu Gln Ile
        1155                1160                1165

Gly Val Thr Gly Leu Ser Ala Gly Asp Lys Val Tyr Ile Asp Lys Ile
    1170                1175                1180

Glu Phe Ile Pro Val
1185
```

<210> SEQ ID NO 17
<211> LENGTH: 2406
<212> TYPE: DNA

```
<213> ORGANISM: Artificial Sequence
<220> FEATURE:
<223> OTHER INFORMATION: TrxA-IP3-1
<220> FEATURE:
<221> NAME/KEY: misc_feature
<222> LOCATION: (1)...(327)
<223> OTHER INFORMATION: TrxA
<220> FEATURE:
<221> NAME/KEY: misc_feature
<222> LOCATION: (328)...(474)
<223> OTHER INFORMATION: Linker
<220> FEATURE:
<221> NAME/KEY: misc_feature
<222> LOCATION: (475)...(2406)
<223> OTHER INFORMATION: IP3-1

<400> SEQUENCE: 17

atgagcgata aaattattca cctgactgac gacagttttg acacggatgt actcaaagcg     60

gacggggcga tcctcgtcga tttctgggca gagtggtgcg gtccgtgcaa aatgatcgcc    120

ccgattctgg atgaaatcgc tgacgaatat cagggcaaac tgaccgttgc aaaactgaac    180

atcgatcaaa accctggcac tgcgccgaaa tatggcatcc gtggtatccc gactctgctg    240

ctgttcaaaa acggtgaagt ggcggcaacc aaagtgggtg cactgtctaa aggtcagttg    300

aaagagttcc tcgacgctaa cctggccggt tctggttctg gccatatgca ccatcatcat    360

catcattctt ctggtctggt gccacgcggt tctggtatga aagaaaccgc tgctgctaaa    420

ttcgaacgcc agcacatgga cagcccagat ctgggtaccg atgacgacga caagatgaac    480

cctaacaaca ggtcagagca cgacacgatc aagacaaccg agaacaacga ggtgccgacg    540

aaccacgtcc agtacccact cgccgaaaca ccgaacccta ccctggagga cctcaactac    600

aaggagttcc tgaggatgac agcggacaac aacaccgaag ccctcgactc tagcacgacc    660

aaggacgtga ttcagaaggg catctctgtg gtcggcgacc tgcttggcgt tgtcgggttc    720

ccgttcggcg gcgctctcgt cagcttctac acgaacttct tgaacaccat ctggccgtcc    780

gaagaccccc tcaaggcgtt catggagcag gtggaggccc tcatcgacca gaagatcgct    840

gactatgcca agaacaaggc tctggcggag ctgcaaggcc tgcagaacaa cttcgaggac    900

tatgtgagcg ccctcagctc ttggcagaag aacccagtca gctcccgcaa cccgcacagc    960

cagggccgca tcagggagct gttcagccag gccgagagcc acttccgcaa ctccatgccg   1020

agcttcgccg tgagcggcta cgaggtcctc ttcctgacta cctatgccca ggctgccaac   1080

acccacttgc ttctcctgaa ggacgcccag atctacggcg aagagtgggg ctacgagaag   1140

gaggacatcg ccgagttcta ccacaggcag ctcaagctga cgcaggagta caccgaccac   1200

tgcgtgaagt ggtacaacgt cggccttgac aagctgagag ggtctacata cgagagctgg   1260

gtcaacttca accgctatag gcgcgagatg acacttaccg tcctcgacct gatcgcgctc   1320

ttccctctgt acgacgtcag actttactcg aagggtgtca agaccgagtt gaccagggac   1380

gtgcttaccg acccaatcgt cggcgtcaac aacctgcgcg gctacgggac caccttcagc   1440

aacatcgaga actacatcag gaagccgcac ctgttcgact acctgcaccg cattcagttc   1500

cacaccaggc tgcagcccgg ctactacggc aacgacagct tcaactactg gagcggcaac   1560

tacgtgtcta ccagacccag catcggctcc aacgacatca tcacgtcccc gttctacggc   1620

aacaagagca gcgagccggt ccagaacctg gagttcaacg gcgagaaggt ctatcgcgct   1680

gtcgccaaca ccaacctcgc ggtctggccg agcgcggtgt acagcggcgt cactaaggtc   1740

gagttcagcc agtacaacga ccagaccgac gaggcgtcca cgcagaccta cgacagcaag   1800

aggaacgttg gcgccgtctc ctgggacagc atcgaccagc tcccgccaga gaccactgac   1860
```

```
gagccacttg agaaggctta tagccaccag ctgaactacg tcatgtgctt cctcatgcaa   1920

ggctctcgcg gcaccattcc ggtgttcacc tggacacaca agagcgttga cttcttcaac   1980

accatcgaca gcaagaagat cacccagctc ccgcttgtga aggcctacaa gctccagagc   2040

ggcgcgagcg tggtcgccgg gcctggtttc acaggcggcg acatcattca gtgtacggag   2100

aacggcagcg cggccaccat ctacgtcacg ccggacgtga gctactccca gaagtacaga   2160

gcccgcatcc actacgcctc cacgagccag atcaccttca ccctgagcct cgacggcgcg   2220

cccttcaacc agtactactt cgacaagacc atgaacaagg gcgacacact gacctacaac   2280

agcttcaacc tggctagctt ctctacccca ttcgagctga gcggcaacaa cctgcagatc   2340

ggcgtcacag gcctcagcgc cggcgacaag gtgtacatcg acaagattga gttcatcccg   2400

gtctga                                                              2406
```

<210> SEQ ID NO 18
<211> LENGTH: 801
<212> TYPE: PRT
<213> ORGANISM: Artificial Sequence
<220> FEATURE:
<223> OTHER INFORMATION: TrxA-IP3-1
<220> FEATURE:
<221> NAME/KEY: DOMAIN
<222> LOCATION: (1)...(109)
<223> OTHER INFORMATION: TrxA
<220> FEATURE:
<221> NAME/KEY: DOMAIN
<222> LOCATION: (110)...(158)
<223> OTHER INFORMATION: Linker
<220> FEATURE:
<221> NAME/KEY: DOMAIN
<222> LOCATION: (159)...(801)
<223> OTHER INFORMATION: IP3-1

<400> SEQUENCE: 18

```
Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Asp Lys Met Asn
145                 150                 155                 160

Pro Asn Asn Arg Ser Glu His Asp Thr Ile Lys Thr Thr Glu Asn Asn
                165                 170                 175

Glu Val Pro Thr Asn His Val Gln Tyr Pro Leu Ala Glu Thr Pro Asn
            180                 185                 190
```

```
Pro Thr Leu Glu Asp Leu Asn Tyr Lys Glu Phe Leu Arg Met Thr Ala
        195                 200                 205

Asp Asn Asn Thr Glu Ala Leu Asp Ser Ser Thr Thr Lys Asp Val Ile
    210                 215                 220

Gln Lys Gly Ile Ser Val Val Gly Asp Leu Leu Gly Val Val Gly Phe
225                 230                 235                 240

Pro Phe Gly Gly Ala Leu Val Ser Phe Tyr Thr Asn Phe Leu Asn Thr
                245                 250                 255

Ile Trp Pro Ser Glu Asp Pro Leu Lys Ala Phe Met Glu Gln Val Glu
            260                 265                 270

Ala Leu Ile Asp Gln Lys Ile Ala Asp Tyr Ala Lys Asn Lys Ala Leu
        275                 280                 285

Ala Glu Leu Gln Gly Leu Gln Asn Asn Phe Glu Asp Tyr Val Ser Ala
    290                 295                 300

Leu Ser Ser Trp Gln Lys Asn Pro Val Ser Ser Arg Asn Pro His Ser
305                 310                 315                 320

Gln Gly Arg Ile Arg Glu Leu Phe Ser Gln Ala Glu Ser His Phe Arg
                325                 330                 335

Asn Ser Met Pro Ser Phe Ala Val Ser Gly Tyr Glu Val Leu Phe Leu
            340                 345                 350

Thr Thr Tyr Ala Gln Ala Ala Asn Thr His Leu Leu Leu Leu Lys Asp
        355                 360                 365

Ala Gln Ile Tyr Gly Glu Glu Trp Gly Tyr Glu Lys Glu Asp Ile Ala
    370                 375                 380

Glu Phe Tyr His Arg Gln Leu Lys Leu Thr Gln Glu Tyr Thr Asp His
385                 390                 395                 400

Cys Val Lys Trp Tyr Asn Val Gly Leu Asp Lys Leu Arg Gly Ser Thr
                405                 410                 415

Tyr Glu Ser Trp Val Asn Phe Asn Arg Tyr Arg Arg Glu Met Thr Leu
            420                 425                 430

Thr Val Leu Asp Leu Ile Ala Leu Phe Pro Leu Tyr Asp Val Arg Leu
        435                 440                 445

Tyr Ser Lys Gly Val Lys Thr Glu Leu Thr Arg Asp Val Leu Thr Asp
    450                 455                 460

Pro Ile Val Gly Val Asn Asn Leu Arg Gly Tyr Gly Thr Thr Phe Ser
465                 470                 475                 480

Asn Ile Glu Asn Tyr Ile Arg Lys Pro His Leu Phe Asp Tyr Leu His
                485                 490                 495

Arg Ile Gln Phe His Thr Arg Leu Gln Pro Gly Tyr Tyr Gly Asn Asp
            500                 505                 510

Ser Phe Asn Tyr Trp Ser Gly Asn Tyr Val Ser Thr Arg Pro Ser Ile
        515                 520                 525

Gly Ser Asn Asp Ile Ile Thr Ser Pro Phe Tyr Gly Asn Lys Ser Ser
    530                 535                 540

Glu Pro Val Gln Asn Leu Glu Phe Asn Gly Glu Lys Val Tyr Arg Ala
545                 550                 555                 560

Val Ala Asn Thr Asn Leu Ala Val Trp Pro Ser Ala Val Tyr Ser Gly
                565                 570                 575

Val Thr Lys Val Glu Phe Ser Gln Tyr Asn Asp Gln Thr Asp Glu Ala
            580                 585                 590

Ser Thr Gln Thr Tyr Asp Ser Lys Arg Asn Val Gly Ala Val Ser Trp
        595                 600                 605

Asp Ser Ile Asp Gln Leu Pro Pro Glu Thr Thr Asp Glu Pro Leu Glu
```

```
    610                 615                 620

Lys Ala Tyr Ser His Gln Leu Asn Tyr Val Met Cys Phe Leu Met Gln
625                 630                 635                 640

Gly Ser Arg Gly Thr Ile Pro Val Phe Thr Trp Thr His Lys Ser Val
                645                 650                 655

Asp Phe Phe Asn Thr Ile Asp Ser Lys Lys Ile Thr Gln Leu Pro Leu
            660                 665                 670

Val Lys Ala Tyr Lys Leu Gln Ser Gly Ala Ser Val Val Ala Gly Pro
        675                 680                 685

Gly Phe Thr Gly Gly Asp Ile Ile Gln Cys Thr Glu Asn Gly Ser Ala
    690                 695                 700

Ala Thr Ile Tyr Val Thr Pro Asp Val Ser Tyr Ser Gln Lys Tyr Arg
705                 710                 715                 720

Ala Arg Ile His Tyr Ala Ser Thr Ser Gln Ile Thr Phe Thr Leu Ser
                725                 730                 735

Leu Asp Gly Ala Pro Phe Asn Gln Tyr Tyr Phe Asp Lys Thr Met Asn
            740                 745                 750

Lys Gly Asp Thr Leu Thr Tyr Asn Ser Phe Asn Leu Ala Ser Phe Ser
        755                 760                 765

Thr Pro Phe Glu Leu Ser Gly Asn Asn Leu Gln Ile Gly Val Thr Gly
    770                 775                 780

Leu Ser Ala Gly Asp Lys Val Tyr Ile Asp Lys Ile Glu Phe Ile Pro
785                 790                 795                 800

Val
```

<210> SEQ ID NO 19
<211> LENGTH: 6647
<212> TYPE: DNA
<213> ORGANISM: Artificial Sequence
<220> FEATURE:
<223> OTHER INFORMATION: pMAL-SA vector
<220> FEATURE:
<221> NAME/KEY: misc_feature
<222> LOCATION: (158)...(2631)
<223> OTHER INFORMATION: MBP
<220> FEATURE:
<221> NAME/KEY: misc_feature
<222> LOCATION: (2632)...(2688)
<223> OTHER INFORMATION: SA Linker

<400> SEQUENCE: 19

```
ccgacaccat cgaatggtgc aaaacctttc gcggtatggc atgatagcgc ccggaagaga     60

gtcaattcag ggtggtgaat gtgaaaccag taacgttata cgatgtcgca gagtatgccg    120

gtgtctctta tcagaccgtt tcccgcgtgg tgaaccaggc cagccacgtt tctgcgaaaa    180

cgcgggaaaa agtggaagcg gcgatggcgg agctgaatta cattcccaac cgcgtggcac    240

aacaactggc gggcaaacag tcgttgctga ttggcgttgc cacctccagt ctggccctgc    300

acgcgccgtc gcaaattgtc gcggcgatta aatctcgcgc cgatcaactg ggtgccagcg    360

tggtggtgtc gatggtagaa cgaagcggcg tcgaagcctg taaagcggcg gtgcacaatc    420

ttctcgcgca acgcgtcagt gggctgatca ttaactatcc gctggatgac caggatgcca    480

ttgctgtgga agctgcctgc actaatgttc cggcgttatt tcttgatgtc tctgaccaga    540

cacccatcaa cagtattatt ttctcccatg aagacggtac gcgactgggc gtggagcatc    600

tggtcgcatt gggtcaccag caaatcgcgc tgttagcggg cccattaagt tctgtctcgg    660

cgcgtctgcg tctggctggc tggcataaat atctcactcg caatcaaatt cagccgatag    720
```

-continued

```
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcagta gtgggatacg    900
acgataccga agacagctca tgttatatcc cgccgttaac caccatcaaa caggattttc    960
gcctgctggg gcaaaccagc gtggaccgct tgctgcaact ctctcagggc caggcggtga   1020
agggcaatca gctgttgccc gtctcactgg tgaaaagaaa aaccaccctg gcgcccaata   1080
cgcaaaccgc ctctccccgc gcgttggccg attcattaat gcagctggca cgacaggttt   1140
cccgactgga aagcgggcag tgagcgcaac gcaattaatg tgagttagct cactcattag   1200
gcacaattct catgtttgac agcttatcat cgactgcacg gtgcaccaat gcttctggcg   1260
tcaggcagcc atcggaagct gtggtatggc tgtgcaggtc gtaaatcact gcataattcg   1320
tgtcgctcaa ggcgcactcc cgttctggat aatgtttttt gcgccgacat cataacggtt   1380
ctggcaaata ttctgaaatg agctgttgac aattaatcat cggctcgtat aatgtgtgga   1440
attgtgagcg gataacaatt tcacacagga aacagccagt ccgtttaggt gttttcacga   1500
gcacttcacc aacaaggacc atagcatatg gacaaaatcg aagaaggtaa actggtaatc   1560
tggattaacg gcgataaagg ctataacggt ctcgctgaag tcggtaagaa attcgagaaa   1620
gataccggaa ttaaagtcac cgttgagcat ccggataaac tggaagagaa attcccacag   1680
gttgcggcaa ctggcgatgg ccctgacatt atcttctggg cacacgaccg ctttggtggc   1740
tacgctcaat ctggcctgtt ggctgaaatc accccggaca aagcgttcca ggacaagctg   1800
tatccgttta cctgggatgc cgtacgttac aacggcaagc tgattgctta cccgatcgct   1860
gttgaagcgt tatcgctgat ttataacaaa gatctgctgc cgaacccgcc aaaaacctgg   1920
gaagagatcc cggcgctgga taaagaactg aaagcgaaag gtaagagcgc gctgatgttc   1980
aacctgcaag aaccgtactt cacctggccg ctgattgctg ctgacggggg ttatgcgttc   2040
aagtatgaaa acggcaagta cgacattaaa gacgtgggcg tggataacgc tggcgcgaaa   2100
gcgggtctga ccttcctggt tgacctgatt aaaaacaaac acatgaatgc agacaccgat   2160
tactccatcg cagaagctgc ctttaataaa ggcgaaacag cgatgaccat caacggcccg   2220
tgggcatggt ccaacatcga caccagcaaa gtgaattatg gtgtaacggt actgccgacc   2280
ttcaagggtc aaccatccaa accgttcgtt ggcgtgctga gcgcaggtat taacgccgcc   2340
agtccgaaca aagagctggc aaaagagttc ctcgaaaact atctgctgac tgatgaaggt   2400
ctggaagcgg ttaataaaga caaaccgctg ggtgccgtag cgctgaagtc ttacgaggaa   2460
gagttggcga aagatccacg tattgccgcc actatggaaa acgcccagaa aggtgaaatc   2520
atgccgaaca tcccgcagat gtccgctttc tggtatgccg tgcgtactgc ggtgatcaac   2580
gccgccagcg gtcgtcagac tgtcgatgaa gccctgaaag acgcgcagac tcgtatcacc   2640
aagagcatgt ctgcatctgc atctgcatct gcatctgcat ctgcacgcat gcatcattag   2700
gatcctctag agtcgacctg caggcaagct tggcactggc cgtcgtttta caacgtcgtg   2760
actgggaaaa ccctggcgtt acccaactta atcgccttgc agcacatccc cctttcgcca   2820
gctggcgtaa tagcgaagag gcccgcaccg atcgcccttc ccaacagttg cgcagcctga   2880
atggcgaatg gcagcttggc tgttttggcg gatgagataa gattttcagc ctgatacaga   2940
ttaaatcaga acgcagaagc ggtctgataa aacagaattt gcctggcggc agtagcgcgg   3000
tggtcccacc tgaccccatg ccgaactcag aagtgaaacg ccgtagcgcc gatggtagtg   3060
tggggtctcc ccatgcgaga gtagggaact gccaggcatc aaataaaacg aaaggctcag   3120
```

-continued tcgaaagact gggcctttcg ttttatctgt tgtttgtcgg tgaacgctct cctgagtagg 3180
acaaatccgc cgggagcgga tttgaacgtt gcgaagcaac ggcccggagg gtggcgggca 3240
ggacgcccgc cataaactgc caggcatcaa attaagcaga aggccatcct gacggatggc 3300
ctttttgcgt ttctacaaac tctttttgtt tatttttcta aatacattca aatatgtatc 3360
cgctcatgag acaataaccc tgataaatgc ttcaataata ttgaaaaagg aagagtatga 3420
gtattcaaca tttccgtgtc gcccttattc ccttttttgc ggcattttgc cttcctgttt 3480
ttgctcaccc agaaacgctg gtgaaagtaa aagatgctga agatcagttg ggtgcacgag 3540
tgggttacat cgaactggat ctcaacagcg gtaagatcct tgagagtttt cgccccgaag 3600
aacgttctcc aatgatgagc acttttaaag ttctgctatg tggcgcggta ttatcccgtg 3660
ttgacgccgg gcaagagcaa ctcggtcgcc gcatacacta ttctcagaat gacttggttg 3720
agtactcacc agtcacagaa aagcatctta cggatggcat gacagtaaga gaattatgca 3780
gtgctgccat aaccatgagt gataacactg cggccaactt acttctgaca acgatcggag 3840
gaccgaagga gctaaccgct tttttgcaca acatggggga tcatgtaact cgccttgatc 3900
gttgggaacc ggagctgaat gaagccatac caaacgacga gcgtgacacc acgatgcctg 3960
tagcaatggc aacaacgttg cgcaaactat taactggcga actacttact ctagcttccc 4020
ggcaacaatt aatagactgg atggaggcgg ataaagttgc aggaccactt ctgcgctcgg 4080
cccttccggc tggctggttt attgctgata aatctggagc cggtgagcgt gggtctcgcg 4140
gtatcattgc agcactgggg ccagatggta agccctcccg tatcgtagtt atctacacga 4200
cggggagtca ggcaactatg gatgaacgaa atagacagat cgctgagata ggtgcctcac 4260
tgattaagca ttggtaactg tcagaccaag tttactcata tatactttag attgatttac 4320
cccggttgat aatcagaaaa gccccaaaaa caggaagatt gtataagcaa atatttaaat 4380
tgtaaacgtt aatattttgt taaaattcgc gttaaatttt tgttaaatca gctcattttt 4440
taaccaatag gccgaaatcg gcaaaatccc ttataaatca aaagaataga ccgagatagg 4500
gttgagtgtt gttccagttt ggaacaagag tccactatta aagaacgtgg actccaacgt 4560
caaagggcga aaaaccgtct atcagggcga tggcccacta cgtgaaccat cacccaaatc 4620
aagttttttg gggtcgaggt gccgtaaagc actaaatcgg aaccctaaag ggagcccccg 4680
atttagagct tgacggggaa agccggcgaa cgtggcgaga aaggaaggga agaaagcgaa 4740
aggagcgggc gctagggcgc tggcaagtgt agcggtcacg ctgcgcgtaa ccaccacacc 4800
cgccgcgctt aatgcgccgc tacagggcgc gtaaaaggat ctaggtgaag atcctttttg 4860
ataatctcat gaccaaaatc ccttaacgtg agttttcgtt ccactgagcg tcagaccccg 4920
tagaaaagat caaaggatct tcttgagatc cttttttctc gcgcgtaatc tgctgcttgc 4980
aaacaaaaaa accaccgcta ccagcggtgg tttgtttgcc ggatcaagag ctaccaactc 5040
tttttccgaa ggtaactggc ttcagcagag cgcagatacc aaatactgtc cttctagtgt 5100
agccgtagtt aggccaccac ttcaagaact ctgtagcacc gcctacatac ctcgctctgc 5160
taatcctgtt accagtggct gctgccagtg gcgataagtc gtgtcttacc gggttggact 5220
caagacgata gttaccggat aaggcgcagc ggtcgggctg aacggggggt tcgtgcacac 5280
agcccagctt ggagcgaacg acctacaccg aactgagata cctacagcgt gagctatgag 5340
aaagcgccac gcttcccgaa gggagaaagg cggacaggta tccggtaagc ggcagggtcg 5400
gaacaggaga gcgcacgagg gagcttccag ggggaaacgc ctggtatctt tatagtcctg 5460

```
tcgggtttcg ccacctctga cttgagcgtc gatttttgtg atgctcgtca ggggggcgga   5520

gcctatggaa aaacgccagc aacgcggcct ttttacggtt cctggccttt tgctggcctt   5580

ttgctcacat gttctttcct gcgttatccc ctgattctgt ggataaccgt attaccgcct   5640

ttgagtgagc tgataccgct cgccgcagcc gaacgaccga gcgcagcgag tcagtgagcg   5700

aggaagcgga agagcgcctg atgcggtatt ttctccttac gcatctgtgc ggtatttcac   5760

accgcatata tggtgcactc tcagtacaat ctgctctgat gccgcatagt taagccagta   5820

tacactccgc tatcgctacg tgactgggtc atggctgcgc cccgacaccc gccaacaccc   5880

gctgacgcgc cctgacgggc ttgtctgctc ccggcatccg cttacagaca agctgtgacc   5940

gtctccggga gctgcatgtg tcagaggttt tcaccgtcat caccgaaacg cgcgaggcag   6000

ctgcggtaaa gctcatcagc gtggtcgtgc agcgattcac agatgtctgc ctgttcatcc   6060

gcgtccagct cgttgagttt ctccagaagc gttaatgtct ggcttctgat aaagcgggcc   6120

atgttaaggg cggttttttc ctgtttggtc acttgatgcc tccgtgtaag ggggaatttc   6180

tgttcatggg ggtaatgata ccgatgaaac gagagaggat gctcacgata cgggttactg   6240

atgatgaaca tgcccggtta ctggaacgtt gtgagggtaa acaactggcg gtatggatgc   6300

ggcgggacca gagaaaaatc actcagggtc aatgccagcg cttcgttaat acagatgtag   6360

gtgttccaca gggtagccag cagcatcctg cgatgcagat ccggaacata atggtgcagg   6420

gcgctgactt ccgcgtttcc agactttacg aaacacggaa accgaagacc attcatgttg   6480

ttgctcaggt cgcagacgtt ttgcagcagc agtcgcttca cgttcgctcg cgtatcggtg   6540

attcattctg ctaaccagta aggcaacccc gccagcctag ccgggtcctc aacgacagga   6600

gcacgatcat gcgcacccgt ggccaggacc caacgctgcc cgaaatt                 6647
```

<210> SEQ ID NO 20
<211> LENGTH: 3111
<212> TYPE: DNA
<213> ORGANISM: Artificial Sequence
<220> FEATURE:
<223> OTHER INFORMATION: MBP-IP3-1

<400> SEQUENCE: 20

```
atggacaaaa tcgaagaagg taaactggta atctggatta acggcgataa aggctataac     60

ggtctcgctg aagtcggtaa gaaattcgag aaagataccg gaattaaagt caccgttgag    120

catccggata aactggaaga gaaattccca caggttgcgg caactggcga tggccctgac    180

attatcttct gggcacacga ccgctttggt ggctacgctc aatctggcct gttggctgaa    240

atcaccccgg acaaagcgtt ccaggacaag ctgtatccgt ttacctggga tgccgtacgt    300

tacaacggca agctgattgc ttacccgatc gctgttgaag cgttatcgct gatttataac    360

aaagatctgc tgccgaaccc gccaaaaacc tgggaagaga tcccggcgct ggataaagaa    420

ctgaaagcga aaggtaagag cgcgctgatg ttcaacctgc aagaaccgta cttcacctgg    480

ccgctgattg ctgctgacgg gggttatgcg ttcaagtatg aaaacggcaa gtacgacatt    540

aaagacgtgg gcgtggataa cgctggcgcg aaagcgggtc tgaccttcct ggttgacctg    600

attaaaaaca aacacatgaa tgcagacacc gattactcca tcgcagaagc tgcctttaat    660

aaaggcgaaa cagcgatgac catcaacggc ccgtgggcat ggtccaacat cgacaccagc    720

aaagtgaatt atggtgtaac ggtactgccg accttcaagg gtcaaccatc caaaccgttc    780

gttggcgtgc tgagcgcagg tattaacgcc gccagtccga acaaagagct ggcaaaagag    840

ttcctcgaaa actatctgct gactgatgaa ggtctggaag cggttaataa agacaaaccg    900
```

```
ctgggtgccg tagcgctgaa gtcttacgag gaagagttgg cgaaagatcc acgtattgcc    960
gccactatgg aaaacgccca gaaaggtgaa atcatgccga acatcccgca gatgtccgct   1020
ttctggtatg ccgtgcgtac tgcggtgatc aacgccgcca gcggtcgtca gactgtcgat   1080
gaagccctga aagacgcgca gactaattcg agctcgaaca acaacaacaa taacaataac   1140
aacaacctcg ggatcgaggg aaggatttca gaattaggca tgaaccctaa caacaggtca   1200
gagcacgaca cgatcaagac aaccgagaac aacgaggtgc cgacgaacca cgtccagtac   1260
ccactcgccg aaacaccgaa ccctaccctg gaggacctca actacaagga gttcctgagg   1320
atgacagcgg acaacaacac cgaagccctc gactctagca cgaccaagga cgtgattcag   1380
aagggcatct ctgtggtcgg cgacctgctt ggcgttgtcg ggttcccgtt cggcggcgct   1440
ctcgtcagct tctacacgaa cttcttgaac accatctggc cgtccgaaga ccccctcaag   1500
gcgttcatgg agcaggtgga ggccctcatc gaccagaaga tcgctgacta tgccaagaac   1560
aaggctctgg cggagctgca aggcctgcag aacaacttcg aggactatgt gagcgccctc   1620
agctcttggc agaagaaccc agtcagctcc cgcaacccgc acagccaggg ccgcatcagg   1680
gagctgttca gccaggccga gagccacttc cgcaactcca tgccgagctt cgccgtgagc   1740
ggctacgagg tcctcttcct gactacctat gcccaggctg ccaacaccca cttgcttctc   1800
ctgaaggacg cccagatcta cggcgaagag tggggctacg agaaggagga catcgccgag   1860
ttctaccaca ggcagctcaa gctgacgcag gagtacaccg accactgcgt gaagtggtac   1920
aacgtcggcc ttgacaagct gagagggtct acatacgaga gctgggtcaa cttcaaccgc   1980
tataggcgcg agatgacact taccgtcctc gacctgatcg cgctcttccc tctgtacgac   2040
gtcagacttt actcgaaggg tgtcaagacc gagttgacca gggacgtgct taccgaccca   2100
atcgtcggcg tcaacaacct gcgcggctac gggaccacct tcagcaacat cgagaactac   2160
atcaggaagc cgcacctgtt cgactacctg caccgcattc agttccacac caggctgcag   2220
cccggctact acggcaacga cagcttcaac tactggagcg gcaactacgt gtctaccaga   2280
cccagcatcg gctccaacga catcatcacg tccccgttct acggcaacaa gagcagcgag   2340
ccggtccaga acctggagtt caacggcgag aaggtctatc gcgctgtcgc caacaccaac   2400
ctcgcggtct ggccgagcgc ggtgtacagc ggcgtcacta aggtcgagtt cagccagtac   2460
aacgaccaga ccgacgaggc gtccacgcag acctacgaca gcaagaggaa cgttggcgcc   2520
gtctcctggg acagcatcga ccagctcccg ccagagacca ctgacgagcc acttgagaag   2580
gcttatagcc accagctgaa ctacgtcatg tgcttcctca tgcaaggctc tcgcggcacc   2640
attccggtgt tcacctggac acacaagagc gttgacttct tcaacaccat cgacagcaag   2700
aagatcaccc agctcccgct tgtgaaggcc tacaagctcc agagcggcgc gagcgtggtc   2760
gccgggcctg gtttcacagg cggcgacatc attcagtgta cggagaacgg cagcgcggcc   2820
accatctacg tcacgccgga cgtgagctac tcccagaagt acagagcccg catccactac   2880
gcctccacga gccagatcac cttcaccctg agcctcgacg gcgcgccctt caaccagtac   2940
tacttcgaca agaccatgaa caagggcgac acactgacct acaacagctt caacctggct   3000
agcttctcta ccccattcga gctgagcggc aacaacctgc agatcggcgt cacaggcctc   3060
agcgccggcg acaaggtgta catcgacaag attgagttca tcccggtctg a            3111
```

<210> SEQ ID NO 21
<211> LENGTH: 1036
<212> TYPE: PRT

<213> ORGANISM: Artificial Sequence
<220> FEATURE:
<223> OTHER INFORMATION: MBP-IP3-1
<220> FEATURE:
<221> NAME/KEY: DOMAIN
<222> LOCATION: (1)...(367)
<223> OTHER INFORMATION: MBP
<220> FEATURE:
<221> NAME/KEY: DOMAIN
<222> LOCATION: (368)...(393)
<223> OTHER INFORMATION: Linker
<220> FEATURE:
<221> NAME/KEY: DOMAIN
<222> LOCATION: (394)...(1036)
<223> OTHER INFORMATION: IP3-1

<400> SEQUENCE: 21

```
Met Asp Lys Ile Glu Glu Gly Lys Leu Val Ile Trp Ile Asn Gly Asp
 1               5                  10                  15

Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
        35                  40                  45

Phe Pro Gln Val Ala Ala Thr Gly Asp Gly Pro Asp Ile Ile Phe Trp
    50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
            100                 105                 110

Glu Ala Leu Ser Leu Ile Tyr Asn Lys Asp Leu Leu Pro Asn Pro Pro
        115                 120                 125

Lys Thr Trp Glu Glu Ile Pro Ala Leu Asp Lys Glu Leu Lys Ala Lys
    130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
            180                 185                 190

Gly Leu Thr Phe Leu Val Asp Leu Ile Lys Asn Lys His Met Asn Ala
        195                 200                 205

Asp Thr Asp Tyr Ser Ile Ala Glu Ala Ala Phe Asn Lys Gly Glu Thr
    210                 215                 220

Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
            260                 265                 270

Pro Asn Lys Glu Leu Ala Lys Glu Phe Leu Glu Asn Tyr Leu Leu Thr
        275                 280                 285

Asp Glu Gly Leu Glu Ala Val Asn Lys Asp Lys Pro Leu Gly Ala Val
    290                 295                 300

Ala Leu Lys Ser Tyr Glu Glu Glu Leu Ala Lys Asp Pro Arg Ile Ala
305                 310                 315                 320

Ala Thr Met Glu Asn Ala Gln Lys Gly Glu Ile Met Pro Asn Ile Pro
```

```
                325                 330                 335

Gln Met Ser Ala Phe Trp Tyr Ala Val Arg Thr Ala Val Ile Asn Ala
            340                 345                 350

Ala Ser Gly Arg Gln Thr Val Asp Glu Ala Leu Lys Asp Ala Gln Thr
        355                 360                 365

Asn Ser Ser Ser Asn Asn Asn Asn Asn Asn Asn Asn Asn Asn Leu Gly
    370                 375                 380

Ile Glu Gly Arg Ile Ser Glu Leu Gly Met Asn Pro Asn Asn Arg Ser
385                 390                 395                 400

Glu His Asp Thr Ile Lys Thr Thr Glu Asn Asn Glu Val Pro Thr Asn
                405                 410                 415

His Val Gln Tyr Pro Leu Ala Glu Thr Pro Asn Pro Thr Leu Glu Asp
            420                 425                 430

Leu Asn Tyr Lys Glu Phe Leu Arg Met Thr Ala Asp Asn Asn Thr Glu
        435                 440                 445

Ala Leu Asp Ser Ser Thr Thr Lys Asp Val Ile Gln Lys Gly Ile Ser
    450                 455                 460

Val Val Gly Asp Leu Leu Gly Val Val Gly Phe Pro Phe Gly Gly Ala
465                 470                 475                 480

Leu Val Ser Phe Tyr Thr Asn Phe Leu Asn Thr Ile Trp Pro Ser Glu
                485                 490                 495

Asp Pro Leu Lys Ala Phe Met Glu Gln Val Glu Ala Leu Ile Asp Gln
            500                 505                 510

Lys Ile Ala Asp Tyr Ala Lys Asn Lys Ala Leu Ala Glu Leu Gln Gly
        515                 520                 525

Leu Gln Asn Asn Phe Glu Asp Tyr Val Ser Ala Leu Ser Ser Trp Gln
    530                 535                 540

Lys Asn Pro Val Ser Ser Arg Asn Pro His Ser Gln Gly Arg Ile Arg
545                 550                 555                 560

Glu Leu Phe Ser Gln Ala Glu Ser His Phe Arg Asn Ser Met Pro Ser
                565                 570                 575

Phe Ala Val Ser Gly Tyr Glu Val Leu Phe Leu Thr Thr Tyr Ala Gln
            580                 585                 590

Ala Ala Asn Thr His Leu Leu Leu Leu Lys Asp Ala Gln Ile Tyr Gly
        595                 600                 605

Glu Glu Trp Gly Tyr Glu Lys Glu Asp Ile Ala Glu Phe Tyr His Arg
    610                 615                 620

Gln Leu Lys Leu Thr Gln Glu Tyr Thr Asp His Cys Val Lys Trp Tyr
625                 630                 635                 640

Asn Val Gly Leu Asp Lys Leu Arg Gly Ser Thr Tyr Glu Ser Trp Val
                645                 650                 655

Asn Phe Asn Arg Tyr Arg Arg Glu Met Thr Leu Thr Val Leu Asp Leu
            660                 665                 670

Ile Ala Leu Phe Pro Leu Tyr Asp Val Arg Leu Tyr Ser Lys Gly Val
        675                 680                 685

Lys Thr Glu Leu Thr Arg Asp Val Leu Thr Asp Pro Ile Val Gly Val
    690                 695                 700

Asn Asn Leu Arg Gly Tyr Gly Thr Thr Phe Ser Asn Ile Glu Asn Tyr
705                 710                 715                 720

Ile Arg Lys Pro His Leu Phe Asp Tyr Leu His Arg Ile Gln Phe His
                725                 730                 735

Thr Arg Leu Gln Pro Gly Tyr Tyr Gly Asn Asp Ser Phe Asn Tyr Trp
            740                 745                 750
```

```
Ser Gly Asn Tyr Val Ser Thr Arg Pro Ser Ile Gly Ser Asn Asp Ile
        755                 760                 765

Ile Thr Ser Pro Phe Tyr Gly Asn Lys Ser Ser Glu Pro Val Gln Asn
    770                 775                 780

Leu Glu Phe Asn Gly Glu Lys Val Tyr Arg Ala Val Ala Asn Thr Asn
785                 790                 795                 800

Leu Ala Val Trp Pro Ser Ala Val Tyr Ser Gly Val Thr Lys Val Glu
                805                 810                 815

Phe Ser Gln Tyr Asn Asp Gln Thr Asp Glu Ala Ser Thr Gln Thr Tyr
            820                 825                 830

Asp Ser Lys Arg Asn Val Gly Ala Val Ser Trp Asp Ser Ile Asp Gln
        835                 840                 845

Leu Pro Pro Glu Thr Thr Asp Glu Pro Leu Glu Lys Ala Tyr Ser His
    850                 855                 860

Gln Leu Asn Tyr Val Met Cys Phe Leu Met Gln Gly Ser Arg Gly Thr
865                 870                 875                 880

Ile Pro Val Phe Thr Trp Thr His Lys Ser Val Asp Phe Phe Asn Thr
                885                 890                 895

Ile Asp Ser Lys Lys Ile Thr Gln Leu Pro Leu Val Lys Ala Tyr Lys
            900                 905                 910

Leu Gln Ser Gly Ala Ser Val Val Ala Gly Pro Gly Phe Thr Gly Gly
        915                 920                 925

Asp Ile Ile Gln Cys Thr Glu Asn Gly Ser Ala Ala Thr Ile Tyr Val
    930                 935                 940

Thr Pro Asp Val Ser Tyr Ser Gln Lys Tyr Arg Ala Arg Ile His Tyr
945                 950                 955                 960

Ala Ser Thr Ser Gln Ile Thr Phe Thr Leu Ser Leu Asp Gly Ala Pro
                965                 970                 975

Phe Asn Gln Tyr Tyr Phe Asp Lys Thr Met Asn Lys Gly Asp Thr Leu
            980                 985                 990

Thr Tyr Asn Ser Phe Asn Leu Ala Ser Phe Ser Thr Pro Phe Glu Leu
        995                 1000                1005

Ser Gly Asn Asn Leu Gln Ile Gly Val Thr Gly Leu Ser Ala Gly Asp
    1010                1015                1020

Lys Val Tyr Ile Asp Lys Ile Glu Phe Ile Pro Val
1025                1030                1035


<210> SEQ ID NO 22
<211> LENGTH: 3189
<212> TYPE: DNA
<213> ORGANISM: Artificial Sequence
<220> FEATURE:
<223> OTHER INFORMATION: MBP-RX002

<400> SEQUENCE: 22

atggacaaaa tcgaagaagg taaactggta atctggatta acggcgataa aggctataac     60

ggtctcgctg aagtcggtaa gaaattcgag aaagataccg gaattaaagt caccgttgag    120

catccggata aactggaaga gaaattccca caggttgcgg caactggcga tggccctgac    180

attatcttct gggcacacga ccgctttggt ggctacgctc aatctggcct gttggctgaa    240

atcaccccgg acaaagcgtt ccaggacaag ctgtatccgt ttacctggga tgccgtacgt    300

tacaacggca agctgattgc ttacccgatc gctgttgaag cgttatcgct gatttataac    360

aaagatctgc tgccgaaccc gccaaaaacc tgggaagaga tcccggcgct ggataaagaa    420
```

-continued

```
ctgaaagcga aaggtaagag cgcgctgatg ttcaacctgc aagaaccgta cttcacctgg    480
ccgctgattg ctgctgacgg gggttatgcg ttcaagtatg aaaacggcaa gtacgacatt    540
aaagacgtgg gcgtggataa cgctggcgcg aaagcgggtc tgaccttcct ggttgacctg    600
attaaaaaca aacacatgaa tgcagacacc gattactcca tcgcagaagc tgcctttaat    660
aaaggcgaaa cagcgatgac catcaacggc ccgtgggcat ggtccaacat cgacaccagc    720
aaagtgaatt atggtgtaac ggtactgccg accttcaagg gtcaaccatc caaaccgttc    780
gttggcgtgc tgagcgcagg tattaacgcc gccagtccga acaaagagct ggcaaaagag    840
ttcctcgaaa actatctgct gactgatgaa ggtctggaag cggttaataa agacaaaccg    900
ctgggtgccg tagcgctgaa gtcttacgag gaagagttgg cgaaagatcc acgtattgcc    960
gccactatgg aaaacgccca gaaaggtgaa atcatgccga acatcccgca gatgtccgct   1020
ttctggtatg ccgtgcgtac tgcggtgatc aacgccgcca gcggtcgtca gactgtcgat   1080
gaagccctga aagacgcgca gactaattcg agctcgaaca acaacaacaa taacaataac   1140
aacaacctcg ggatcgaggg aaggatttca gaattaggca tgcgtccaaa taatcaaaat   1200
gaatatgaaa ttatagatac accatctcgt acgtctgtat ctaatgattc tgtcagatat   1260
ccttttgcga atgaaccaac aactgattta aacaatatga attataaaga tttccttaaa   1320
acagtaaatg gttacaatac tggagatctt tctggatctg aagcatttat cagtcaaaca   1380
gcaattagta ctgcaggtaa agctgtgggt acagtactag ggttattggg tgttccatta   1440
gccggagcag ttggcccctt aataaccttc tatggtacca tcgcactatt attctggggg   1500
ccgggagatc catggcaagc ttttatgacc caagtagagg cattagttaa ccaaaaaata   1560
gcagattatg caagaagtaa agcaatctca gaattacaag gattaaggaa tattctcgat   1620
ttatatcgtt cagcacttat agattggcaa gagaacccaa caagaacaag atcagtaaca   1680
aatatccgtt ctcaatttga aactgtaaat aatttttcg aatatcaaat gccatctttt   1740
gcagtggcag gttatgaggt tccattgtta gcagtatatg cacaggcggc aaatcttcat   1800
ttatcaatat taagagatgc cgcgacattc ggagcacaat ggggaatgtc tcaaactgct   1860
attaataaca tatatgacct tcagcagaga agaactgctg agtatactaa tcattgtgtg   1920
aaatggtata ataatggttt agataaatta agaggttcga atgctgggca atgggttaat   1980
tttaatcgct accgtagaga gatgacacta atggtattgg atattgtagc gatatttcca   2040
aactatgata cacgtacgta tccaagtgga attggaacta gtgtccaact tacaagagaa   2100
gtatatacgg atcctattgg ttcgacagca acacaaggtg gcgtttcttg gtatgacgaa   2160
gcaccttctt ttacagctat tgaaagttcc gtggttcgac cacttcactt atttgattta   2220
ctaacaggcg ttacagtcta tgccgctagt agttcttggg attcaagtca ttattttaga   2280
ttttggaatg ggcataaagt agacacaaag ggaattaata gttctattca atatagtaat   2340
gtatatggtt ctactagtaa tgcggttagt acaactacta tatcattttc gggttttgaa   2400
gtttttaaaa ccatttcaat agctggtgta ctatttgctt ggacaacaag gtattttgga   2460
gtccctaaag ttcttttttc taaaatagac cctatttctg gtattggaag ggattcagaa   2520
tttagcgaaa ggtatgcagg gattggagaa caaataaaga attcacttga ggaattacct   2580
ttacaaacag aagatgagcc ggattataaa tcttatagtc ataaattgaa tcatatttca   2640
atggttccac aaactgtacg aacacggaat gtacctgtat tttcttggtc gcatcggagt   2700
gcggatattg acaatagaat ttttcaggat agaattaatc aaattccggt agtaaaggga   2760
catacattag gtccaggtgc ttctgttatg gcaggtcctg gatttacagg aggaaatata   2820
```

```
gttactagaa ccagtccagg tgtagtagtt ttttctggag ttactataaa taacgcatta   2880

tcacaaagat atcgtgtgag aatacggtat gcttctacta ctgacttccg atttttctct   2940

acactttcag gaactcgtct ttatgccact caggctacta aaactatgaa taaaggacaa   3000

caattaacat atgaatcatt tcagtatgca acaattaatt ctacatttac atttgagaat   3060

ataaatgata gtttgacaat aggtgcagat caatttctaa gtggtgagca agtctatgta   3120

gatagatatg aagtaatccc agtggatgca acgtttgagg cggagaacga tttagaggtg   3180

gcaaagtag                                                           3189
```

```
<210> SEQ ID NO 23
<211> LENGTH: 1062
<212> TYPE: PRT
<213> ORGANISM: Artificial Sequence
<220> FEATURE:
<223> OTHER INFORMATION: MBP-RX002
<220> FEATURE:
<221> NAME/KEY: DOMAIN
<222> LOCATION: (1)...(368)
<223> OTHER INFORMATION: MBP
<220> FEATURE:
<221> NAME/KEY: DOMAIN
<222> LOCATION: (369)...(393)
<223> OTHER INFORMATION: Linker
<220> FEATURE:
<221> NAME/KEY: DOMAIN
<222> LOCATION: (394)...(1062)
<223> OTHER INFORMATION: RX002

<400> SEQUENCE: 23

Met Asp Lys Ile Glu Glu Gly Lys Leu Val Ile Trp Ile Asn Gly Asp
 1               5                  10                  15

Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
        35                  40                  45

Phe Pro Gln Val Ala Ala Thr Gly Asp Gly Pro Asp Ile Ile Phe Trp
    50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
            100                 105                 110

Glu Ala Leu Ser Leu Ile Tyr Asn Lys Asp Leu Leu Pro Asn Pro Pro
        115                 120                 125

Lys Thr Trp Glu Glu Ile Pro Ala Leu Asp Lys Glu Leu Lys Ala Lys
    130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
            180                 185                 190

Gly Leu Thr Phe Leu Val Asp Leu Ile Lys Asn Lys His Met Asn Ala
        195                 200                 205

Asp Thr Asp Tyr Ser Ile Ala Glu Ala Ala Phe Asn Lys Gly Glu Thr
    210                 215                 220
```

```
Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
            260                 265                 270

Pro Asn Lys Glu Leu Ala Lys Glu Phe Leu Glu Asn Tyr Leu Leu Thr
        275                 280                 285

Asp Glu Gly Leu Glu Ala Val Asn Lys Asp Lys Pro Leu Gly Ala Val
    290                 295                 300

Ala Leu Lys Ser Tyr Glu Glu Glu Leu Ala Lys Asp Pro Arg Ile Ala
305                 310                 315                 320

Ala Thr Met Glu Asn Ala Gln Lys Gly Glu Ile Met Pro Asn Ile Pro
                325                 330                 335

Gln Met Ser Ala Phe Trp Tyr Ala Val Arg Thr Ala Val Ile Asn Ala
            340                 345                 350

Ala Ser Gly Arg Gln Thr Val Asp Glu Ala Leu Lys Asp Ala Gln Thr
        355                 360                 365

Asn Ser Ser Ser Asn Asn Asn Asn Asn Asn Asn Asn Asn Asn Leu Gly
    370                 375                 380

Ile Glu Gly Arg Ile Ser Glu Leu Gly Met Arg Pro Asn Asn Gln Asn
385                 390                 395                 400

Glu Tyr Glu Ile Ile Asp Thr Pro Ser Arg Thr Ser Val Ser Asn Asp
                405                 410                 415

Ser Val Arg Tyr Pro Phe Ala Asn Glu Pro Thr Thr Asp Leu Asn Asn
            420                 425                 430

Met Asn Tyr Lys Asp Phe Leu Lys Thr Val Asn Gly Tyr Asn Thr Gly
        435                 440                 445

Asp Leu Ser Gly Ser Glu Ala Phe Ile Ser Gln Thr Ala Ile Ser Thr
    450                 455                 460

Ala Gly Lys Ala Val Gly Thr Val Leu Gly Leu Leu Gly Val Pro Leu
465                 470                 475                 480

Ala Gly Ala Val Gly Pro Leu Ile Thr Phe Tyr Gly Thr Ile Ala Leu
                485                 490                 495

Leu Phe Trp Gly Pro Gly Asp Pro Trp Gln Ala Phe Met Thr Gln Val
            500                 505                 510

Glu Ala Leu Val Asn Gln Lys Ile Ala Asp Tyr Ala Arg Ser Lys Ala
        515                 520                 525

Ile Ser Glu Leu Gln Gly Leu Arg Asn Ile Leu Asp Leu Tyr Arg Ser
    530                 535                 540

Ala Leu Ile Asp Trp Gln Glu Asn Pro Thr Arg Thr Arg Ser Val Thr
545                 550                 555                 560

Asn Ile Arg Ser Gln Phe Glu Thr Val Asn Asn Phe Phe Glu Tyr Gln
                565                 570                 575

Met Pro Ser Phe Ala Val Ala Gly Tyr Glu Val Pro Leu Leu Ala Val
            580                 585                 590

Tyr Ala Gln Ala Ala Asn Leu His Leu Ser Ile Leu Arg Asp Ala Ala
        595                 600                 605

Thr Phe Gly Ala Gln Trp Gly Met Ser Gln Thr Ala Ile Asn Asn Ile
    610                 615                 620

Tyr Asp Leu Gln Gln Arg Arg Thr Ala Glu Tyr Thr Asn His Cys Val
625                 630                 635                 640

Lys Trp Tyr Asn Asn Gly Leu Asp Lys Leu Arg Gly Ser Asn Ala Gly
```

```
                645                 650                 655

Gln Trp Val Asn Phe Asn Arg Tyr Arg Arg Glu Met Thr Leu Met Val
            660                 665                 670

Leu Asp Ile Val Ala Ile Phe Pro Asn Tyr Asp Thr Arg Thr Tyr Pro
        675                 680                 685

Ser Gly Ile Gly Thr Ser Val Gln Leu Thr Arg Glu Val Tyr Thr Asp
    690                 695                 700

Pro Ile Gly Ser Thr Ala Thr Gln Gly Gly Val Ser Trp Tyr Asp Glu
705                 710                 715                 720

Ala Pro Ser Phe Thr Ala Ile Glu Ser Ser Val Val Arg Pro Leu His
                725                 730                 735

Leu Phe Asp Leu Leu Thr Gly Val Thr Val Tyr Ala Ala Ser Ser Ser
            740                 745                 750

Trp Asp Ser Ser His Tyr Phe Arg Phe Trp Asn Gly His Lys Val Asp
        755                 760                 765

Thr Lys Gly Ile Asn Ser Ser Ile Gln Tyr Ser Asn Val Tyr Gly Ser
    770                 775                 780

Thr Ser Asn Ala Val Ser Thr Thr Thr Ile Ser Phe Ser Gly Phe Glu
785                 790                 795                 800

Val Phe Lys Thr Ile Ser Ile Ala Gly Val Leu Phe Ala Trp Thr Thr
                805                 810                 815

Arg Tyr Phe Gly Val Pro Lys Val Leu Phe Ser Lys Ile Asp Pro Ile
            820                 825                 830

Ser Gly Ile Gly Arg Asp Ser Glu Phe Ser Glu Arg Tyr Ala Gly Ile
        835                 840                 845

Gly Glu Gln Ile Lys Asn Ser Leu Glu Glu Leu Pro Leu Gln Thr Glu
    850                 855                 860

Asp Glu Pro Asp Tyr Lys Ser Tyr Ser His Lys Leu Asn His Ile Ser
865                 870                 875                 880

Met Val Pro Gln Thr Val Arg Thr Arg Asn Val Pro Val Phe Ser Trp
                885                 890                 895

Ser His Arg Ser Ala Asp Ile Asp Asn Arg Ile Phe Gln Asp Arg Ile
            900                 905                 910

Asn Gln Ile Pro Val Val Lys Gly His Thr Leu Gly Pro Gly Ala Ser
        915                 920                 925

Val Met Ala Gly Pro Gly Phe Thr Gly Gly Asn Ile Val Thr Arg Thr
    930                 935                 940

Ser Pro Gly Val Val Val Phe Ser Gly Val Thr Ile Asn Asn Ala Leu
945                 950                 955                 960

Ser Gln Arg Tyr Arg Val Arg Ile Arg Tyr Ala Ser Thr Thr Asp Phe
                965                 970                 975

Arg Phe Phe Ser Thr Leu Ser Gly Thr Arg Leu Tyr Ala Thr Gln Ala
            980                 985                 990

Thr Lys Thr Met Asn Lys Gly Gln Gln Leu Thr Tyr Glu Ser Phe Gln
        995                 1000                1005

Tyr Ala Thr Ile Asn Ser Thr Phe Thr Phe Glu Asn Ile Asn Asp Ser
    1010                1015                1020

Leu Thr Ile Gly Ala Asp Gln Phe Leu Ser Gly Glu Gln Val Tyr Val
1025                1030                1035                1040

Asp Arg Tyr Glu Val Ile Pro Val Asp Ala Thr Phe Glu Ala Glu Asn
                1045                1050                1055

Asp Leu Glu Val Ala Lys
            1060
```

<210> SEQ ID NO 24
<211> LENGTH: 3228
<212> TYPE: DNA
<213> ORGANISM: Artificial Sequence
<220> FEATURE:
<223> OTHER INFORMATION: MBP-2A-12

<400> SEQUENCE: 24

```
atggacaaaa tcgaagaagg taaactggta atctggatta acggcgataa aggctataac     60
ggtctcgctg aagtcggtaa gaaattcgag aaagataccg gaattaaagt caccgttgag    120
catccggata aactggaaga gaaattccca caggttgcgg caactggcga tggccctgac    180
attatcttct gggcacacga ccgctttggt ggctacgctc aatctggcct gttggctgaa    240
atcaccccgg acaaagcgtt ccaggacaag ctgtatccgt ttacctggga tgccgtacgt    300
tacaacggca agctgattgc ttacccgatc gctgttgaag cgttatcgct gatttataac    360
aaagatctgc tgccgaaccc gccaaaaacc tgggaagaga tcccggcgct ggataaagaa    420
ctgaaagcga aaggtaagag cgcgctgatg ttcaacctgc aagaaccgta cttcacctgg    480
ccgctgattg ctgctgacgg gggttatgcg ttcaagtatg aaaacggcaa gtacgacatt    540
aaagacgtgg gcgtggataa cgctggcgcg aaagcgggtc tgaccttcct ggttgacctg    600
attaaaaaca aacacatgaa tgcagacacc gattactcca tcgcagaagc tgcctttaat    660
aaaggcgaaa cagcgatgac catcaacggc ccgtgggcat ggtccaacat cgacaccagc    720
aaagtgaatt atggtgtaac ggtactgccg accttcaagg gtcaaccatc caaaccgttc    780
gttggcgtgc tgagcgcagg tattaacgcc gccagtccga acaaagagct ggcaaaagag    840
ttcctcgaaa actatctgct gactgatgaa ggtctggaag cggttaataa agacaaaccg    900
ctgggtgccg tagcgctgaa gtcttacgag gaagagttgg cgaaagatcc acgtattgcc    960
gccactatgg aaaacgccca gaaaggtgaa atcatgccga acatcccgca gatgtccgct   1020
ttctggtatg ccgtgcgtac tgcggtgatc aacgccgcca gcggtcgtca gactgtcgat   1080
gaagccctga aagacgcgca gactaattcg agctcgaaca acaacaacaa taacaataac   1140
aacaacctcg ggatcgaggg aaggatttca gaattaggca tgcgaatgag tccaaataat   1200
caaaatgaat atgaaattat agatgcgaca ccttctactt ctgtatccaa tgattctaac   1260
agataccctt ttgcgaatga gccaacaaat gcgctacaaa atatggatta taaagattat   1320
ttaaaaatgt ctgcgggaaa tgctagtgaa taccctggtt cacctgaagt acttgtcagc   1380
ggacaagatg cagctaaggc cgcaattgat atagtaggta aattactatc aggtttaggg   1440
gtcccatttg ttgggccgat agtgagtctt tatactcaac ttattgatat tctgtggcct   1500
tcagggcaaa agagtcaatg ggagattttt atggaacaag tagaagaact cataaatcaa   1560
aaaatagcag aatatgcaag gaataaagcg ctttcggaat tagaaggatt aggtaataat   1620
taccaattat atctaaccgc gcttgaagaa tggaaagaaa atccatttcg tagaggattt   1680
agaagaggtg ccttacgaga tgcgcgaaat cgatttgaaa tcctggatag tttatttacg   1740
caatatatgc catcttttag agtgacaaat tttgaagtac cattccttac tgtatatgca   1800
atggcagcca accttcattt actgttatta aaggacgcgt caatttttgg agaagaatgg   1860
ggatggtcaa caactactat taataactat tatgatcgtc aaatgaaact tactgcagaa   1920
tattctgatc actgtgtaaa gtggtatgaa actggtttag caaaattaaa aggcacgagc   1980
gctaaacaat gggtcgacta caaccaattc cgtagagaaa tgacactgac ggttttagat   2040
```

```
gttgttgcat tattcccaaa ttatgacaca cgcacgtacc caatggaaac gaaagcacaa   2100

ctaacaaggg aagtatatac agatccactg ggcgcggtaa acgtgtcttc aattggttcc   2160

tggtatgaca aagcaccttc tttcggagtg atagaatcat ccgttattcg accaccccat   2220

gtatttgatt atataacggg actcacagtg tatacacaat caagaagcat ttcttccgct   2280

cgctatataa gacattgggc tggtcatcaa ataagctacc atcgtgtcag taggggtagt   2340

aatcttcaac aaatgtatgg aactaatcaa aatctacaca gcaccagtac ctttgatttt   2400

acgaattatg atatttacaa gacgttatca aaagatgcgg tgctccttga tattgttttt   2460

cctggttata cgtatatatt ttttggaatg ccagaagtcg agtttttcat ggtaaaccaa   2520

ttgaataata ccagaaagac gttaaagtat aatccggttt ccaaagatat tatagcgggg   2580

acaagagatt cggaattaga attgcctcca gaaacttcag atcaaccaaa ttatgagtca   2640

aatagccata gattatgtca tatcacaagt attcccgcga cgggtaacac taccggatta   2700

gtgcctgtat tttcttggac acatcgaagt gcagatttaa acaatacaat atattcagat   2760

aaaatcactc aaattccggc cgttaaatgt tgggataatt taccgtttgt tccagtggta   2820

aaaggaccag gacatacagg aggggattta ttacagtata atagaagtac tggttctgta   2880

ggaaccttat ttctagctcg atatggccta gcattagaaa aagcaggaaa atatcgtgta   2940

agactgagat atgctactga tgcagatatt gtattgcatg taaacgatgc tcagattcag   3000

atgccaaaaa caatgaaccc aggtgaggat ctgacatcta aaacttttaa agttgcagat   3060

gctatcacaa cagttaattt agcaacagat agttcggttg cagttaaaca taatgttggt   3120

gaagacccta attcaacagt ttctggtata gtttacgttg accgaatcga attcatccca   3180

gtagatgaga catatgaagc ggaacaagat ttagaagcgg ccaaatga                 3228
```

```
<210> SEQ ID NO 25
<211> LENGTH: 1075
<212> TYPE: PRT
<213> ORGANISM: Artificial Sequence
<220> FEATURE:
<223> OTHER INFORMATION: MBP-2A-12
<220> FEATURE:
<221> NAME/KEY: DOMAIN
<222> LOCATION: (1)...(368)
<223> OTHER INFORMATION: MBP
<220> FEATURE:
<221> NAME/KEY: DOMAIN
<222> LOCATION: (369)...(393)
<223> OTHER INFORMATION: Linker
<220> FEATURE:
<221> NAME/KEY: DOMAIN
<222> LOCATION: (394)...(1075)
<223> OTHER INFORMATION: 2A-12

<400> SEQUENCE: 25

Met Asp Lys Ile Glu Glu Gly Lys Leu Val Ile Trp Ile Asn Gly Asp
 1               5                  10                  15

Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
        35                  40                  45

Phe Pro Gln Val Ala Ala Thr Gly Asp Gly Pro Asp Ile Ile Phe Trp
    50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95
```

```
Asp Ala Val Arg Tyr Asn Gly Lys Leu Ile Ala Tyr Pro Ile Ala Val
            100                 105                 110

Glu Ala Leu Ser Leu Ile Tyr Asn Lys Asp Leu Leu Pro Asn Pro Pro
        115                 120                 125

Lys Thr Trp Glu Glu Ile Pro Ala Leu Asp Lys Glu Leu Lys Ala Lys
    130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
            180                 185                 190

Gly Leu Thr Phe Leu Val Asp Leu Ile Lys Asn Lys His Met Asn Ala
        195                 200                 205

Asp Thr Asp Tyr Ser Ile Ala Glu Ala Ala Phe Asn Lys Gly Glu Thr
    210                 215                 220

Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
            260                 265                 270

Pro Asn Lys Glu Leu Ala Lys Glu Phe Leu Glu Asn Tyr Leu Leu Thr
        275                 280                 285

Asp Glu Gly Leu Glu Ala Val Asn Lys Asp Lys Pro Leu Gly Ala Val
    290                 295                 300

Ala Leu Lys Ser Tyr Glu Glu Glu Leu Ala Lys Asp Pro Arg Ile Ala
305                 310                 315                 320

Ala Thr Met Glu Asn Ala Gln Lys Gly Glu Ile Met Pro Asn Ile Pro
                325                 330                 335

Gln Met Ser Ala Phe Trp Tyr Ala Val Arg Thr Ala Val Ile Asn Ala
            340                 345                 350

Ala Ser Gly Arg Gln Thr Val Asp Glu Ala Leu Lys Asp Ala Gln Thr
        355                 360                 365

Asn Ser Ser Ser Asn Asn Asn Asn Asn Asn Asn Asn Asn Asn Leu Gly
    370                 375                 380

Ile Glu Gly Arg Ile Ser Glu Leu Gly Met Arg Met Ser Pro Asn Asn
385                 390                 395                 400

Gln Asn Glu Tyr Glu Ile Ile Asp Ala Thr Pro Ser Thr Ser Val Ser
                405                 410                 415

Asn Asp Ser Asn Arg Tyr Pro Phe Ala Asn Glu Pro Thr Asn Ala Leu
            420                 425                 430

Gln Asn Met Asp Tyr Lys Asp Tyr Leu Lys Met Ser Ala Gly Asn Ala
        435                 440                 445

Ser Glu Tyr Pro Gly Ser Pro Glu Val Leu Val Ser Gly Gln Asp Ala
    450                 455                 460

Ala Lys Ala Ala Ile Asp Ile Val Gly Lys Leu Leu Ser Gly Leu Gly
465                 470                 475                 480

Val Pro Phe Val Gly Pro Ile Val Ser Leu Tyr Thr Gln Leu Ile Asp
                485                 490                 495

Ile Leu Trp Pro Ser Gly Gln Lys Ser Gln Trp Glu Ile Phe Met Glu
            500                 505                 510
```

```
Gln Val Glu Glu Leu Ile Asn Gln Lys Ile Ala Glu Tyr Ala Arg Asn
        515                 520                 525

Lys Ala Leu Ser Glu Leu Glu Gly Leu Gly Asn Asn Tyr Gln Leu Tyr
    530                 535                 540

Leu Thr Ala Leu Glu Glu Trp Lys Glu Asn Pro Phe Arg Arg Gly Phe
545                 550                 555                 560

Arg Arg Gly Ala Leu Arg Asp Ala Arg Asn Arg Phe Glu Ile Leu Asp
                565                 570                 575

Ser Leu Phe Thr Gln Tyr Met Pro Ser Phe Arg Val Thr Asn Phe Glu
            580                 585                 590

Val Pro Phe Leu Thr Val Tyr Ala Met Ala Ala Asn Leu His Leu Leu
        595                 600                 605

Leu Leu Lys Asp Ala Ser Ile Phe Gly Glu Glu Trp Gly Trp Ser Thr
    610                 615                 620

Thr Thr Ile Asn Asn Tyr Tyr Asp Arg Gln Met Lys Leu Thr Ala Glu
625                 630                 635                 640

Tyr Ser Asp His Cys Val Lys Trp Tyr Glu Thr Gly Leu Ala Lys Leu
                645                 650                 655

Lys Gly Thr Ser Ala Lys Gln Trp Val Asp Tyr Asn Gln Phe Arg Arg
            660                 665                 670

Glu Met Thr Leu Thr Val Leu Asp Val Val Ala Leu Phe Pro Asn Tyr
        675                 680                 685

Asp Thr Arg Thr Tyr Pro Met Glu Thr Lys Ala Gln Leu Thr Arg Glu
    690                 695                 700

Val Tyr Thr Asp Pro Leu Gly Ala Val Asn Val Ser Ser Ile Gly Ser
705                 710                 715                 720

Trp Tyr Asp Lys Ala Pro Ser Phe Gly Val Ile Glu Ser Ser Val Ile
                725                 730                 735

Arg Pro Pro His Val Phe Asp Tyr Ile Thr Gly Leu Thr Val Tyr Thr
            740                 745                 750

Gln Ser Arg Ser Ile Ser Ser Ala Arg Tyr Ile Arg His Trp Ala Gly
        755                 760                 765

His Gln Ile Ser Tyr His Arg Val Ser Arg Gly Ser Asn Leu Gln Gln
    770                 775                 780

Met Tyr Gly Thr Asn Gln Asn Leu His Ser Thr Ser Thr Phe Asp Phe
785                 790                 795                 800

Thr Asn Tyr Asp Ile Tyr Lys Thr Leu Ser Lys Asp Ala Val Leu Leu
                805                 810                 815

Asp Ile Val Phe Pro Gly Tyr Thr Tyr Ile Phe Phe Gly Met Pro Glu
            820                 825                 830

Val Glu Phe Phe Met Val Asn Gln Leu Asn Asn Thr Arg Lys Thr Leu
        835                 840                 845

Lys Tyr Asn Pro Val Ser Lys Asp Ile Ile Ala Gly Thr Arg Asp Ser
    850                 855                 860

Glu Leu Glu Leu Pro Pro Glu Thr Ser Asp Gln Pro Asn Tyr Glu Ser
865                 870                 875                 880

Asn Ser His Arg Leu Cys His Ile Thr Ser Ile Pro Ala Thr Gly Asn
                885                 890                 895

Thr Thr Gly Leu Val Pro Val Phe Ser Trp Thr His Arg Ser Ala Asp
            900                 905                 910

Leu Asn Asn Thr Ile Tyr Ser Asp Lys Ile Thr Gln Ile Pro Ala Val
        915                 920                 925

Lys Cys Trp Asp Asn Leu Pro Phe Val Pro Val Val Lys Gly Pro Gly
```

```
    930                 935                 940

His Thr Gly Gly Asp Leu Leu Gln Tyr Asn Arg Ser Thr Gly Ser Val
945                 950                 955                 960

Gly Thr Leu Phe Leu Ala Arg Tyr Gly Leu Ala Leu Glu Lys Ala Gly
                965                 970                 975

Lys Tyr Arg Val Arg Leu Arg Tyr Ala Thr Asp Ala Asp Ile Val Leu
            980                 985                 990

His Val Asn Asp Ala Gln Ile Gln Met Pro Lys Thr Met Asn Pro Gly
        995                 1000                1005

Glu Asp Leu Thr Ser Lys Thr Phe Lys Val Ala Asp Ala Ile Thr Thr
    1010                1015                1020

Val Asn Leu Ala Thr Asp Ser Ser Val Ala Val Lys His Asn Val Gly
1025                1030                1035                1040

Glu Asp Pro Asn Ser Thr Val Ser Gly Ile Val Tyr Val Asp Arg Ile
                1045                1050                1055

Glu Phe Ile Pro Val Asp Glu Thr Tyr Glu Ala Glu Gln Asp Leu Glu
            1060                1065                1070

Ala Ala Lys
        1075
```

<210> SEQ ID NO 26
<211> LENGTH: 3153
<212> TYPE: DNA
<213> ORGANISM: Artificial Sequence
<220> FEATURE:
<223> OTHER INFORMATION: MBP-4c6

<400> SEQUENCE: 26

```
atggacaaaa tcgaagaagg taaactggta atctggatta acggcgataa aggctataac     60

ggtctcgctg aagtcggtaa gaaattcgag aaagataccg gaattaaagt caccgttgag    120

catccggata aactggaaga gaaattccca caggttgcgg caactggcga tggccctgac    180

attatcttct gggcacacga ccgctttggt ggctacgctc aatctggcct gttggctgaa    240

atcaccccgg acaaagcgtt ccaggacaag ctgtatccgt ttacctggga tgccgtacgt    300

tacaacggca agctgattgc ttacccgatc gctgttgaag cgttatcgct gatttataac    360

aaagatctgc tgccgaaccc gccaaaaacc tgggaagaga tcccggcgct ggataaagaa    420

ctgaaagcga aaggtaagag cgcgctgatg ttcaacctgc aagaaccgta cttcacctgg    480

ccgctgattg ctgctgacgg gggttatgcg ttcaagtatg aaaacggcaa gtacgacatt    540

aaagacgtgg gcgtggataa cgctggcgcg aaagcgggtc tgaccttcct ggttgacctg    600

attaaaaaca aacacatgaa tgcagacacc gattactcca tcgcagaagc tgcctttaat    660

aaaggcgaaa cagcgatgac catcaacggc ccgtgggcat ggtccaacat cgacaccagc    720

aaagtgaatt atggtgtaac ggtactgccg accttcaagg gtcaaccatc caaaccgttc    780

gttggcgtgc tgagcgcagg tattaacgcc gccagtccga acaaagagct ggcaaaagag    840

ttcctcgaaa actatctgct gactgatgaa ggtctggaag cggttaataa agacaaaccg    900

ctgggtgccg tagcgctgaa gtcttacgag gaagagttgg cgaaagatcc acgtattgcc    960

gccactatgg aaaacgccca gaaaggtgaa atcatgccga acatcccgca gatgtccgct   1020

ttctggtatg ccgtgcgtac tgcggtgatc aacgccgcca gcggtcgtca gactgtcgat   1080

gaagccctga aagacgcgca gactaattcg agctcgaaca acaacaacaa taacaataac   1140

aacaacctcg ggatcgaggg aaggatttca gaattaggca tgacttcaaa taggaaaaat   1200
```

```
gagaatgaaa ttataaatgc cttatcgatt ccagctgtat cgaatcattc cgcacaaatg   1260

gatctatcgc tagatgctcg tattgaggat tctttgtgta tagccgaggg gaataatatc   1320

aatccacttg ttagcgcatc aacagtccaa acgggtataa acatagctgg tagaatattg   1380

ggcgtattag gtgtgccgtt tgctggacaa ctagctagtt tttatagttt tcttgttggg   1440

gaattatggc ctagtggcag agatccatgg gaaattttcc tggaacatgt agaacaactt   1500

ataagacaac aagtaacaga aaatactagg aatacggcta ttgctcgatt agaaggtcta   1560

ggaaaaggct atagatctta ccagcaggct cttgaaactt ggttagataa ccgaaatgat   1620

gcaagatcaa gaagcattat tcttgagcgc tatgttgctt tagaacttga cattactact   1680

gctataccgc ttttcagaat acgaaatgaa gaagttccat tattaatggt atatgctcaa   1740

gctgcaaatt tacacctatt attattgaga gacgcatccc tttttggtag tgaatggggg   1800

atggcatctt ccgatgttaa ccaatattac caagaacaaa tcaggtatac agaggaatat   1860

tctaaccatt gcgtacaatg gtataataca gggctaaata acttaagagg gacaaatgct   1920

gaaagttggc tgcggtataa tcaattccgt agagacctaa cgttaggggt attagattta   1980

gtagccctat tcccaagcta tgatactcgc acttatccaa tcaatacgag tgctcagtta   2040

acaagagaaa tttatacaga tccaattggg agaacaaatg caccttcagg atttgcaagt   2100

acgaattggt ttaataataa tgcaccatcg ttttctgcca tagaggctgc cattttcagg   2160

cctccgcatc tacttgattt tccagaacaa cttacaattt acagtgcatc aagccgttgg   2220

agtagcactc aacatatgaa ttattgggtg ggacataggc ttaacttccg cccaatagga   2280

gggacattaa atacctcaac acaaggactt actaataata cttcaattaa tcctgtaaca   2340

ttacagttta cgtctcgtga cgtttataga acagaatcaa atgcagggac aaatatacta   2400

tttactactc ctgtgaatgg agtaccttgg gctagattta attttataaa ccctcagaat   2460

atttatgaaa gaggcgccac tacctacagt caaccgtatc agggagttgg gattcaatta   2520

tttgattcag aaactgaatt accaccagaa acaacagaac gaccaaatta tgaatcatat   2580

agtcatagat tatctcatat aggactaatc ataggaaaca ctttgagagc accagtctat   2640

tcttggacgc atcgtagtgc agatcgtacg aatacgattg gaccaaatag aattactcaa   2700

attcctgcag tgaagggaag atttcttttt aatggttctg taatttcagg accaggattt   2760

actggtggag acgtagttag attgaatagg aataatggta atattcaaaa tagagggtat   2820

attgaagttc caattcaatt cacgtcgaca tctaccagat atcgagttcg agtacgttat   2880

gcttctgtaa cctcgattga gctcaatgtt aatttgggca attcatcaat ttttacgaac   2940

acattaccag caacagctgc atcattagat aatctacaat caggggattt tggttatgtt   3000

gaaatcaaca atgcttttac atccgcaaca ggtaatatag taggtgctag aaattttagt   3060

gcaaatgcag aagtaataat agacagattt gaatttatcc cagttactgc aaccttcgag   3120

gcagaatatg atttagaaag agcacaaaag tga                                 3153
```

<210> SEQ ID NO 27
<211> LENGTH: 1050
<212> TYPE: PRT
<213> ORGANISM: Artificial Sequence
<220> FEATURE:
<223> OTHER INFORMATION: MBP-4c6
<220> FEATURE:
<221> NAME/KEY: DOMAIN
<222> LOCATION: (1)...(368)
<223> OTHER INFORMATION: MBP
<220> FEATURE:
<221> NAME/KEY: DOMAIN
<222> LOCATION: (369)...(393)
<223> OTHER INFORMATION: Linker
<220> FEATURE:
<221> NAME/KEY: DOMAIN
<222> LOCATION: (394)...(1050)
<223> OTHER INFORMATION: 4c6

<400> SEQUENCE: 27

```
Met Asp Lys Ile Glu Glu Gly Lys Leu Val Ile Trp Ile Asn Gly Asp
 1               5                  10                  15

Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
        35                  40                  45

Phe Pro Gln Val Ala Ala Thr Gly Asp Gly Pro Asp Ile Ile Phe Trp
    50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
            100                 105                 110

Glu Ala Leu Ser Leu Ile Tyr Asn Lys Asp Leu Leu Pro Asn Pro Pro
        115                 120                 125

Lys Thr Trp Glu Glu Ile Pro Ala Leu Asp Lys Glu Leu Lys Ala Lys
    130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
            180                 185                 190

Gly Leu Thr Phe Leu Val Asp Leu Ile Lys Asn Lys His Met Asn Ala
        195                 200                 205

Asp Thr Asp Tyr Ser Ile Ala Glu Ala Ala Phe Asn Lys Gly Glu Thr
    210                 215                 220

Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
            260                 265                 270

Pro Asn Lys Glu Leu Ala Lys Glu Phe Leu Glu Asn Tyr Leu Leu Thr
        275                 280                 285

Asp Glu Gly Leu Glu Ala Val Asn Lys Asp Lys Pro Leu Gly Ala Val
    290                 295                 300

Ala Leu Lys Ser Tyr Glu Glu Glu Leu Ala Lys Asp Pro Arg Ile Ala
305                 310                 315                 320

Ala Thr Met Glu Asn Ala Gln Lys Gly Glu Ile Met Pro Asn Ile Pro
                325                 330                 335

Gln Met Ser Ala Phe Trp Tyr Ala Val Arg Thr Ala Val Ile Asn Ala
            340                 345                 350

Ala Ser Gly Arg Gln Thr Val Asp Glu Ala Leu Lys Asp Ala Gln Thr
        355                 360                 365

Asn Ser Ser Ser Asn Asn Asn Asn Asn Asn Asn Asn Asn Asn Leu Gly
```

```
    370                 375                 380

Ile Glu Gly Arg Ile Ser Glu Leu Gly Met Thr Ser Asn Arg Lys Asn
385                 390                 395                 400

Glu Asn Glu Ile Ile Asn Ala Leu Ser Ile Pro Ala Val Ser Asn His
                405                 410                 415

Ser Ala Gln Met Asp Leu Ser Leu Asp Ala Arg Ile Glu Asp Ser Leu
            420                 425                 430

Cys Ile Ala Glu Gly Asn Asn Ile Asn Pro Leu Val Ser Ala Ser Thr
        435                 440                 445

Val Gln Thr Gly Ile Asn Ile Ala Gly Arg Ile Leu Gly Val Leu Gly
    450                 455                 460

Val Pro Phe Ala Gly Gln Leu Ala Ser Phe Tyr Ser Phe Leu Val Gly
465                 470                 475                 480

Glu Leu Trp Pro Ser Gly Arg Asp Pro Trp Glu Ile Phe Leu Glu His
                485                 490                 495

Val Glu Gln Leu Ile Arg Gln Gln Val Thr Glu Asn Thr Arg Asn Thr
            500                 505                 510

Ala Ile Ala Arg Leu Glu Gly Leu Gly Lys Gly Tyr Arg Ser Tyr Gln
        515                 520                 525

Gln Ala Leu Glu Thr Trp Leu Asp Asn Arg Asn Asp Ala Arg Ser Arg
    530                 535                 540

Ser Ile Ile Leu Glu Arg Tyr Val Ala Leu Glu Leu Asp Ile Thr Thr
545                 550                 555                 560

Ala Ile Pro Leu Phe Arg Ile Arg Asn Glu Glu Val Pro Leu Leu Met
                565                 570                 575

Val Tyr Ala Gln Ala Ala Asn Leu His Leu Leu Leu Leu Arg Asp Ala
            580                 585                 590

Ser Leu Phe Gly Ser Glu Trp Gly Met Ala Ser Ser Asp Val Asn Gln
        595                 600                 605

Tyr Tyr Gln Glu Gln Ile Arg Tyr Thr Glu Glu Tyr Ser Asn His Cys
    610                 615                 620

Val Gln Trp Tyr Asn Thr Gly Leu Asn Asn Leu Arg Gly Thr Asn Ala
625                 630                 635                 640

Glu Ser Trp Leu Arg Tyr Asn Gln Phe Arg Arg Asp Leu Thr Leu Gly
                645                 650                 655

Val Leu Asp Leu Val Ala Leu Phe Pro Ser Tyr Asp Thr Arg Thr Tyr
            660                 665                 670

Pro Ile Asn Thr Ser Ala Gln Leu Thr Arg Glu Ile Tyr Thr Asp Pro
        675                 680                 685

Ile Gly Arg Thr Asn Ala Pro Ser Gly Phe Ala Ser Thr Asn Trp Phe
    690                 695                 700

Asn Asn Asn Ala Pro Ser Phe Ser Ala Ile Glu Ala Ala Ile Phe Arg
705                 710                 715                 720

Pro Pro His Leu Leu Asp Phe Pro Glu Gln Leu Thr Ile Tyr Ser Ala
                725                 730                 735

Ser Ser Arg Trp Ser Ser Thr Gln His Met Asn Tyr Trp Val Gly His
            740                 745                 750

Arg Leu Asn Phe Arg Pro Ile Gly Gly Thr Leu Asn Thr Ser Thr Gln
        755                 760                 765

Gly Leu Thr Asn Asn Thr Ser Ile Asn Pro Val Thr Leu Gln Phe Thr
    770                 775                 780

Ser Arg Asp Val Tyr Arg Thr Glu Ser Asn Ala Gly Thr Asn Ile Leu
785                 790                 795                 800
```

```
Phe Thr Thr Pro Val Asn Gly Val Pro Trp Ala Arg Phe Asn Phe Ile
                805                 810                 815

Asn Pro Gln Asn Ile Tyr Glu Arg Gly Ala Thr Thr Tyr Ser Gln Pro
            820                 825                 830

Tyr Gln Gly Val Gly Ile Gln Leu Phe Asp Ser Glu Thr Glu Leu Pro
        835                 840                 845

Pro Glu Thr Thr Glu Arg Pro Asn Tyr Glu Ser Tyr Ser His Arg Leu
    850                 855                 860

Ser His Ile Gly Leu Ile Ile Gly Asn Thr Leu Arg Ala Pro Val Tyr
865                 870                 875                 880

Ser Trp Thr His Arg Ser Ala Asp Arg Thr Asn Thr Ile Gly Pro Asn
                885                 890                 895

Arg Ile Thr Gln Ile Pro Ala Val Lys Gly Arg Phe Leu Phe Asn Gly
            900                 905                 910

Ser Val Ile Ser Gly Pro Gly Phe Thr Gly Gly Asp Val Val Arg Leu
        915                 920                 925

Asn Arg Asn Asn Gly Asn Ile Gln Asn Arg Gly Tyr Ile Glu Val Pro
    930                 935                 940

Ile Gln Phe Thr Ser Thr Ser Thr Arg Tyr Arg Val Arg Val Arg Tyr
945                 950                 955                 960

Ala Ser Val Thr Ser Ile Glu Leu Asn Val Asn Leu Gly Asn Ser Ser
                965                 970                 975

Ile Phe Thr Asn Thr Leu Pro Ala Thr Ala Ala Ser Leu Asp Asn Leu
            980                 985                 990

Gln Ser Gly Asp Phe Gly Tyr Val Glu Ile Asn Asn Ala Phe Thr Ser
        995                 1000                1005

Ala Thr Gly Asn Ile Val Gly Ala Arg Asn Phe Ser Ala Asn Ala Glu
    1010                1015                1020

Val Ile Ile Asp Arg Phe Glu Phe Ile Pro Val Thr Ala Thr Phe Glu
1025                1030                1035                1040

Ala Glu Tyr Asp Leu Glu Arg Ala Gln Lys
                1045                1050


<210> SEQ ID NO 28
<211> LENGTH: 25
<212> TYPE: PRT
<213> ORGANISM: Artificial Sequence
<220> FEATURE:
<223> OTHER INFORMATION: NEB pMAL Linker

<400> SEQUENCE: 28

Asn Ser Ser Ser Asn Asn Asn Asn Asn Asn Asn Asn Asn Asn Leu Gly
 1               5                  10                  15

Ile Glu Gly Arg Ile Ser Glu Leu Gly
            20                  25


<210> SEQ ID NO 29
<211> LENGTH: 19
<212> TYPE: PRT
<213> ORGANISM: Artificial Sequence
<220> FEATURE:
<223> OTHER INFORMATION: SA Linker

<400> SEQUENCE: 29

Arg Ile Thr Lys Ser Met Ser Ala Ser Ala Ser Ala Ser Ala Ser Ala
 1               5                  10                  15

Ser Ala Arg
```

<210> SEQ ID NO 30
<211> LENGTH: 51
<212> TYPE: PRT
<213> ORGANISM: Artificial Sequence
<220> FEATURE:
<223> OTHER INFORMATION: NusA Linker

<400> SEQUENCE: 30

```
Thr Ser Gly Ser Gly His His His His His His Ser Ala Gly Lys Glu
 1               5                  10                  15

Thr Ala Ala Ala Lys Phe Glu Arg Gln His Met Asp Ser Pro Pro Pro
            20                  25                  30

Thr Gly Leu Val Pro Arg Gly Ser Ala Gly Ser Gly Thr Ile Asp Asp
        35                  40                  45

Asp Asp Lys
    50
```

<210> SEQ ID NO 31
<211> LENGTH: 49
<212> TYPE: PRT
<213> ORGANISM: Artificial Sequence
<220> FEATURE:
<223> OTHER INFORMATION: TrxA Linker

<400> SEQUENCE: 31

```
Gly Ser Gly Ser Gly His Met His His His His His His Ser Ser Gly
 1               5                  10                  15

Leu Val Pro Arg Gly Ser Gly Met Lys Glu Thr Ala Ala Ala Lys Phe
            20                  25                  30

Glu Arg Gln His Met Asp Ser Pro Asp Leu Gly Thr Asp Asp Asp Asp
        35                  40                  45

Lys
```

<210> SEQ ID NO 32
<211> LENGTH: 3174
<212> TYPE: DNA
<213> ORGANISM: Artificial Sequence
<220> FEATURE:
<223> OTHER INFORMATION: MBP-SA-RX002

<400> SEQUENCE: 32

```
atggacaaga tcgaggaggg caagctcgtg atctggatca acggcgacaa gggctacaac     60

ggcctcgccg aggtcggcaa gaagttcgag aaggacaccg gcatcaaggt gaccgtcgag    120

cacccggaca agctggagga gaagttcccc caggtggctg cgaccggcga cggcccggac    180

attatcttct gggcccacga caggttcggc ggatacgccc agagcggcct tctcgctgag    240

atcacgccag acaaggcctt ccaggacaag ctgtatccat tcacttggga cgctgtccgc    300

tacaacggca agctgatcgc ctaccccatc gctgtggagg cactgtcact gatctacaac    360

aaggacctcc ttcctaaccc accgaagacg tgggaggaga tcccagcgct ggacaaggag    420

ctcaaggcga agggcaagtc cgcgctgatg ttcaacctgc aagaaccgta cttcacctgg    480

cctctgattg ccgctgacgg cggctacgcc ttcaagtacg agaacgggaa gtacgacatc    540

aaggacgtcg gcgtcgacaa cgctggcgcc aaggccgggc tcacattcct tgtggacctg    600

atcaagaaca agcacatgaa cgccgacacg gactactcta tcgctgaggc tgccttcaac    660

aaaggggaga cagccatgac catcaacggc ccctgggcct ggagcaacat cgacaccagc    720

aaggtcaact acggcgtgac cgtcctccct acgttcaagg gccagccgtc caagccattc    780
```

```
gttggcgtgc tgagcgccgg catcaacgcg gcctccccca acaaggagct cgcgaaagag    840
ttcctggaga actacctgct cactgacgag ggcctggagg cggtcaacaa ggacaagccg    900
cttggcgccg tcgctctgaa gtcttacgag gaggagctgg ccaaggaccc taggatcgcc    960
gctacgatgg agaacgccca gaagggcgag atcatgccca acatcccgca gatgtccgcg   1020
ttctggtatg cggtgcgcac tgccgtcatc aacgctgcca gcggcaggca gaccgttgac   1080
gaggcgctta aggacgcgca gaccaggatc acgaagtcta tgagcgcctc tgcttcagcc   1140
tccgcgagcg cctccgctag gagcatgcgc ccgaacaacc agaacgagta cgagatcatc   1200
gacaccccat cccgcacgtc cgtctccaac gactccgtcc gctacccgtt cgcgaacgag   1260
ccgactaccg atctgaacaa catgaactac aaggacttcc tgaagaccgt gaatggctac   1320
aacaccggcg acctgtccgg gtccgaggcg tttatctccc agacggcgat atctacagcc   1380
ggcaaggcgg tcggcaccgt tctcggactg ctcggcgtcc cgctggctgg ggctgtcggc   1440
ccgttgatca ccttctacgg cacgatcgca ctcctcttct ggggacccgg cgacccttgg   1500
caggctttca tgactcaggt cgaggccctc gttaaccaga agatcgccga ttacgccagg   1560
tcaaaggcca tatccgagct gcaggggctc cgtaacatct tggacctcta ccgttcagcg   1620
ctcatcgact ggcaggagaa cccgacacgc accaggtccg tgaccaacat aagatctcag   1680
ttcgagactg ttaataactt cttcgaatac cagatgccgt ccttcgccgt cgcggggtac   1740
gaggtcccgt tgctcgcagt gtacgcgcag gccgcgaacc tccacctcag cattctgagg   1800
gacgcagcca ctttcggcgc ccaatggggt atgagccaaa ccgccatcaa caacatatac   1860
gacctgcagc agcgtaggac ggccgagtac accaaccact gcgtcaagtg gtacaataat   1920
ggcctcgaca agctccgtgg cagcaacgcc ggacagtggg tcaacttcaa ccgctatcgc   1980
agggagatga ccctcatggt cctcgacatt gtcgccattt tcccgaacta cgacacgcgg   2040
acctacccgt ccgggattgg aacctctgtg cagctgacca gggaggtcta cacggacccg   2100
ataggctcca ctgcgacaca aggtggtgtc tcctggtacg acgaggcccc gagcttcaca   2160
gccatcgagt cctccgtggt ccggccgctt cacctgttcg accttcttac cggcgtcacc   2220
gtctacgccg ccagctccag ctgggactcc agccattact tcaggttctg gaatgggcac   2280
aaagtggaca ccaagggcat caactcgtcc atccagtact ccaacgttta cggctctacg   2340
agcaacgctg tctccacgac caccatttcg ttcagcggtt tcgaggtgtt caagaccatc   2400
tccattgccg gtgtcctgtt cgcctggacg accaggtact tcggggtccc gaaggtcctc   2460
ttctccaaga tcgaccctat ctcgggaatc ggcagggact cagagttcag cgaaaggtat   2520
gctgggatcg gcgagcagat taagaactca ctcgaggagc tgcccctgca aaccgaggac   2580
gagccggact acaagtccta ctcccacaaa ctcaaccaca tctccatggt cccgcagaca   2640
gtccgtacca ggaacgtccc ggtgttctcc tggtcccacc ggtccgccga catagacaac   2700
cgtatcttcc aggacaggat caaccagatc ccggttgtca agggacacac actcggaccg   2760
ggcgcttccg tcatggctgg cccgggcttc accggcggca acatagtgac taggacatct   2820
ccgggcgtgg ttgtgttctc cggtgtcacc atcaataacg ctctgtctca gaggtaccgc   2880
gtcaggatac gctacgccag cacgaccgac ttccgtttct tctcgactct ctccggtacc   2940
aggctgtacg ccacccaggc gacgaagacg atgaacaagg gccagcagct cacgtacgaa   3000
tccttccagt acgccacaat caacagtacc ttcacgttcg aaaacatcaa cgactccctc   3060
actatcggcg ccgaccagtt ccttagcggc gagcaagtct acgtggaccg ctacgaggtt   3120
```

```
atccccgtcg acgcgacctt cgaggccgag aacgacctgg aggtcgcgaa atga        3174


<210> SEQ ID NO 33
<211> LENGTH: 1057
<212> TYPE: PRT
<213> ORGANISM: Artificial Sequence
<220> FEATURE:
<223> OTHER INFORMATION: MBP-SA-RX002

<400> SEQUENCE: 33

Met Asp Lys Ile Glu Glu Gly Lys Leu Val Ile Trp Ile Asn Gly Asp
1               5                   10                  15

Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
        35                  40                  45

Phe Pro Gln Val Ala Ala Thr Gly Asp Gly Pro Asp Ile Ile Phe Trp
    50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
            100                 105                 110

Glu Ala Leu Ser Leu Ile Tyr Asn Lys Asp Leu Leu Pro Asn Pro Pro
        115                 120                 125

Lys Thr Trp Glu Glu Ile Pro Ala Leu Asp Lys Glu Leu Lys Ala Lys
    130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
            180                 185                 190

Gly Leu Thr Phe Leu Val Asp Leu Ile Lys Asn Lys His Met Asn Ala
        195                 200                 205

Asp Thr Asp Tyr Ser Ile Ala Glu Ala Ala Phe Asn Lys Gly Glu Thr
    210                 215                 220

Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
            260                 265                 270

Pro Asn Lys Glu Leu Ala Lys Glu Phe Leu Glu Asn Tyr Leu Leu Thr
        275                 280                 285

Asp Glu Gly Leu Glu Ala Val Asn Lys Asp Lys Pro Leu Gly Ala Val
    290                 295                 300

Ala Leu Lys Ser Tyr Glu Glu Glu Leu Ala Lys Asp Pro Arg Ile Ala
305                 310                 315                 320

Ala Thr Met Glu Asn Ala Gln Lys Gly Glu Ile Met Pro Asn Ile Pro
                325                 330                 335

Gln Met Ser Ala Phe Trp Tyr Ala Val Arg Thr Ala Val Ile Asn Ala
            340                 345                 350

Ala Ser Gly Arg Gln Thr Val Asp Glu Ala Leu Lys Asp Ala Gln Thr
```

```
        355                 360                 365

Arg Ile Thr Lys Ser Met Ser Ala Ser Ala Ser Ala Ser Ala Ser Ala
    370                 375                 380

Ser Ala Arg Ser Met Arg Pro Asn Asn Gln Asn Glu Tyr Glu Ile Ile
385                 390                 395                 400

Asp Thr Pro Ser Arg Thr Ser Val Ser Asn Asp Ser Val Arg Tyr Pro
                405                 410                 415

Phe Ala Asn Glu Pro Thr Thr Asp Leu Asn Asn Met Asn Tyr Lys Asp
            420                 425                 430

Phe Leu Lys Thr Val Asn Gly Tyr Asn Thr Gly Asp Leu Ser Gly Ser
        435                 440                 445

Glu Ala Phe Ile Ser Gln Thr Ala Ile Ser Thr Ala Gly Lys Ala Val
    450                 455                 460

Gly Thr Val Leu Gly Leu Leu Gly Val Pro Leu Ala Gly Ala Val Gly
465                 470                 475                 480

Pro Leu Ile Thr Phe Tyr Gly Thr Ile Ala Leu Leu Phe Trp Gly Pro
                485                 490                 495

Gly Asp Pro Trp Gln Ala Phe Met Thr Gln Val Glu Ala Leu Val Asn
            500                 505                 510

Gln Lys Ile Ala Asp Tyr Ala Arg Ser Lys Ala Ile Ser Glu Leu Gln
        515                 520                 525

Gly Leu Arg Asn Ile Leu Asp Leu Tyr Arg Ser Ala Leu Ile Asp Trp
    530                 535                 540

Gln Glu Asn Pro Thr Arg Thr Arg Ser Val Thr Asn Ile Arg Ser Gln
545                 550                 555                 560

Phe Glu Thr Val Asn Asn Phe Phe Glu Tyr Gln Met Pro Ser Phe Ala
                565                 570                 575

Val Ala Gly Tyr Glu Val Pro Leu Leu Ala Val Tyr Ala Gln Ala Ala
            580                 585                 590

Asn Leu His Leu Ser Ile Leu Arg Asp Ala Ala Thr Phe Gly Ala Gln
        595                 600                 605

Trp Gly Met Ser Gln Thr Ala Ile Asn Asn Ile Tyr Asp Leu Gln Gln
    610                 615                 620

Arg Arg Thr Ala Glu Tyr Thr Asn His Cys Val Lys Trp Tyr Asn Asn
625                 630                 635                 640

Gly Leu Asp Lys Leu Arg Gly Ser Asn Ala Gly Gln Trp Val Asn Phe
                645                 650                 655

Asn Arg Tyr Arg Arg Glu Met Thr Leu Met Val Leu Asp Ile Val Ala
            660                 665                 670

Ile Phe Pro Asn Tyr Asp Thr Arg Thr Tyr Pro Ser Gly Ile Gly Thr
        675                 680                 685

Ser Val Gln Leu Thr Arg Glu Val Tyr Thr Asp Pro Ile Gly Ser Thr
    690                 695                 700

Ala Thr Gln Gly Gly Val Ser Trp Tyr Asp Glu Ala Pro Ser Phe Thr
705                 710                 715                 720

Ala Ile Glu Ser Ser Val Val Arg Pro Leu His Leu Phe Asp Leu Leu
                725                 730                 735

Thr Gly Val Thr Val Tyr Ala Ala Ser Ser Ser Trp Asp Ser Ser His
            740                 745                 750

Tyr Phe Arg Phe Trp Asn Gly His Lys Val Asp Thr Lys Gly Ile Asn
        755                 760                 765

Ser Ser Ile Gln Tyr Ser Asn Val Tyr Gly Ser Thr Ser Asn Ala Val
    770                 775                 780
```

```
Ser Thr Thr Thr Ile Ser Phe Ser Gly Phe Glu Val Phe Lys Thr Ile
785                 790                 795                 800

Ser Ile Ala Gly Val Leu Phe Ala Trp Thr Thr Arg Tyr Phe Gly Val
                805                 810                 815

Pro Lys Val Leu Phe Ser Lys Ile Asp Pro Ile Ser Gly Ile Gly Arg
            820                 825                 830

Asp Ser Glu Phe Ser Glu Arg Tyr Ala Gly Ile Gly Glu Gln Ile Lys
        835                 840                 845

Asn Ser Leu Glu Glu Leu Pro Leu Gln Thr Glu Asp Glu Pro Asp Tyr
    850                 855                 860

Lys Ser Tyr Ser His Lys Leu Asn His Ile Ser Met Val Pro Gln Thr
865                 870                 875                 880

Val Arg Thr Arg Asn Val Pro Val Phe Ser Trp Ser His Arg Ser Ala
                885                 890                 895

Asp Ile Asp Asn Arg Ile Phe Gln Asp Arg Ile Asn Gln Ile Pro Val
            900                 905                 910

Val Lys Gly His Thr Leu Gly Pro Gly Ala Ser Val Met Ala Gly Pro
        915                 920                 925

Gly Phe Thr Gly Gly Asn Ile Val Thr Arg Thr Ser Pro Gly Val Val
    930                 935                 940

Val Phe Ser Gly Val Thr Ile Asn Asn Ala Leu Ser Gln Arg Tyr Arg
945                 950                 955                 960

Val Arg Ile Arg Tyr Ala Ser Thr Thr Asp Phe Arg Phe Phe Ser Thr
                965                 970                 975

Leu Ser Gly Thr Arg Leu Tyr Ala Thr Gln Ala Thr Lys Thr Met Asn
            980                 985                 990

Lys Gly Gln Gln Leu Thr Tyr Glu Ser Phe Gln Tyr Ala Thr Ile Asn
        995                 1000                1005

Ser Thr Phe Thr Phe Glu Asn Ile Asn Asp Ser Leu Thr Ile Gly Ala
    1010                1015                1020

Asp Gln Phe Leu Ser Gly Glu Gln Val Tyr Val Asp Arg Tyr Glu Val
1025                1030                1035                1040

Ile Pro Val Asp Ala Thr Phe Glu Ala Glu Asn Asp Leu Glu Val Ala
                1045                1050                1055

Lys
```

<210> SEQ ID NO 34
<211> LENGTH: 368
<212> TYPE: PRT
<213> ORGANISM: Escherichia coli
<220> FEATURE:
<221> NAME/KEY: DOMAIN
<222> LOCATION: (1)...(368)
<223> OTHER INFORMATION: MBP

<400> SEQUENCE: 34

```
Met Asp Lys Ile Glu Glu Gly Lys Leu Val Ile Trp Ile Asn Gly Asp
 1               5                  10                  15

Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
        35                  40                  45

Phe Pro Gln Val Ala Ala Thr Gly Asp Gly Pro Asp Ile Ile Phe Trp
    50                  55                  60

Ala His Asp Arg Phe Gly Gly Tyr Ala Gln Ser Gly Leu Leu Ala Glu
```

```
65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
            100                 105                 110

Glu Ala Leu Ser Leu Ile Tyr Asn Lys Asp Leu Leu Pro Asn Pro Pro
        115                 120                 125

Lys Thr Trp Glu Glu Ile Pro Ala Leu Asp Lys Glu Leu Lys Ala Lys
    130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
            180                 185                 190

Gly Leu Thr Phe Leu Val Asp Leu Ile Lys Asn Lys His Met Asn Ala
        195                 200                 205

Asp Thr Asp Tyr Ser Ile Ala Glu Ala Ala Phe Asn Lys Gly Glu Thr
    210                 215                 220

Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
            260                 265                 270

Pro Asn Lys Glu Leu Ala Lys Glu Phe Leu Glu Asn Tyr Leu Leu Thr
        275                 280                 285

Asp Glu Gly Leu Glu Ala Val Asn Lys Asp Lys Pro Leu Gly Ala Val
    290                 295                 300

Ala Leu Lys Ser Tyr Glu Glu Glu Leu Ala Lys Asp Pro Arg Ile Ala
305                 310                 315                 320

Ala Thr Met Glu Asn Ala Gln Lys Gly Glu Ile Met Pro Asn Ile Pro
                325                 330                 335

Gln Met Ser Ala Phe Trp Tyr Ala Val Arg Thr Ala Val Ile Asn Ala
            340                 345                 350

Ala Ser Gly Arg Gln Thr Val Asp Glu Ala Leu Lys Asp Ala Gln Thr
        355                 360                 365


<210> SEQ ID NO 35
<211> LENGTH: 495
<212> TYPE: PRT
<213> ORGANISM: Escherichia coli
<220> FEATURE:
<221> NAME/KEY: DOMAIN
<222> LOCATION: (1)...(495)
<223> OTHER INFORMATION: NusA

<400> SEQUENCE: 35

Met Asn Lys Glu Ile Leu Ala Val Val Glu Ala Val Ser Asn Glu Lys
 1               5                  10                  15

Ala Leu Pro Arg Glu Lys Ile Phe Glu Ala Leu Glu Ser Ala Leu Ala
            20                  25                  30

Thr Ala Thr Lys Lys Lys Tyr Glu Gln Glu Ile Asp Val Arg Val Gln
        35                  40                  45

Ile Asp Arg Lys Ser Gly Asp Phe Asp Thr Phe Arg Arg Trp Leu Val
    50                  55                  60
```

```
Val Asp Glu Val Thr Gln Pro Thr Lys Glu Ile Thr Leu Glu Ala Ala
65                  70                  75                  80

Arg Tyr Glu Asp Glu Ser Leu Asn Leu Gly Asp Tyr Val Glu Asp Gln
                85                  90                  95

Ile Glu Ser Val Thr Phe Asp Arg Ile Thr Thr Gln Thr Ala Lys Gln
            100                 105                 110

Val Ile Val Gln Lys Val Arg Glu Ala Glu Arg Ala Met Val Val Asp
        115                 120                 125

Gln Phe Arg Glu His Glu Gly Glu Ile Ile Thr Gly Val Val Lys Lys
    130                 135                 140

Val Asn Arg Asp Asn Ile Ser Leu Asp Leu Gly Asn Asn Ala Glu Ala
145                 150                 155                 160

Val Ile Leu Arg Glu Asp Met Leu Pro Arg Glu Asn Phe Arg Pro Gly
                165                 170                 175

Asp Arg Val Arg Gly Val Leu Tyr Ser Val Arg Pro Glu Ala Arg Gly
            180                 185                 190

Ala Gln Leu Phe Val Thr Arg Ser Lys Pro Glu Met Leu Ile Glu Leu
        195                 200                 205

Phe Arg Ile Glu Val Pro Glu Ile Gly Glu Glu Val Ile Glu Ile Lys
    210                 215                 220

Ala Ala Ala Arg Asp Pro Gly Ser Arg Ala Lys Ile Ala Val Lys Thr
225                 230                 235                 240

Asn Asp Lys Arg Ile Asp Pro Val Gly Ala Cys Val Gly Met Arg Gly
                245                 250                 255

Ala Arg Val Gln Ala Val Ser Thr Glu Leu Gly Gly Glu Arg Ile Asp
            260                 265                 270

Ile Val Leu Trp Asp Asp Asn Pro Ala Gln Phe Val Ile Asn Ala Met
        275                 280                 285

Ala Pro Ala Asp Val Ala Ser Ile Val Val Asp Glu Asp Lys His Thr
    290                 295                 300

Met Asp Ile Ala Val Glu Ala Gly Asn Leu Ala Gln Ala Ile Gly Arg
305                 310                 315                 320

Asn Gly Gln Asn Val Arg Leu Ala Ser Gln Leu Ser Gly Trp Glu Leu
                325                 330                 335

Asn Val Met Thr Val Asp Asp Leu Gln Ala Lys His Gln Ala Glu Ala
            340                 345                 350

His Ala Ala Ile Asp Thr Phe Thr Lys Tyr Leu Asp Ile Asp Glu Asp
        355                 360                 365

Phe Ala Thr Val Leu Val Glu Glu Gly Phe Ser Thr Leu Glu Glu Leu
    370                 375                 380

Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
            420                 425                 430

Asp Leu Leu Asn Leu Glu Gly Val Asp Arg Asp Leu Ala Phe Lys Leu
        435                 440                 445

Ala Ala Arg Gly Val Cys Thr Leu Glu Asp Leu Ala Glu Gln Gly Ile
    450                 455                 460

Asp Asp Leu Ala Asp Ile Glu Gly Leu Thr Asp Glu Lys Ala Gly Ala
465                 470                 475                 480
```

```
Leu Ile Met Ala Ala Arg Asn Ile Cys Trp Phe Gly Asp Glu Ala
                485                 490                 495


<210> SEQ ID NO 36
<211> LENGTH: 109
<212> TYPE: PRT
<213> ORGANISM: Escherichia coli
<220> FEATURE:
<221> NAME/KEY: DOMAIN
<222> LOCATION: (1)...(109)
<223> OTHER INFORMATION: TrxA

<400> SEQUENCE: 36

Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105
```

METHODS AND COMPOSITIONS TO ENHANCE ACTIVITY OF CRY ENDOTOXINS

CROSS REFERENCE TO RELATED APPLICATIONS

This application claims the benefit U.S. Provisional Application No. 61/713,844, filed Oct. 15, 2012, which is incorporated he rein by reference in their entirety.

REFERENCE TO SEQUENCE LISTING SUBMITTED ELECTRONICALLY

An official copy of the Sequence Listing submitted electronically as an ASCII formatted Sequence Listing with a file named "3113PCT_SequenceListing.txt," created on Sep. 17, 2013, having a size of 158 kb and filed concurrently with the Specification is part of the Specification and is incorporated herein by reference as if set forth in its entirety.

FIELD OF THE INVENTION

The invention relates generally to plant molecular biology and plant pest control, and more particularly to compositions and methods for enhancing the activity of pesticidal polypeptides from *Bacillus* spp. and for protecting a plant from a plant pest, particularly an insect pest.

BACKGROUND OF THE INVENTION

Pests, such as insect pests, are a major factor in the loss of the world's agricultural crops. For example, corn rootworm and boll weevil damage can be economically devastating to agricultural producers. Insect pest-related agricultural crop loss from corn rootworm alone has reached one billion dollars a year.

Traditionally, the primary methods for controlling insect pests, such as corn rootworm, are crop rotation and application of broad-spectrum, synthetic, chemical pesticides. However, consumers and government regulators alike are becoming increasingly concerned with environmental hazards associated with producing and using chemical pesticides. Because of such concerns, regulators have banned or limited the use of some of the more hazardous chemical pesticides. Thus, there is substantial interest in developing alternatives to chemical pesticides that present a lower risk of pollution and environmental hazards and that provide a greater target specificity than is characteristic of chemical pesticides.

Certain species in the genus *Bacillus* have polypeptides that possess pesticidal activity against a broad range of insect pests including those in the orders Lepidoptera, Diptera, Coleoptera, Hemiptera and others. For example, *Bacillus thuringiensis* and *Bacillus popilliae* are among the most successful species discovered to date having pesticidal activity. Such pesticidal activity also has been attributed to strains of *Bacillus larvae, Bacillus lentimorbus, Bacillus sphaericus* and *Bacillus cereus*. See, *Biotechnology Handbook* 2: *Bacillus* (Harwood ed., Plenum Press 1989); and Int'l Patent Application Publication No. WO 96/10083.

Pesticidal polypeptides from *Bacillus* spp. include the crystal (Cry) endotoxins, cytolytic (Cyt) endotoxins, vegetative proteins (VIPs) and the like. See, e.g., Bravo et al. (2007) *Toxicon* 49:423-435. The Cry endotoxins (also called δ-endotoxins) have been isolated from various strains of *B. thuringiensis*. A common characteristic of the Cry endotoxins is their expression during the stationary phase of growth, as they generally accumulate in a mother cell compartment to form a crystal inclusion that can account for 23-30% of the dry weight of sporulated cells. The Cry endotoxins initially are produced in an inactive protoxin form, which are proteolytically converted into an active endotoxin through the action of proteases in an insect's gut. Once active, the endotoxins bind to the gut epithelium and form cation-selective channels that cause cell lysis and subsequent death. See, Carroll et al. (1997) *J. Invertebr. Pathol.* 70:41-49; Oppert (1999) *Arch. Insect Biochem. Phys.* 42:1-12; and Rukmini et al. (2000) *Biochimie* 82:109-116.

Although Cry endotoxins often are highly effective against insect pests, some insect pests are not affected by them or show low susceptibility. Likewise, some insect pests have developed resistance to the Cry endotoxins, which threatens their effectiveness. Methods to address these problems include enhancing or expanding Cry endotoxin activity by site-directed mutagenesis, by introducing cleavage sites in specific regions of the endotoxin or by deleting small fragments from the amino-terminus of the endotoxin. See, e.g., Abdullah & Dean (2004) *Appl. Environ. Microbiol.* 70:3769-3771; Pardo-López et al. (2009) *Peptides* 30:589-595; Rajamohan et al. (1996) *Proc. Natl. Acad. Sci. USA* 93:14338-14343; and Wu et al. (2000) *FEBS Lett.* 473 227-232. These methods, however, can be time consuming and not certain to produce a desired result.

For the foregoing reasons, there is a need for compositions and methods to enhance the pesticidal activity of Cry endotoxins.

BRIEF SUMMARY OF THE INVENTION

Compositions and methods are provided for enhancing pesticidal activity of Cry endotoxins and for protecting a plant from plant pest such as insect pests. The compositions comprise chimeric pesticidal polypeptide-encoding nucleic acid molecules, variants and fragments thereof, as well as chimeric pesticidal polypeptides, active variants and fragments thereof. The chimeric pesticidal polypeptides of the invention comprise a solubility-enhancing polypeptide fused to a Cry endotoxin or biologically active fragment thereof. Also provided are expression cassettes or polynucleotide constructs comprising a nucleotide sequence encoding a chimeric pesticidal polypeptide of the invention, as well as bacteria, plants, plant organs, plants tissues, plant parts, plant cells and seeds comprising the expression cassette or polynucleotide nucleotide construct encoding the chimeric pesticidal polypeptide. Further provided are pesticidal compositions comprising at least one chimeric pesticidal polypeptide of the invention.

Methods are provided for enhancing the pesticidal activity of Cry endotoxins. The methods involve making a chimeric pesticidal polypeptide comprising the amino acid sequence of a solubility-enhancing polypeptide operably linked to an amino acid sequence of a Cry endotoxin or biologically active fragment thereof. Such chimeric pesticidal polypeptide can be produced by fusing amino acid sequence of the solubility-enhancing polypeptide to the amino acid sequence of a Cry endotoxin or biologically active fragment thereof. Alternatively, the methods involve making a polynucleotide construct comprising a nucleotide sequence encoding the chimeric pesticidal polypeptide and transforming an organism or non-human host cell of interest with the polynucleotide construct for expression of the chimeric pesticidal polypeptide. The nucleotide sequence encoding the chimeric pesticidal polypeptide can be produced by, for example, operably linking a nucleotide sequence encoding a solubility-enhancing polypeptide to a nucleotide sequence encoding a Cry endotoxin or biologically active fragment thereof. Typically, the polynucleotide construct further comprises a promoter that drives expression in the organism or host cell, wherein the promoter is operably linked to the nucleotide sequence encoding the chimeric pesticidal polypeptide.

Thus, methods are provided for producing a polynucleotide construct comprising a nucleotide sequence encoding a chimeric pesticidal polypeptide, which comprises an amino acid sequence of solubility-enhancing polypeptide fused to an amino acid sequence of a Cry endotoxin or biologically active fragment thereof. The methods involve operably linking a nucleotide sequence encoding solubility-enhancing polypeptide to a nucleotide sequence encoding a Cry endotoxin or biologically active fragment thereof. The polynucleotide construct may additional comprise an operably linked promoter for expression of the chimeric pesticidal polypeptide in a non-human host cell of interest, particularly a plant cell. Such a polynucleotide construct finds use, for example, in methods for expressing the chimeric pesticidal polypeptide in a plant transformed therewith.

The present invention further provides methods for making plants with enhanced resistance to at least one pest. The methods involved transforming a plant or at least one plant cell with a polynucleotide construct comprising a nucleotide sequence encoding a chimeric pesticidal polypeptide of the invention. Typically, the nucleotide sequence encoding a chimeric pesticidal polypeptide will be operably linked to a promoter that drives expression in a plant cell. The methods can further involve regenerating the plant or the at least one plant cell into a transformed plant, wherein the regenerated plant expresses the chimeric pesticidal polypeptide. Such a transformed plant comprises enhanced resistance to at least one plant pest, particularly an insect pest, when compared to the resistance of a control plant.

The methods also involve applying a composition such as a pesticidal composition comprising the chimeric pesticidal polypeptide or active variant or fragment thereof, to the environment of an insect pest, particularly on or in the vicinity of a plant by, for example, spraying, dusting, broadcasting or seed coating to protect the plant from the insect pest.

Further provided are transformed plants, plant cells and other host cells, and seeds comprising a nucleotide sequence encoding the chimeric pesticidal polypeptide of the invention.

The following embodiments are encompassed by the present invention:

1. A method of enhancing pesticidal activity of a Cry endotoxin, the method comprising operably linking a first amino acid sequence of a solubility-enhancing polypeptide to a second amino acid sequence of a Cry endotoxin, whereby a chimeric pesticidal polypeptide is produced, the chimeric pesticidal polypeptide comprising the first amino acid sequence operably linked to second amino acid sequence.

2. The method of embodiment 1, wherein the solubility-enhancing polypeptide is selected from the group consisting of a maltose-binding protein (MBP), a thioredoxin, a transcription elongation factor NusA, a glutathione-S-transferase (GST), a mistic, a small ubiquitin-related modifier (SUMO), a protein disulfide isomerase DsbC, and a thiol: disulfide interchange protein DsbD.

3. The method of embodiment 1 or 2, wherein the solubility-enhancing polypeptide is a MBP.

4. The method of embodiment 3, wherein the MBP is selected from the group consisting of MBPs having an accession number set forth in Table 1.

5. The method of embodiment 1 or 2, wherein the solubility-enhancing protein is NusA.

6. The method of embodiment 1 or 2, wherein the solubility-enhancing protein is thioredoxin.

7. The method of embodiment 1, wherein the solubility-enhancing polypeptide comprises an amino acid sequence selected from the group consisting of the amino acid sequences set forth in SEQ ID NOS: 4, 6, 34, 35, and 36.

8. The method of any one of embodiments 1-7, wherein the Cry endotoxin is selected from the group consisting of Cry endotoxins set forth in Table 2.

9. The method of any one of embodiments 1-8, wherein the Cry endotoxin comprises an amino acid sequence selected from the group consisting of SEQ ID NOS: 8, 10, 12, and 14.

10. The method of embodiment 1, wherein the chimeric pesticidal polypeptide comprises an amino acid sequence selected from the group consisting of the amino acid sequences set forth in SEQ ID NOS: 2, 16, 18, 21, 23, 25, 27, and 33.

11. The method of embodiment 1, wherein the chimeric pesticidal polypeptide is encoded by a nucleotide sequence comprising the nucleotide sequence set forth in SEQ ID NO: 1, 15, 17, 20, 22, 24, 26, and 32.

12. The method of any one of embodiments 1-11, wherein the chimeric pesticidal polypeptide comprises a linker amino sequence between the first amino acid sequence and the second amino acid sequence.

13. The method of embodiment 1, wherein the linker amino acid sequence is selected from the group consisting of the amino acid sequences set forth in SEQ ID NOS: 28, 29, 30, and 31.

14. The method of any one of embodiments 1-13, further comprising operably linking the linker amino acid sequence between the first amino acid sequence and the amino acid sequence, whereby the chimeric pesticidal polypeptide comprises in linear order the first amino acid sequence, the linker amino acid sequence, and the second amino acid sequence.

15. The method of any one of embodiments 1-15, wherein the chimeric pesticidal polypeptide comprises increased pesticidal activity against at least one pest, when compared to the pesticidal activity of the Cry endotoxin against the at least one pest.

16. The method of embodiment 15, wherein the at least one pest is an insect pest.

17. The method of embodiment 16, wherein the insect pest is an insect pest from the order Coleoptera or Lepidoptera.

18. The method of embodiment 16 or 17, wherein the insect pest is from the genus *Diabrotica*.

19. The method of embodiment 16, wherein the insect pest is western corn rootworm.

20. The method of embodiment 16, wherein the insect pest is black cutworm.

21. A chimeric pesticidal polypeptide comprising a first amino acid sequence of a solubility-enhancing polypeptide operably linked to a second amino acid sequence of a Cry endotoxin.

22. The chimeric pesticidal polypeptide of embodiment 21, wherein the operably linked first and second amino sequences comprise an amino acid sequence selected from the group consisting of:

(a) the amino acid sequence set forth in SEQ ID NO: 2, 16, 18, 21, 23, 25, 27 or 33;

(b) an amino acid sequence encoded by the nucleotide sequence set forth in SEQ ID NO: 1, 15, 17, 20, 22, 24, 26 or 32; and (c) an amino acid sequence comprising at least 80% amino acid sequence identity to the amino acid sequence set forth in SEQ ID NO: 2, 16, 18, 21, 23, 25, 27 or 33, wherein the nucleotide sequence encodes a polypeptide having pesticidal activity.

23. The chimeric pesticidal polypeptide of embodiment 21 or 22, wherein the solubility-enhancing polypeptide is a MBP.

24. The chimeric pesticidal polypeptide of embodiment 23, wherein the MBP is selected from the group consisting of MBPs having an accession number set forth in Table 1.

25. The chimeric pesticidal polypeptide of embodiment 21 or 22, wherein the solubility-enhancing protein is a NusA.

26. The chimeric pesticidal polypeptide of embodiment 21 or 22, wherein the solubility-enhancing protein is a thioredoxin.

27. The chimeric pesticidal polypeptide of embodiment 21, wherein the first amino acid sequence comprises an amino acid sequence selected from the group consisting of the amino acid sequences set forth in SEQ ID NOS: 4, 6, 34, 35, and 36.

28. The chimeric pesticidal polypeptide of any one of embodiments 21-27, wherein the Cry endotoxin is selected from the group consisting of Cry endotoxins set forth in Table 2.

29. The chimeric pesticidal polypeptide of embodiment 21, wherein the Cry endotoxin comprises an amino acid sequence selected from the group consisting of SEQ ID NOS: 8, 10, 12, and 14.

30. The chimeric pesticidal polypeptide of any one of embodiments 21-29, wherein the chimeric pesticidal polypeptide further comprises a linker amino sequence operably linked between the first amino acid sequence and the second amino acid sequence.

31. The chimeric pesticidal polypeptide of embodiment 30, wherein the linker amino acid sequence is selected from the group consisting of the amino acid sequences set forth in SEQ ID NOS: 28, 29, 30, and 31.

32. The chimeric pesticidal polypeptide of any one of embodiments 21-31, wherein the chimeric pesticidal polypeptide comprises increased pesticidal activity against at least one pest, when compared to the pesticidal activity of the Cry endotoxin against the at least one pest.

33. The chimeric pesticidal polypeptide of embodiment 32, wherein the at least one pest is an insect pest.

34. The chimeric pesticidal polypeptide of embodiment 33, wherein the insect pest is an insect pest from the order Coleoptera or Lepidoptera.

35. The chimeric pesticidal polypeptide of embodiment 33, wherein the insect pest is from the genus *Diabrotica.*

36. The chimeric pesticidal polypeptide of embodiment 33, wherein the insect pest is western corn rootworm.

37. The chimeric pesticidal polypeptide of embodiment 33, wherein the insect pest is black cutworm.

38. A nucleic acid molecule comprising a nucleotide sequence encoding a chimeric pesticidal polypeptide, the chimeric pesticidal polypeptide comprising a first amino acid sequence of a solubility-enhancing polypeptide operably linked to a second amino acid sequence of a Cry endotoxin.

39. The nucleic acid molecule of embodiment 38, wherein the nucleotide sequence comprises a nucleotide sequence selected from the group consisting of:

(a) the nucleotide sequence set forth in SEQ ID NO: 1, 15, 17, 20, 22, 24, 26 or 32;

(b) a nucleotide sequence encoding the amino acid sequence set forth in SEQ ID NO: 2, 16, 18, 21, 23, 25, 27 or 33;

(c) a nucleotide sequence comprising at least 80% nucleotide sequence identity to SEQ ID NO: 1, 15, 17, 20, 22, 24, 26 or 32, wherein the nucleotide sequence encodes a polypeptide having pesticidal activity; and (e) a nucleotide sequence encoding an amino acid sequence comprising at least 80% amino acid sequence identity to the amino acid sequence set forth in SEQ ID NO: 2, 16, 18, 21, 23, 25, 27 or 33, wherein the nucleotide sequence encodes a polypeptide having pesticidal activity.

40. The nucleic acid molecule of embodiment 38 or 39, wherein the solubility-enhancing polypeptide is a MBP.

41. The nucleic acid molecule of embodiment 40, wherein the MBP is selected from the group consisting of MBPs having an accession number set forth in Table 1.

42. The nucleic acid molecule of embodiment 38 or 39, wherein the solubility-enhancing protein is a NusA.

43. The nucleic acid molecule of embodiment 38 or 39, wherein the solubility-enhancing protein is a thioredoxin.

44. The nucleic acid molecule of embodiment 38 or 39, wherein the first amino acid sequence comprises an amino acid sequence selected from the group consisting of the amino acid sequences set forth in SEQ ID NOS: 4, 6, 34, 35 and 36.

45. The nucleic acid molecule of any one of embodiments 38-44, wherein the Cry endotoxin is selected from the group consisting of Cry endotoxins set forth in Table 2.

46. The nucleic acid molecule of any one of embodiments 38-44, wherein the second amino acid sequence encodes a Cry endotoxin selected from the group consisting of Cry endotoxins set forth in Table 2.

47. The nucleic acid molecule of embodiment 38, wherein the second amino acid sequence comprises an amino acid sequence selected from the group consisting of SEQ ID NOS: 8, 10, 12 and 14.

48. The nucleic acid molecule of any one of embodiments 38-47, wherein the chimeric pesticidal polypeptide further comprises a linker amino sequence operably linked between the first amino acid sequence and the second amino acid sequence.

49. The nucleic acid molecule of embodiment 48, wherein the linker amino acid sequence is selected from the group consisting of the amino acid sequences set forth in SEQ ID NOS: 28, 29, 30, and 31.

50. The nucleic acid molecule of any one of embodiments 38-49, wherein the chimeric pesticidal polypeptide comprises increased pesticidal activity against at least one pest, when compared to the pesticidal activity of the Cry endotoxin against the at least one pest.

51. The nucleic acid molecule of any one of embodiments 38-50, wherein the at least one pest is an insect pest.

52. The nucleic acid molecule of embodiment 51, wherein the insect pest is an insect pest from the order Coleoptera or Lepidoptera.

53. The nucleic acid molecule of embodiment 51, wherein the insect pest is from the genus *Diabrotica.*

54. The nucleic acid molecule of embodiment 51, wherein the insect pest is western corn rootworm.

55. The nucleic acid molecule of embodiment 51, wherein the insect pest is black cutworm.

56. An expression cassette comprising a promoter that drives expression in a host cell operably linked to a nucleic acid molecule of any one of embodiments 38-55.

57. The expression cassette of embodiment 56, wherein the host cell is a plant cell.

58. The expression cassette of embodiment 57, wherein the promoter is selected from the group consisting of a chemical-inducible promoter, constitutive promoter, pest-inducible promoter, tissue-specific promoter and wound-inducible promoter.

59. The expression cassette of embodiment 58, wherein the tissue-specific promoter is selected from the group consisting of a leaf-preferred promoter, root-preferred promoter, seed-preferred promoter, stalk-preferred promoter and vascular tissue-preferred promoter.

60. A vector comprising the expression cassette of any one of embodiments 56-59.

61. A transformed plant, plant part, plant cell or seed comprising in its genome the expression cassette of any one of embodiments 56-60.

62. The transformed plant, plant part or plant host cell of embodiment 61, wherein the nucleotide sequence is stably incorporated into the genome of the transformed plant, plant part, plant cell or seed.

63. A pesticidal composition comprising an effective amount of a chimeric pesticidal polypeptide of any one of embodiments 21-37 or an active variant or fragment thereof having pesticidal activity.

64. The pesticidal composition of embodiment 63, further comprising bacteria expressing a nucleotide sequence encoding the chimeric pesticidal polypeptide or a biologically active fragment or variant thereof.

65. The pesticidal composition of embodiment 63, further comprising at least one agricultural protectant selected from the group consisting of an acaricide, bactericide, fertilizer or micronutrient donor, fungicide, insecticide, nematocide and semiochemical.

66. The pesticidal composition of embodiment 65, wherein the semiochemical is selected from the group consisting of an allomone, attractant, feeding pheromone, kairomone, repellent and stimulant.

67. A method of protecting a plant from an insect pest, the method comprising providing an effective amount of a pesticidal composition of any one of embodiments 63-66 to reduce insect pest-related damage to the plant.

68. The method of embodiment 67, wherein the pesticidal composition is applied by a procedure selected from the group consisting of spraying, dusting, broadcasting and seed coating.

69. The method of embodiment 67 or 68, wherein the chimeric pesticidal polypeptide has pesticidal activity against an insect pest in the order Coleoptera, an insect pest in the order Lepiedoptera or both.

70. The method of any one of embodiments 67-69, wherein the insect pest is selected from the group consisting of species in the genus *Diabrotica.*

71. A plant comprising a polynucleotide construct stably incorporated in its genome, the polynucleotide construct comprising a nucleotide sequence operably linked to a promoter that drives expression in the plant, wherein the nucleotide sequence encodes a chimeric pesticidal polypeptide comprising a first amino acid sequence of a solubility-enhancing polypeptide operably linked to a second amino acid sequence of a Cry endotoxin.

72. The plant of embodiment 71, wherein the nucleotide sequence is selected from the group consisting of:

(a) the nucleotide sequence set forth in SEQ ID NO: 1, 15, 17, 20, 22, 24, 26 or 32;

(b) a nucleotide sequence encoding the amino acid sequence set forth in SEQ ID NO: 2, 16, 18, 21, 23, 25, 27 or 33;

(c) a nucleotide sequence comprising at least 80% nucleotide sequence identity to SEQ ID NO: 1, 15, 17, 20, 22, 24, 26 or 32, wherein the nucleotide sequence encodes a polypeptide having pesticidal activity; and (e) a nucleotide sequence encoding an amino acid sequence comprising at least 80% amino acid sequence identity to the amino acid sequence set forth in SEQ ID NO: 2, 16, 18, 21, 23, 25, 27 or 33, wherein the nucleotide sequence encodes a polypeptide having pesticidal activity.

73. The plant of embodiment 71 or 72, wherein the solubility-enhancing polypeptide is MBP.

74. The plant of embodiment 73, wherein the MBP is selected from the group consisting of MBPs having an accession number set forth in Table 1.

75. The plant of embodiment 71 or 72, wherein the solubility-enhancing protein is NusA.

76. The plant of embodiment 71 or 72, wherein the solubility-enhancing protein is thioredoxin.

77. The plant of embodiment 71, wherein the first amino acid sequence comprises an amino acid sequence selected from the group consisting of the amino acid sequences set forth in SEQ ID NOS: 4, 6, 34, 35 and 36.

78. The plant of any one of embodiments 71-77, wherein the Cry endotoxin is selected from the group consisting of Cry endotoxins set forth in Table 2.

79. The plant of any one of embodiments 71-78, wherein the second amino acid sequence encodes a Cry endotoxin selected from the group consisting of Cry endotoxins set forth in Table 2.

80. The plant of embodiment 71 or 72, wherein the second amino acid sequence comprises an amino acid sequence selected from the group consisting of SEQ ID NOS: 8, 10, 12 and 14.

81. The plant of any one of embodiments 71-80, wherein the chimeric pesticidal polypeptide further comprises a linker amino sequence operably linked between the first amino acid sequence and the second amino acid sequence.

82. The nucleic acid molecule of embodiment 81, wherein the linker amino acid sequence is selected from the group consisting of the amino acid sequences set forth in SEQ ID NOS: 28, 29, 30 and 31.

83. The plant of any one of embodiments 71-82, wherein the chimeric pesticidal polypeptide comprises increased pesticidal activity against at least one pest, when compared to the pesticidal activity of the Cry endotoxin against the at least one pest.

84. The plant of embodiment 83, wherein the at least one pest is an insect pest.

85. The plant of embodiment 84, wherein the insect pest is an insect pest from the order Coleoptera or Lepidoptera.

86. The plant of embodiment 84, wherein the insect pest is from the genus *Diabrotica.*

87. The plant of embodiment 84, wherein the insect pest is western corn rootworm.

88. The plant of embodiment 84, wherein the insect pest is black cutworm.

89. The plant of any one of embodiments 71-88, wherein the plant is a monocot.

90. The plant of embodiment 89, wherein the monocot is barley, maize, rice, rye, *sorghum*, sugarcane or wheat.

91. The plant of any one of embodiments 71-88, wherein the plant is a dicot.

92. The plant of embodiment 91, wherein the dicot is alfalfa, *Brassica*, cotton, soybean or sunflower.

93. The plant of any one of embodiment 71-92, wherein the plant is a seed.

94. A method of protecting a plant, plant part or plant host cell from an insect pest, the method comprising the steps of:

(a) introducing into the plant, plant part or plant host cell an expression cassette of any one of embodiments 56-59; and (b) regenerating the plant, plant part or plant host cell into a morphologically normal fertile plant, wherein the plant or part thereof comprises a chimeric pesticidal polypeptide.

95. The method of embodiment 94, wherein the chimeric pesticidal polypeptide has pesticidal activity against an insect pest in the order Coleoptera, an insect pest in the order Lepidoptera or both.

96. The method of embodiment 94, wherein the insect pest is selected from the group consisting of species in the genus *Diabrotica.*

97. A method of enhancing the resistance of a plant to at least one pest, the method comprising introducing into a plant or at least one plant cell a polynucleotide construct comprising a nucleotide sequence operably linked to a promoter that drives expression in the plant, wherein the nucleotide sequence encodes a chimeric pesticidal polypeptide comprising a first amino acid sequence of a solubility-enhancing polypeptide operably linked to a second amino acid sequence of a Cry endotoxin.

98. The method of embodiment 97, wherein the nucleotide sequence comprises a nucleotide sequence selected from the group consisting of:

(a) the nucleotide sequence set forth in SEQ ID NO: 1, 15, 17, 20, 22, 24, 26 or 32;

(b) a nucleotide sequence encoding an amino acid sequence comprising the amino acid sequence set forth in SEQ ID NO: 2, 16, 18, 21, 23, 25, 27 or 33;

(c) a nucleotide sequence comprising at least 80% nucleotide sequence identity to SEQ ID NO: 1, 15, 17, 20, 22, 24, 26 or 32, wherein the nucleotide sequence encodes a polypeptide having pesticidal activity; and (e) a nucleotide sequence encoding an amino acid sequence comprising at least 80% amino acid sequence identity to the amino acid sequence set forth in SEQ ID NO: 2, 16, 18, 21, 23, 25, 27 or 33, wherein the nucleotide sequence encodes a polypeptide having pesticidal activity.

99. The method of embodiment 97 or 98, wherein solubility-enhancing polypeptide is MBP.

100. The method of embodiment 99, wherein the MBP is selected from the group consisting of MBPs having an accession number set forth in Table 1.

101. The method of embodiment 97 or 98, wherein the solubility-enhancing protein is NusA.

102. The method of embodiment 97 or 98, wherein the solubility-enhancing protein is thioredoxin.

103. The method of embodiment 97, wherein the first amino acid sequence comprises an amino acid sequence selected from the group consisting of the amino acid sequences set forth in SEQ ID NOS: 4, 6, 34, 35 and 36.

104. The method of any one of embodiments 97-103, wherein the Cry endotoxin is selected from the group consisting of Cry endotoxins set forth in Table 2.

105. The method of any one of embodiments 97-104, wherein the second amino acid sequence comprises an amino acid sequence selected from the group consisting of SEQ ID NOS: 8, 10, 12 and 14.

106. The method of any one of embodiments 97-105, wherein the chimeric pesticidal polypeptide further comprises a linker amino sequence operably linked between the first amino acid sequence and the second amino acid sequence.

107. The method of embodiment 106, wherein the linker amino acid sequence is selected from the group consisting of the amino acid sequences set forth in SEQ ID NOS: 28, 29, 30 and 31.

108. The method of any one of embodiments 97-107, wherein the chimeric pesticidal polypeptide comprises increased pesticidal activity against at least one pest, when compared to the pesticidal activity of the Cry endotoxin against the at least one pest.

109. The method of any one of embodiments 97-108, further comprising regenerating a plant comprising the polynucleotide construct.

110. The method of any one of embodiments 97-109, wherein the plant has enhanced resistance to at least one pest, when compared to a control plant lacking the polynucleotide construct.

111. The method of embodiment 110, wherein the at least one pest is an insect pest.

112. The method of embodiment 111, wherein the insect pest is an insect pest from the order Coleoptera or Lepidoptera.

113. The method of embodiment 111, wherein the insect pest is from the genus *Diabrotica.*

114. The method of embodiment 111, wherein the insect pest is western corn rootworm.

115. The method of embodiment 111, wherein the insect pest is black cutworm.

116. The method of any one of embodiments 97-115, wherein the plant is a monocot.

117. The method of embodiment 116, wherein the monocot is barley, maize, rice, rye, *sorghum*, sugarcane or wheat.

118. The method of any one of embodiments 97-115, wherein the plant is a dicot.

119. The method of embodiment 118, wherein the dicot is alfalfa, *Brassica*, cotton, soybean or sunflower.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 1 depicts the structure of *E. coli* maltose-binding protein (MBP)-Bt Cry protein fusion of the present invention. ▒ =maltose binding protein ▥ =Bt Cry protein.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention is based on the discovery that pesticidal activity of Cry endotoxins can be enhanced by operably linking a solubility-enhancing polypeptide, such as, for example, a maltose-binding protein (MBP), to a Cry endotoxin or insecticidally active fragment thereof. Moreover, insect pest resistance can be overcome by operably linking an MBP to a Cry endotoxin by the methods disclosed herein. The present invention therefore provides compositions and methods for enhancing Cry endotoxin activity, for overcoming plant pest resistance, and for protecting plants from pests, especially insect pests.

While the invention does not depend on a particular biological mechanism, the fusion of a solubility-enhancing polypeptide to a Cry endotoxin or insecticidally active fragment thereof may act to raise the solubility of the Cry protein, particularly in the insect gut environment, more particularly in the gut environment of a Coleopteran insect. That is the solubility of the fusion protein has a higher solubility at a slightly acidic pH than the Cry protein has at the same pH. In a preferred embodiment of the invention, with activated Cyr toxin that is used in making the fusion protein of the invention has an isoelectric point (pi) from about pH 7 to about pH 8. It is recognized that in the digestive system in Lepidopteran insects, pH is relatively high. In such alkaline conditions, an activated Bt Cry toxin typically is soluble but in the slightly acidic pH of the Coleopteran gut environment in which pH is slightly acidic, solubility of the activated Bt Cry toxin can be much lower.

Compositions and methods are provided for enhancing the pesticidal activity of Cry endotoxins by operably linking a solubility-enhancing protein to a Cry endotoxin and for protecting plants from insect pests. The compositions and methods disclosed herein include recombinant nucleic acid molecules that encode chimeric pesticidal polypeptides, expression cassettes and other nucleotide constructs including the nucleic acid molecules described herein organisms transformed with the nucleic acid molecules described herein, isolated chimeric pesticidal polypeptides, and pesticidal compositions having the chimeric pesticidal polypeptides, as well as methods of using the same. The compositions and methods therefore find use in enhancing pesticidal activity of pesticidal proteins and in protecting plants from insect pests.

As used herein, a "solubility-enhancing polypeptide" is any polypeptide that when operably linked to a Cry endotoxin or insecticidally active fragment thereof enhances the pesticidal activity of the Cry endotoxin or insecticidally active fragment against at least one insect pest, preferably a Coleopteran insect pest, when compared to the pesticidal activity of the same Cry endotoxin or insecticidally active fragment thereof in the absence of an operably linked solubility-enhancing polypeptide. In certain embodiments, the solubility enhancing polypeptides of the present invention are capable of increasing the solubility of an operable linked Cry endotoxin or insecticidally active fragment thereof at a slightly acidic pH that is found, for example, in the gut environment of a Coleopteran insect. Preferably, a chimeric pesticidal polypeptide of the present invention, which comprises a solubility-enhancing polypeptide of the present invention operably linked to a Cry endotoxin or insecticidally active fragment thereof, comprises an increased solubility in an environment that has a slightly acidic pH such as, for example, the gut environment of a Coleopteran insect, than the same Cry endotoxin or insecticidally active fragment thereof lacking the operably linked solubility-enhancing polypeptide.

As used herein, "pest" or "plant pest" means an organism that interferes with or is harmful to plant development and/or growth. Such plant pests include, but are not limited to, nematodes, insect, viruses, viroids, mites, fungal pathogens, bacteria and any other plant pests disclosed herein. Accordingly, the polynucleotides and polypeptides of the invention can be used to enhance resistance of plants to plant pests. One of skill in the art, however, understands that not all polypeptides are equally effective against all plant pests. The chimeric pesticidal polypeptides described herein display activity against plant pests such as insect pests, which may include economically important agronomic, forest, greenhouse, nursery ornamentals, food and fiber, public and animal health, domestic and commercial structure, household and stored product pests. Therefore, of interest herein are chimeric pesticidal polypeptides for use in protecting plants from insect pests.

As used herein, "pesticidal polypeptide" means a peptide, polypeptide or protein that has biological activity against insect pests (i.e., is pesticidal).

As used herein, "pesticidal" or "pesticidal activity" means capable of killing insect pests. Likewise, "pesticidal" or "pesticidal activity" means capable of inhibiting insect growth. As such, the chimeric pesticidal polypeptides described herein are capable of inhibiting growth or reproduction of or of killing, at least one plant pest, particularly at least one insect pest.

By "insecticidal activity" is intended the ability of a polypeptide of the invention or a composition comprising the polypeptide (or other agent, chemical or composition) to inhibit the growth of or damage to a plant caused by, at least one insect pest.

As used herein, "enhance" and the like means increasing an activity/effectiveness of a pesticidal polypeptide such as a Cry endotoxin against a particular pest by operably linking the Cry endotoxin to a solubility-enhancing polypeptide, where the activity/effectiveness of the resulting chimeric pesticidal polypeptide is increased by about 1% to about 5%, about 5% to about 10%, about 10% to about 20%, about 20% to about 30%, about 30% to about 40%, about 40% to about 50%, about 50% to about 60%, about 60% to about 70%, about 70% to about 80%, about 80% to about 90% or about 90% to about 100% when compared to a wild-type Cry endotoxin. Alternatively, the activity/effectiveness of the chimeric pesticidal polypeptide is increased by about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more when compared to the wild-type Cry endotoxin. In addition, “enhance” can mean that the host pest range of the pesticidal polypeptide is expanded to include additional pests.

As used herein, “about” means within a statistically meaningful range of a value such as a stated concentration, length, molecular weight, percentage, pH, time frame, temperature or volume. Such a value or range can be within an order of magnitude, typically within 20%, more typically within 10%, and even more typically within 5% of a given value or range. The allowable variation encompassed by “about” will depend upon the particular system under study, and can be readily appreciated by one of skill in the art.

As used herein, “chimeric polypeptide” or “chimeric pesticidal polypeptide” means a polypeptide having a first amino acid sequence derived from a first source operably linked, covalently or non-covalently, to a second amino acid sequence derived from a second source, where the first and second source are not the same. A first source and a second source that are not the same can include two different organisms or two different proteins from the same organism or a biological source and a synthetic source or even two different synthetic sources. A biological source can include any non-synthetically produced nucleotide or amino acid sequence (e.g., a genomic or cDNA sequence, a plasmid or viral vector, a native virion or a mutant or analog). A synthetic source can include a nucleotide or amino acid sequence produced chemically and not by a biological source (e.g., solid phase synthesis of amino acid sequences). The chimeric pesticidal polypeptide can be produced by expressing a recombinant nucleic acid molecule encoding a polypeptide having at least two parts or can be produced synthetically.

A chimeric pesticidal polypeptide of the present can further comprise, for example, a linker molecule (also referred to here as a “linker) between the first and second amino acid sequences. Examples of linkers that can be used in the methods of the present invention are the NEB pMAL, SA, NusA, and TrxA linkers having the amino acid sequences set forth in SEQ ID NOS: 28, 29, 30, and 31, respectively.

Solubility-enhancing polypeptides of the present include, but are not limited to, maltose-binding protein (MBP), thioredoxin (e.g., TrxA), transcription elongation factor NusA, glutathione-S-transferase (GST), mistic, small ubiquitin-related modifier (SUMO), protein disulfide isomerase DsbC, and thiol:disulfide interchange protein DsbD, and variants and fragments thereof that when operably linked to a Cry endotoxin or insecticidally active fragment thereof enhance the pesticidal activity of an operably linked Cry endotoxin or insecticidally active fragment against at least one insect pest, preferably a Coleopteran insect pest, when compared to the pesticidal activity of the same Cry endotoxin or insecticidally active fragment thereof in the absence of an operably linked solubility-enhancing polypeptide.

As used herein, “maltose-binding protein” or “MBP” means a polypeptide that is a member of the maltodextrin transport system that binds maltodextrins (e.g., maltose, maltotriose and trehalose) with micromolar affinity and that is essential for an energy-dependent translocation of maltodextrins through a cytoplasmic membrane of some prokaryotes. See, Boos & Shuman (1998) *Microbiol. Mol. Biol. Rev.* 62:204-229. For example, in *Escherichia coli*, the malE gene encodes a 396 amino acid residue pre-MBP, which subsequently is processed into MBP upon cleavage of a 26 amino acid N-terminal signal peptide. See, e.g., Duplay et al. (1984) *J. Biol. Chem.* 259:10606-10613.

In one embodiment of the invention, the chimeric pesticidal polypeptide comprises an amino acid sequence of an MBP operably linked to an amino acid sequence of a Cry endotoxin including, for example, the chimeric pesticidal polypeptides comprising the amino acid sequences set forth in SEQ ID NOS: 2, 21, 23, 25, 27, and 33 and encoded by the nucleotide sequences set forth in SEQ ID NOS: 1, 20, 22, 24, 26, and 32, respectively.

In another embodiment, the chimeric pesticidal polypeptide comprises an amino acid sequence of NusA operably linked to an amino acid sequence of a Cry endotoxin including, for example, the chimeric pesticidal polypeptide comprising the amino acid sequence set forth in SEQ ID NO: 16 and encoded by the nucleotide sequence set forth in SEQ ID NO: 15.

In yet another embodiment, the chimeric pesticidal polypeptide comprises an amino acid sequence of thioredoxin operably linked to an amino acid sequence of a Cry endotoxin including, for example, the chimeric pesticidal polypeptide comprising the amino acid sequence set forth in SEQ ID NO: 18 and encoded by the nucleotide sequence set forth in SEQ ID NO: 17.

The present invention comprises the use of an solubility-enhancing polypeptide that when fused to a Cry endotoxin polypeptide increases the pesticidial activity of against at least one pest, preferably an insect pest, more preferably an insect pest from the order Coleoptera or Lepidoptera, even more preferably an insect pest from the genus *Diabrotica*, most preferably the western corn rootworm (*Diabrotica virgifera virgifera*). In certain embodiments, the solubility-enhancing polypeptide selected from the group consisting of MBP, NusA, and TrxA.

The present invention does not depend on the use of a particular solubility-enhancing polypeptide. Any solubility-enhancing polypeptide that, when fused to a Cry endotoxin polypeptide, is capable increasing the pesticidial activity of the Cry endotoxin polypeptide against at least one pest can be used in the methods and compositions disclosed herein. Such solubility enhancing polypeptides include, for example, pre-proteins and mature proteins, and variants and fragments thereof. In certain embodiments, the solubility-enhancing polypeptide is MBP. MBPs of the present invention include, but are not limited, full-length MBP (also referred to as “pre-MBP”, a mature form of an MBP, a fragment of a full-length or mature MBP or a variant. Unless expressed stated herein or otherwise apparent form the context, the terms “maltose-binding protein” and “MBP” encompass such full-length and mature forms of MBPs as well as fragments and variants thereof.

The amino acid and/or nucleotide sequences for a number of MBPs have been disclosed and can be used in the compositions and methods of the present invention including, but not limited to, the following those MBPs having the following accession numbers in Table 1.

TABLE 1

| GenBank Accession Number* | | | | |
|---|---|---|---|---|
| NP_290668 | ZP_03064501 | CBG37227 | NP_709885 | ACI74011 |
| YP_002415175 | YP_001726921 | EFK20320 | ZP_02999303 | YP_312946 |

TABLE 1-continued

| GenBank Accession Number* | | | | |
|---|---|---|---|---|
| ZP_06651607 | ACC91724 | NP_756856 | ACF57854 | ACF57853 |
| ABO28850 | AAB86559 | AAC83813 | BAI57431 | AAQ93661 |
| ACI46135 | ACI46133 | AAK55118 | AAB87675 | ZP_02904048 |
| YP_002385139 | ZP_06356417 | YP_003367151 | YP_002639794 | NP_458527 |
| YP_001338045 | ACY91424 | ZP_03381315 | YP_219095 | AAX68014 |
| AAL23053 | NP_463094 | ZP_04558600 | YP_002228802 | ZP_02700756 |
| YP_002149143 | CAA38189 | CBK84491 | ZP_06390929 | YP_001455393 |
| YP_003610806 | YP_001174979 | YP_001572421 | YP_002241024 | P18815 |
| YP_003212142 | YP_001436222 | YP_001480694 | ZP_06712852 | ZP_04616043 |
| ZP_04638283 | ZP_06191619 | ZP_04626936 | ZP_04633703 | ZP_04613648 |
| NP_667372 | ZP_04641958 | YP_001161578 | YP_001008013 | ZP_04625082 |
| YP_003294268 | YP_002931694 | ZP_06638363 | BAE44434 | YP_003743846 |
| YP_003039205 | NP_927811 | ZP_05729913 | YP_003714385 | YP_003469920 |
| YP_003729949 | YP_003520206 | YP_002891253 | ZP_03366279 | ZP_05920010 |
| YP_003007381 | ZP_06636620 | YP_001343631 | YP_003255618 | ZP_04976824 |
| YP_089260 | ZP_06157313 | YP_002474876 | YP_001447347 | ZP_01984309 |
| ZP_04754507 | ZP_06177188 | NP_800911 | ZP_06180148 | ZP_02477508 |
| ZP_01258612 | ZP_05878943 | ZP_05629984 | YP_001053928 | YP_132094 |
| ZP_05882865 | ZP_02194153 | ZP_01221443 | ZP_05927269 | NP_763457 |
| ZP_05943387 | ZP_01865449 | ZP_05717553 | ZP_06032225 | ZP_06079586 |
| ZP_05239461 | YP_002812521 | NP_233329 | ZP_01970977 | ZP_04918366 |
| ZP_05719582 | ZP_05886194 | ZP_05117778 | ZP_06941932 | ZP_04415908 |
| ZP_01950896 | ZP_01676462 | ZP_01897017 | YP_001343632 | YP_132089 |
| ZP_06938154 | YP_003007380 | ZP_03352864 | ZP_01221449 | ZP_00988394 |
| ZP_01811558 | YP_856203 | YP_001142458 | NP_936112 | ZP_01062901 |
| NP_763137 | YP_206757 | ZP_00988462 | ZP_04403894 | ZP_05120494 |
| ZP_01947956 | ZP_01062959 | ZP_01865441 | YP_431775 | ZP_01895948 |
| YP_001173956 | ZP_03375554 | YP_001188617 | ZP_00135549 | ZP_03699982 |
| YP_003269532 | YP_003548264 | ZP_01893753 | ZP_01112736 | YP_431868 |
| ZP_01157584 | ZP_01115171 | ZP_03369842 | ZP_01955972 | ZP_01955970 |
| ZP_06938864 | YP_002352611 | YP_002250432 | YP_002534909 | NP_229009 |
| YP_001245135 | YP_002534307 | YP_001739017 | YP_001244560 | YP_003346096 |
| YP_002250571 | CAA72193 | NP_229635 | YP_002352749 | YP_001470540 |
| NP_623418 | ZP_05493657 | YP_001662811 | YP_002941091 | YP_003672376 |
| YP_146557 | ZP_04392773 | YP_003677351 | ZP_05336993 | YP_003477456 |
| AAY89718 | YP_001568299 | YP_001410291 | ZP_03385039 | YP_001568464 |
| YP_001124738 | YP_604964 | YP_003514612 | ZP_03146818 | ZP_04152680 |
| ZP_04158384 | YP_001305848 | YP_001142178 | ZP_04307633 | YP_002509363 |
| ZP_06220504 | ZP_04121933 | ZP_04204735 | ZP_03232052 | YP_003148220 |
| ZP_04086064 | ZP_04258265 | ZP_04296475 | ZP_02397670 | ZP_00236932 |
| ZP_04187645 | ZP_03105903 | ZP_03238270 | YP_896372 | YP_038073 |
| YP_085351 | NP_846464 | ZP_04128078 | ZP_04285672 | YP_003186266 |
| ZP_02948002 | YP_002447583 | CAB65651 | NP_980358 | ZP_04302212 |
| ZP_03493519 | ZP_02878398 | ZP_04176050 | ZP_05183404 | ZP_04290906 |
| ZP_04199019 | ZP_04263630 | YP_001646638 | ZP_04229423 | ZP_04170363 |
| YP_002334500 | BAB40635 | ZP_04218748 | ZP_02866107 | YP_697032 |
| YP_003258733 | ZP_02953587 | YP_177014 | YP_051264 | ZP_02638879 |
| YP_003018517 | ZP_04607307 | ZP_03828721 | YP_003116555 | ZP_03832162 |
| YP_002316535 | NP_294284 | NP_563259 | YP_002785582 | YP_002886868 |
| ZP_06681977 | ZP_05667047 | ZP_05664221 | ZP_03981553 | ZP_06699376 |
| YP_001488817 | YP_001375943 | ZP_00603967 | ZP_05132228 | YP_699603 |
| YP_002574412 | YP_001814130 | YP_003445304 | ZP_04878976 | ZP_03055079 |
| ZP_01861955 | YP_002918149 | YP_002240053 | YP_001334109 | YP_001813248 |
| ZP_06549508 | ZP_06329195 | ZP_04864724 | YP_001179261 | YP_144918 |
| YP_039671 | NP_645005 | NP_370738 | YP_003465347 | ZP_05877552 |
| ZP_04016117 | YP_001439475 | BAI87082 | ADI96692 | CBI48099 |
| YP_850342 | YP_005257 | ZP_00233442 | YP_003613139 | ZP_06315382 |
| YP_946709 | NP_391341 | AAD42742 | EFK15520 | ZP_05300115 |
| ZP_05298949 | YP_001695468 | ZP_02185856 | YP_830242 | YP_288893 |
| NP_471563 | YP_003208908 | YP_002958966 | YP_001836789 | ZP_01827852 |
| YP_415662 | NP_359509 | BAB18102 | YP_002739191 | YP_003154662 |
| ZP_03497002 | YP_003696753 | YP_003684577 | ZP_07053052 | ZP_05231671 |
| ZP_02711433 | ZP_01821820 | ZP_01821214 | NP_346527 | ZP_01408156 |
| ZP_02186034 | BAC10980 | YP_003336687 | NP_670540 | YP_071605 |
| ZP_06640983 | YP_003723548 | ZP_04853514 | YP_002743432 | YP_001399898 |
| YP_077886 | YP_002038696 | NP_391296 | ZP_06611384 | ZP_06198009 |
| YP_003339007 | YP_003729851 | ZP_03958786 | ZP_01170933 | YP_081353 |
| YP_001719722 | ZP_06059512 | YP_001449426 | ZP_06872846 | ZP_04851795 |
| YP_003241054 | YP_002473273 | YP_001396549 | YP_920853 | ZP_06190079 |
| BAI87023 | YP_001664668 | YP_003704868 | ZP_06899649 | NP_693481 |
| YP_003314160 | YP_003334475 | ZP_05647136 | YP_003203952 | YP_056254 |
| ZP_06014674 | ZP_05687198 | YP_003506902 | ZP_04449975 | YP_002958266 |
| YP_002948859 | YP_003677653 | ZP_06428097 | YP_003781558 | ZP_03925962 |
| YP_001199499 | NP_579667 | YP_003003618 | YP_003678645 | ZP_03225712 |
| ZP_01460386 | YP_003326738 | YP_002744243 | YP_002746719 | YP_002123617 |
| AAA26922 | YP_003477807 | ZP_02329884 | ZP_04431587 | ZP_01461944 |
| NP_242885 | YP_003161478 | ZP_06533915 | YP_001137791 | YP_003009537 |
| NP_125870 | YP_002308182 | ZP_06885100 | ZP_04876799 | YP_001559408 |

TABLE 1-continued

| GenBank Accession Number* | | | | |
|---|---|---|---|---|
| YP_003699585 | ZP_01130620 | YP_184184 | ZP_05621839 | NP_243792 |
| YP_002883083 | YP_003637265 | YP_003425427 | YP_003061750 | YP_002997014 |
| ZP_07076764 | ZP_05749331 | YP_602654 | NP_269430 | NP_737480 |
| ZP_06808450 | YP_003009727 | YP_002565304 | YP_598732 | YP_280516 |
| YP_002881503 | NP_784007 | YP_002246441 | ZP_02045060 | YP_002509787 |
| ZP_06608272 | YP_002136599 | ZP_06363693 | EFK02214 | ZP_05431814 |
| YP_136875 | ZP_06662656 | YP_001880661 | YP_177522 | ZP_06048003 |
| YP_002387348 | ZP_01983428 | YP_003229678 | ZP_04402673 | YP_467337 |
| ZP_06365288 | CAL69747 | YP_002881799 | ZP_04412511 | ZP_01951248 |

*The amino acid and corresponding nucleotide sequences of the accession numbers in Table 1 are herein incorporated by reference.

In certain embodiments of the invention, the MBP comprises the amino acid sequence set forth in SEQ ID NO: 4 or 6 or fragment or variant thereof. Any nucleotide sequence encoding the amino acid sequence set forth in SEQ ID NO: 4 or 6 or fragment or variant thereof, can be used in the methods and compositions of the present invention. In some embodiments of the invention, the nucleotide sequences of the invention will be optimized for expression in a host organism or cell of interest, particularly a plant, more particularly a crop plant, most particularly a maize plant.

As used herein, "Cry endotoxin" means a δ-endotoxin encoded by cry (crystal protein) genes that are located mainly on large plasmids in members of the genus *Bacillus*, although chromosomally encoded Cry endotoxins have been reported. See, Ben-Dov et al. (1996) *Appl. Environ. Microbiol.* 62:3140-3145; Berry et al. (2002) *Appl. Environ. Microbiol.* 68:5082-5095; Gonzáles et al. (1981) *Plasmid* 5:351-365; Lereclus et al. (1982) *Mol. Gen. Genet.* 186:391-398; and Trisrisook et al. (1990) *Appl. Environ. Microbiol.* 56:1710-1716. Cry endotoxins do not have a broad spectrum of activity, so they typically do not kill beneficial insects. Furthermore, Cry endotoxins are non-toxic to mammals, including humans, domesticated animals and wildlife.

Cry endotoxins generally have five conserved sequence domains, and three conserved structural domains. See, e.g., de Maagd et al. (2001) *Trends Genetics* 17:193-199. The first conserved structural domain (Domain I) consists of seven alpha helices and is involved in membrane insertion and pore formation. The second conserved structural domain (Domain II) consists of three beta-sheets arranged in a Greek key configuration, and the third conserved structural domain (Domain III) consists of two antiparallel beta-sheets in "jelly-roll" formation. Domains II and III are involved in receptor recognition and binding, and are therefore considered determinants of toxin specificity.

As used herein, "insect pest" means an organism in the phylum Arthropoda that interferes with or is harmful to plant development and/or growth, and more specifically means an organism in the class Insecta. The class Insecta can be divided into two groups historically treated as subclasses: (1) wingless insects, known as Apterygota; and (2) winged insects, known as Pterygota. The insect pests can be adults, larvae or even ova. A preferred developmental stage for testing for pesticidal activity is larvae or other immature form of the insect pest. Methods of rearing insect larvae and performing bioassays are well known in the art. See, e.g., Czapla & Lang (1990) *J. Econ. Entomol.* 83:2480-2485; Griffith & Smith (1977) *J. Aust. Ent. Soc.* 16:366; and Keiper & Foote (1996) *Hydrobiologia* 339:137-139; as well as U.S. Pat. No. 5,351,643. For example, insect pests can be reared in total darkness at about 20° C. to about 30° C. and from about 30% to about 70% relative humidity.

Compositions comprising chimeric pesticidal polypeptide-encoding nucleic acid molecules and chimeric pesticidal polypeptides also are provided. The compositions include chimeric pesticidal polypeptides that comprise a solubility-enhancing polypeptide fused to a Cry endotoxin or biologically active fragment thereof. Nucleotide sequences that encode the chimeric pesticidal polypeptides can be derived from the chimeric pesticidal polypeptide sequence and produced using any method known in the art. The compositions also include variants and fragments of the chimeric pesticidal-encoding nucleic acid molecules and chimeric pesticidal polypeptides. The isolated, chimeric pesticidal-encoding nucleic acid molecules can be used to create transgenic organisms, such as plants, that are resistant to an insect pest susceptible to the pesticidal polypeptide.

The presently disclosed methods and compositions provides for chimeric pesticidal polypeptides with improved efficacy and nucleic acid molecules encoding the chimeric pesticidal polypeptides. The chimeric pesticidal polypeptides comprise solubility-enhancing polypeptide fused (i.e., operably linked) to a Cry endotoxin or biologically active fragment thereof and have enhanced pesticidal activity against at least one plant pest, when compared to the pesticidal activity of the Cry endotoxin or biologically active fragment thereof that has not been fused to a solubility-enhancing polypeptide.

As used herein, "pesticide," "pesticidal polypeptide," or "pesticidal protein" mean a polypeptide that is capable of killing the pest or inhibiting its growth, feeding or reproduction. One of skill in the art understands that not all substances or mixtures thereof are equally effective against all pests. "Chimeric pesticidal polypeptides" or "chimeric pesticidal proteins" are "pesticidal polypeptides" or "pesticidal proteins", to which a solubility-enhancing polypeptide has been fused as disclosed herein. Of particular interest herein are pesticidal polypeptides and chimeric pesticidal polypeptides that act as insecticides and thus have biological activity against insect pests.

As used herein, "pest" means an organism that interferes with or is harmful to plant development and/or growth. Examples of pests include, but are not limited to, algae, arachnids (e.g., acarids including mites and ticks), bacteria (e.g., plant pathogens including *Xanthomonas* spp. and *Pseudomonas* spp.), crustaceans (e.g., pillbugs and sowbugs); fungi (e.g., members in the phylum Ascomycetes or Basidiomycetes, and fungal-like organisms including Oomycetes such as *Pythium* spp. and *Phytophthora* spp.), insects, mollusks (e.g., snails and slugs), nematodes (e.g., soil-transmitted nematodes including *Clonorchis* spp., *Fasciola* spp., *Heterodera* spp., *Globodera* spp., *Opisthorchis* spp. and *Paragonimus* spp.), protozoans (e.g., *Phytomonas* spp.), viruses (e.g., *Comovirus* spp., *Cucumovirus* spp.,

*Cytorhabdovirus* spp., *Luteovirus* spp., *Nepovirus* spp., *Potyvirus* spp., *Tobamovirus* spp., *Tombusvirus* spp. and *Tospovirus* spp.), viroids, parasitic plants, and weeds.

Of particular interest herein are insect pests. As used herein, "insect pest" means an organism in the phylum Arthropoda that interferes with or is harmful to plant development and/or growth, and more specifically means an organism in the class Insecta. The class Insecta can be divided into two groups historically treated as subclasses: (1) wingless insects, known as Apterygota; and (2) winged insects, known as Pterygota. Examples of insect pests include, but are not limited to, insects in the orders Coleoptera, Diptera, Hemiptera, Homoptera, Hymenoptera, Isoptera, Lepidoptera, Mallophaga orthroptera, Thysanoptera, Dermaptera, Isoptera, Anoplura, Siphonaptera, Trichoptera and Thysanura, particularly Coleoptera and Lepidoptera. While technically not insects, arthropods such as arachnids, especially in the order Acari, are included in "insect pest." Insect pests include economically important agronomic, forest, greenhouse, nursery ornamentals, food and fiber, public and animal health, domestic and commercial structure, household, and stored product pests.

Insects of the order Lepidoptera include, but are not limited to, armyworms, cutworms, loopers, and heliothines in the family Noctuidae *Agrotis ipsilon* Hufnagel (black cutworm); *A. orthogonia* Morrison (western cutworm); *A. segetum* Denis & Schiffermüller (turnip moth); *A. subterranea* Fabricius (granulate cutworm); *Alabama argillacea* Hubner (cotton leaf worm); *Anticarsia gemmatalis* Hubner (velvetbean caterpillar); *Athetis mindara* Barnes and McDunnough (rough skinned cutworm); *Earias insulana* Boisduval (spiny bollworm); *E. vittella* Fabricius (spotted bollworm); *Egira* (*Xylomyges*) *curialis* Grote (*citrus* cutworm); *Euxoa messoria* Harris (darksided cutworm); *Helicoverpa armigera* Hubner (American bollworm); *H. zea* Boddie (corn earworm or cotton bollworm); *Heliothis virescens* Fabricius (tobacco budworm); *Hypena scabra* Fabricius (green cloverworm); *Hyponeuma taltula* Schaus; (*Mamestra configurata* Walker (bertha armyworm); *M. brassicae* Linnaeus (cabbage moth); *Melanchra picta* Harris (zebra caterpillar); *Mocis latipes* Guenée (small mocis moth); *Pseudaletia unipuncta* Haworth (armyworm); *Pseudoplusia includens* Walker (soybean looper); *Richia albicosta* Smith (Western bean cutworm); *Spodoptera frugiperda* JE Smith (fall armyworm); *S. exigua* Hubner (beet armyworm); *S. litura* Fabricius (tobacco cutworm, cluster caterpillar); *Trichoplusia ni* Hubner (cabbage looper); borers, casebearers, webworms, coneworms, and skeletonizers from the families Pyralidae and Crambidae such as *Achroia grisella* Fabricius (lesser wax moth); *Amyelois transitella* Walker (naval orangeworm); *Anagasta kuehniella* Zeller (Mediterranean flour moth); *Cadra cautella* Walker (almond moth); *Chilo partellus* Swinhoe (spotted stalk borer); *C. suppressalis* Walker (striped stem/rice borer); *C. terrenellus* Pagenstecher (sugarcane stemp borer); *Corcyra cephalonica* Stainton (rice moth); *Crambus caliginosellus* Clemens (corn root webworm); *C. teterrellus Zincken* (bluegrass webworm); *Cnaphalocrocis medinalis* Guenée (rice leaf roller); *Desmia funeralis* Hubner (grape leaffolder); *Diaphania hyalinata* Linnaeus (melon worm); *D. nitidalis* Stoll (pickleworm); *Diatraea flavipennella* Box; *D. grandiosella* Dyar (southwestern corn borer), *D. saccharalis* Fabricius (surgarcane borer); *Elasmopalpus lignosellus* Zeller (lesser cornstalk borer); *Eoreuma loftini* Dyar (Mexican rice borer); *Ephestia elutella* Hubner (tobacco (cacao) moth); *Galleria mellonella* Linnaeus (greater wax moth); *Hedylepta accepta* Butler (sugarcane leafroller); *Herpetogramma licarsisalis* Walker (sod webworm); *Homoeosoma electellum* Hulst (sunflower moth); *Loxostege sticticalis* Linnaeus (beet webworm); *Maruca testulalis* Geyer (bean pod borer); *Orthaga thyrisalis* Walker (tea tree web moth); *Ostrinia nubilalis* Hubner (European corn borer); *Plodia interpunctella* Hubner (Indian meal moth); *Scirpophaga incertulas* Walker (yellow stem borer); *Udea rubigalis* Guenée (celery leaftier); and leafrollers, budworms, seed worms, and fruit worms in the family Tortricidae *Acleris gloverana* Walsingham (Western blackheaded budworm); *A. variana* Fernald (Eastern blackheaded budworm); *Adoxophyes orana* Fischer von Rösslerstamm (summer fruit tortrix moth); *Archips* spp. including *A. argyrospila* Walker (fruit tree leaf roller) and *A. rosana* Linnaeus (European leaf roller); *Argyrotaenia* spp.; *Bonagota salubricola* Meyrick (Brazilian apple leafroller); *Choristoneura* spp.; *Cochylis hospes* Walsingham (banded sunflower moth); *Cydia latiferreana* Walsingham (filbertworm); *C. pomonella* Linnaeus (codling moth); *Endopiza viteana* Clemens (grape berry moth); *Eupoecilia ambiguella* Hubner (vine moth); *Grapholita molesta* Busck (oriental fruit moth); *Lobesia botrana* Denis & Schiffermüller (European grape vine moth); *Platynota flavedana* Clemens (variegated leafroller); *P. stultana* Walsingham (omnivorous leafroller); *Spilonota ocellana* Denis & Schiffermüller (eyespotted bud moth); and *Suleima helianthana* Riley (sunflower bud moth).

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Meneville (Chinese Oak Silkmoth); *Bombyx mori* Linnaeus (Silkworm); *Bucculatrix thurberiella* Busck (cotton leaf perforator); *Collas eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Erechthias flavistriata* Walsingham (sugarcane bud moth); *Euproctis chrysorrhoea* Linnaeus (browntail moth); *Harrisina americana* Guérin-Meneville (grapeleaf skeletonizer); *Heliothis subflexa* Guenée; *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Malacosoma* spp.; *Manduca quinquemaculata* Haworth (five spotted hawk moth, tomato hornworm); *M. sexta* Haworth (tomato hornworm, tobacco hornworm); *Operophtera brumata* Linnaeus (winter moth); *Orgyia* spp.; *Paleacrita vernata* Peck (spring cankerworm); *Papilio cresphontes* Cramer (giant swallowtail orange dog); *Phryganidia californica* Packard (California oakworm); *Phyllocnistis citrella* Stainton (*citrus* leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Telchin licus* Drury (giant sugarcane borer); *Thaumetopoea pityocampa* Schiffermüller (pine processionary caterpillar); *Tineola bisselliella* Hummel (webbing clothesmoth); *Tuta absoluta* Meyrick (tomato leafminer) and *Yponomeuta padella* Linnaeus (ermine moth).

Of interest are larvae and adults of the order Coleoptera including weevils from the families Anthribidae, Bruchidae, and Curculionidae including, but not limited to: *Anthonomus grandis* Boheman (boll weevil); *Cylindrocopturus adspersus* LeConte (sunflower stem weevil); *Diaprepes abbreviatus* Linnaeus (Diaprepes root weevil); *Hypera punctata* Fabricius (clover leaf weevil); *Lissorhoptrus oryzophilus* Kuschel (rice water weevil); *Metamasius hemipterus hemipterus* Linnaeus (West Indian cane weevil); *M. hemipterus* sericeus Olivier (silky cane weevil); *Sitophilus granarius* Linnaeus (granary weevil); *S. oryzae* Linnaeus (rice weevil); *Smicronyx fulvus* LeConte (red sunflower seed weevil); *S. sordidus* LeConte (gray sunflower seed weevil); *Sphenophorus maidis* Chittenden (maize billbug); *S. livis* Vaurie (sugarcane weevil); *Rhabdoscelus obscurus* Boisduval (New Guinea sugarcane weevil); flea beetles, cucumber beetles, rootworms, leaf beetles, potato beetles, and leafminers in the family Chrysomelidae including, but not limited to: *Chaetocnema ectypa* Horn (desert corn flea beetle); *C. pulicaria* Melsheimer (corn flea beetle); *Colaspis brunnea* Fabricius (grape colaspis); *Diabrotica barberi* Smith & Lawrence (northern corn rootworm); *D. undecimpunctata howardi* Barber (southern corn rootworm); *D. virgifera virgifera* LeConte (western corn rootworm); *Leptinotarsa decemlineata* Say (Colorado potato beetle); *Oulema melanopus* Linnaeus (cereal leaf beetle); *Phyllotreta cruciferae* Goeze (corn flea beetle); *Zygogramma exclamationis* Fabricius (sunflower beetle); beetles from the family Coccinellidae including, but not limited to: *Epilachna varivestis* Mulsant (Mexican bean beetle); chafers and other beetles from the family Scarabaeidae including, but not limited to: *Antitrogus parvulus* Britton (Childers cane grub); *Cyclocephala borealis* Arrow (northern masked chafer, white grub); *C. immaculate* Olivier (southern masked chafer, white grub); *Dermolepida albohirtum* Waterhouse (Greyback cane beetle); *Euetheola humilis rugiceps* LeConte (sugarcane beetle); *Lepidiota frenchi* Blackburn (French's cane grub); *Tomarus gibbosus* De Geer (carrot beetle); *T. subtropicus* Blatchley (sugarcane grub); *Phyllophaga crinita* Burmeister (white grub); *P. latifrons* LeConte (June beetle); *Popillia japonica* Newman (Japanese beetle); *Rhizotrogus majalis* Razoumowsky (European chafer); carpet beetles from the family Dermestidae; wireworms from the family Elateridae, *Eleodes* spp., *Melanotus* spp. including *M. communis* Gyllenhal (wireworm); *Conoderus* spp.; *Limonius* spp.; *Agriotes* spp.; *Ctenicera* spp.; *Aeolus* spp.; bark beetles from the family Scolytidae; beetles from the family Tenebrionidae; beetles from the family Cerambycidae such as, but not limited to, *Migdolus fryanus* Westwood (longhorn beetle); and beetles from the Buprestidae family including, but not limited to, *Aphanisticus cochinchinae seminulum* Obenberger (leaf-mining buprestid beetle).

Adults and immatures of the order Diptera are of interest, including leafminers *Agromyza parvicornis* Loew (corn blotch leafminer); midges including, but not limited to: *Contarinia sorghicola* Coquillett (*sorghum* midge); *Mayetiola destructor* Say (Hessian fly); *Neolasioptera murtfeldtiana* Felt, (sunflower seed midge); *Sitodiplosis mosellana* Géhin (wheat midge); fruit flies (Tephritidae), *Oscinella frit* Linnaeus (frit flies); maggots including, but not limited to: *Delia* spp. including *Delia platura* Meigen (seedcorn maggot); *D. coarctata* Fallen (wheat bulb fly); *Fannia canicularis* Linnaeus, *F. femoralis* Stein (lesser house flies); *Meromyza americana* Fitch (wheat stem maggot); *Musca domestica* Linnaeus (house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other *Brachycera*, mosquitoes *Aedes* spp.; *Anopheles* spp.; *Culex* spp.; black flies *Prosimulium* spp.; *Simulium* spp.; biting midges, sand flies, sciarids, and other *Nematocera*.

Included as insects of interest are those of the order Hemiptera such as, but not limited to, the following families: Adelgidae, Aleyrodidae, Aphididae, Asterolecaniidae, Cercopidae, Cicadellidae, Cicadidae, Cixiidae, Coccidae, Coreidae, Dactylopiidae, Delphacidae, Diaspididae, Eriococcidae, Flatidae, Fulgoridae, Issidae, Lygaeidae, Margarodidae, Membracidae, Miridae ortheziidae, Pentatomidae, Phoenicococcidae, Phylloxeridae, Pseudococcidae, Psyllidae, Pyrrhocoridae and Tingidae.

Agronomically important members from the order Hemiptera include, but are not limited to: *Acrosternum hilare* Say (green stink bug); *Acyrthisiphon pisum* Harris (pea aphid); *Adelges* spp. (adelgids); *Adelphocoris rapidus* Say (rapid plant bug); *Anasa tristis* De Geer (squash bug); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacaspis tegalensis* Zehntner (sugarcane scale); *Aulacorthum solani* Kaltenbach (foxglove aphid); *Bemisia tabaci* Gennadius (tobacco whitefly, sweetpotato whitefly); *B. argentifolii* Bellows & Perring (silverleaf whitefly); *Blissus leucopterus leucopterus* Say (chinch bug); *Blostomatidae* spp.; *Brevicoryne brassicae* Linnaeus (cabbage aphid); *Cacopsylla pyricola* Foerster (pear psylla); *Calocoris norvegicus* Gmelin (potato capsid bug); *Chaetosiphon fragaefolii* Cockerell (strawberry aphid); *Cimicidae* spp.; Coreidae spp.; *Corythuca gossypii* Fabricius (cotton lace bug); *Cyrtopeltis modesta* Distant (tomato bug); *C. notatus* Distant (suckfly); *Deois flavopicta* Stål (spittlebug); *Dialeurodes citri* Ashmead (*citrus* whitefly); *Diaphnocoris chlorionis* Say (honeylocust plant bug); *Diuraphis noxia* Kurdjumov/Mordvilko (Russian wheat aphid); *Duplachionaspis divergens* Green (armored scale); *Dysaphis plantaginea* Paaserini (rosy apple aphid); *Dysdercus suturellus* Herrich-Schaffer (cotton stainer); *Dysmicoccus boninsis* Kuwana (gray sugarcane mealybug); *Empoasca fabae* Harris (potato leafhopper); *Eriosoma lanigerum* Hausmann (woolly apple aphid); *Erythroneoura* spp. (grape leafhoppers); *Eumetopina flavipes* Muir (Island sugarcane planthopper); *Eurygaster* spp.; *Euschistus servus* Say (brown stink bug); *E. variolarius* Palisot de Beauvois (one-spotted stink bug); *Graptostethus* spp. (complex of seed bugs); and *Hyalopterus pruni* Geoffroy (mealy plum aphid); *Icerya purchasi* Maskell (cottony cushion scale); *Labopidicola allii* Knight (onion plant bug); *Laodelphax striatellus* Fallen (smaller brown planthopper); *Leptoglossus corculus* Say (leaf-footed pine seed bug); *Leptodictya tabida* Herrich-Schaeffer (sugarcane lace bug); *Lipaphis erysimi* Kaltenbach (turnip aphid); *Lygocoris pabulinus* Linnaeus (common green capsid); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Macrosiphum euphorbiae* Thomas (potato aphid); *Macrosteles quadrilineatus* Forbes (aster leafhopper); *Magicicada septendecim* Linnaeus (periodical cicada); *Mahanarva fimbriolata* Stål (sugarcane spittlebug); *M. posticata* Stål (little cicada of sugarcane);

*Melanaphis sacchari* Zehntner (sugarcane aphid); *Melanaspis glomerata* Green (black scale); *Metopolophium dirhodum* Walker (rose grain aphid); *Myzus persicae* Sulzer (peach-potato aphid, green peach aphid); *Nasonovia ribisnigri* Mosley (lettuce aphid); *Nephotettix cinticeps* Uhler (green leafhopper); *N. nigropictus* Stål (rice leafhopper); *Nezara viridula* Linnaeus (southern green stink bug); *Nilaparvata lugens* Stål (brown planthopper); *Nysius ericae* Schilling (false chinch bug); *Nysius raphanus* Howard (false chinch bug); *Oebalus pugnax* Fabricius (rice stink bug); *Oncopeltus fasciatus* Dallas (large milkweed bug); *Orthops campestris* Linnaeus; *Pemphigus* spp. (root aphids and gall aphids); *Peregrinus maidis* Ashmead (corn planthopper); *Perkinsiella saccharicida* Kirkaldy (sugarcane delphacid); *Phylloxera devastatrix* Pergande (pecan phylloxera); *Planococcus citri* Risso (*citrus* mealybug); *Plesiocoris rugicollis* Fallen (apple capsid); *Poecilocapsus lineatus* Fabricius (four-lined plant bug); *Pseudatomoscelis seriatus* Reuter (cotton fleahopper); *Pseudococcus* spp. (other mealybug complex); *Pulvinaria elongata* Newstead (cottony grass scale); *Pyrilla perpusilla* Walker (sugarcane leafhopper); *Pyrrhocoridae* spp.; *Quadraspidiotus perniciosus* Comstock (San Jose scale); *Reduviidae* spp.; *Rhopalosiphum maidis* Fitch (corn leaf aphid); *R. padi* Linnaeus (bird cherry-oat aphid); *Saccharicoccus sacchari* Cockerell (pink sugarcane mealybug); *Scaptacoris castanea* Perty (brown root stink bug); *Schizaphis graminum* Rondani (greenbug); *Sipha flava* Forbes (yellow sugarcane aphid); *Sitobion avenae* Fabricius (English grain aphid); *Sogatella furcifera* Horvath (white-backed planthopper); *Sogatodes oryzicola* Muir (rice delphacid); *Spanagonicus albofasciatus* Reuter (whitemarked fleahopper); *Therioaphis maculata* Buckton (spotted alfalfa aphid); *Tinidae* spp.; *Toxoptera aurantii* Boyer de Fonscolombe (black *citrus* aphid); and *T. citricida* Kirkaldy (brown *citrus* aphid); *Trialeurodes abutiloneus* (bandedwinged whitefly) and *T. vaporariorum* Westwood (greenhouse whitefly); *Trioza diospyri* Ashmead (persimmon psylla); and *Typhlocyba pomaria* McAtee (white apple leafhopper).

Also included are adults and larvae of the order Acari (mites) such as *Aceria tosichella* Keifer (wheat curl mite); *Panonychus ulmi* Koch (European red mite); *Petrobia latens* Müller (brown wheat mite); *Steneotarsonemus bancrofti* Michael (sugarcane stalk mite); spider mites and red mites in the family Tetranychidae, *Oligonychus grypus* Baker & Pritchard, *O. indicus* Hirst (sugarcane leaf mite), *O. pratensis* Banks (Banks grass mite), *O. stickneyi* McGregor (sugarcane spider mite); *Tetranychus urticae* Koch (two spotted spider mite); *T. mcdanieli* McGregor (McDaniel mite); *T. cinnabarinus* Boisduval (carmine spider mite); *T. turkestani* Ugarov & Nikolski (strawberry spider mite), flat mites in the family Tenuipalpidae, *Brevipalpus lewisi* McGregor (*citrus* flat mite); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch & Mulaik (brown recluse spider); and the *Latrodectus mactans* Fabricius (black widow spider); and centipedes in the order Scutigeromorpha such as *Scutigera coleoptrata* Linnaeus (house centipede). In addition, insect pests of the order Isoptera are of interest, including those of the termitidae family, such as, but not limited to, *Cornitermes cumulans* Kollar, *Cylindrotermes nordenskioeldi* Holmgren and *Pseudacanthotermes militaris* Hagen (sugarcane termite); as well as those in the Rhinotermitidae family including, but not limited to *Heterotermes tenuis* Hagen. Insects of the order Thysanoptera are also of interest, including but not limited to thrips, such as *Stenchaetothrips minutus* van Deventer (sugarcane thrips).

The insect pests can be adults, larvae or even ova. A preferred developmental stage for testing for pesticidal activity is larvae or other immature form of the insect pest. Methods of rearing insect larvae and performing bioassays are well known in the art. See, e.g., Czapla & Lang (1990) *J. Econ. Entomol.* 83:2480-2485; Griffith & Smith (1977) *J. Aust. Ent. Soc.* 16:366; Keiper & Foote (1996) *Hydrobiologia* 339:137-139; and U.S. Pat. No. 5,351,643. For example, insect pests can be reared in total darkness at about 20° C. to about 30° C. and from about 30% to about 70% relative humidity.

The novel chimeric pesticidal polypeptides can exhibit improved pesticidal activity when compared to a pesticidal polypeptide lacking a solubility-enhancing polypeptide. As used herein, the term "improved pesticidal activity" refers to a polypeptide that has enhanced pesticidal activity following the presently disclosed methods relative to the activity of the corresponding pesticidal polypeptide lacking a solubility-enhancing polypeptide as made by the methods disclosed herein and/or to a polypeptide that is effective against a broader range of pests, and/or a polypeptide having specificity for a pest that is not susceptible to the toxicity of the polypeptide prior to modification of its sequence using the presently disclosed methods. A finding of improved or enhanced pesticidal activity requires a demonstration of an increase of pesticidal activity of at least 10%, against the pest target or at least 20%, 25%, 30%, 35%, 40%, 45%, 50%, 60%, 70%, 100%, 150%, 200% or 300% or greater increase of pesticidal activity relative to the pesticidal activity of the polypeptide prior to the addition of a solubility-enhancing polypeptide, as determined against the same pest.

For example, an improved pesticidal activity is provided where a wider or narrower range of pests is impacted by the polypeptide relative to the range of pests that is affected by the polypeptide prior to sequence modification. A wider range of impact may be desirable where versatility is desired, while a narrower range of impact may be desirable where, for example, beneficial insects might otherwise be impacted by use or presence of the pesticidal polypeptide. While the invention is not bound by any particular mechanism of action, an improved pesticidal activity may also be provided by changes in one or more characteristics of a polypeptide; for example, the stability or longevity of a polypeptide in an insect gut may be increased relative to the stability or longevity of a corresponding wild-type protein.

A "subject plant or plant cell" is one in which genetic alteration, such as transformation, has been affected as to a gene of interest or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

As noted above, the methods involve generating novel chimeric pesticidal polypeptide sequences and the nucleotide sequences that encode such polypeptides. The novel chimeric pesticidal polypeptide sequences are produced by making a fusion protein comprising an amino acid sequence of a solubility-enhancing polypeptide operably linked to an amino acid sequence of a pesticidal protein, particularly a cry protein.

Any pesticidal protein can be used in the presently disclosed methods. In some embodiments, the pesticidal protein is a δ-endotoxin of *Bacillus* spp. The specific activity of δ-endotoxins is considered highly beneficial. Unlike most insecticides, the δ-endotoxins do not have a broad spectrum of activity, so they typically do not kill beneficial insects. Furthermore, the δ-endotoxins are non-toxic to mammals, including humans, domesticated animals, and wildlife. In particular embodiments, the δ-endotoxin is a Cry protein.

It is well known that naturally occurring δ-endotoxins are synthesized by *B. thuringiensis* sporulating cells as a proteinaceous crystalline inclusion protoxin. Upon being ingested by susceptible insect larvae, the microcrystals dissolve in the midgut, and the protoxin is transformed into a biologically active moiety by proteases characteristic of digestive enzymes located in the insect gut. The activated δ-endotoxin binds with high affinity to protein receptors on brush-border membrane vesicles. The epithelial cells lining the midgut are the primary target of the endotoxin and are rapidly destroyed as a consequence of membrane perforation resulting from the formation of gated, cation-selective channels by the toxin. Both Cry and Cyt toxins are pore-forming toxins. The α-helix regions of the Cry toxins form the trans-membrane pore, whereas Cyt toxins insert into the membrane by forming a β-barrel comprised of β-sheets from each monomer.

Bt Cry proteins have five conserved sequence domains, and three conserved structural domains (see, e.g., de Maagd et al. (2001) *Trends Genetics* 17:193-199). The most amino-terminal conserved structural domain (Domain I) consists of seven alpha helices, with a central hydrophobic helix-α5 encircled by six other amphipathic helices, and is involved in membrane insertion and pore formation. The second conserved structural domain (Domain II) consists of three antiparallel beta-sheets implicated in cell binding, and the most carboxy-terminal conserved structural domain (Domain III) consists of a beta-sandwich. Exposed regions in domains II and III are involved in receptor recognition and binding, and are therefore considered determinants of toxin specificity. The location and properties of these domains are known to those of skill in the art. See, for example, Grochulski et al. (1995) *J Mol Biol* 254:447-464; Morse, Yamamoto, and Stroud (2001) *Structure* 9:409-417; Li et al. (1991) *Nature* 353:815-821; Galitsky et al. (2001) *Acta Cryst* D57:1101-1109; Boonserm et al. (2006) *J Bacteriol* 188:3391-3401; Boonserm et al. (2005) *J Mol Biol* 348:363-382; and Guo et al. (2009) *J Struct Biol* 168:259-266.

Bt Cyt proteins have a single α-β domain comprising two outer layers of α-helix hairpins wrapped around a β-sheet (Li, Koni, and Ellar (1996) *J Mol Biol* 257:129-152; and Cohen et al. (2008) *J Mol Biol* 380:820-827). The β-sheet is involved in membrane insertion.

A list of some known δ-endotoxins (Cry and Cyt endotoxins) and their GenBank Accession Nos. are listed in Table 2, which can be used as a source for nucleic and amino acid sequences for use in the methods disclosed herein.

TABLE 2

| Endotoxin | Accession # | Endotoxin | Accession # |
|---|---|---|---|
| Cry1Aa1 | AAA22353 | Cry1Aa2 | AAA22552 |
| Cry1Aa3 | BAA00257 | Cry1Aa4 | CAA31886 |
| Cry1Aa5 | BAA04468 | Cry1Aa6 | AAA86265 |
| Cry1Aa7 | AAD46139 | Cry1Aa8 | I26149 |
| Cry1Aa9 | BAA77213 | Cry1Aa10 | AAD55382 |
| Cry1Aa11 | CAA70856 | Cry1Aa12 | AAP80146 |
| Cry1Aa13 | AAM44305 | Cry1Aa14 | AAP40639 |
| Cry1Aa15 | AAY66993 | Cry1Aa16 | HQ439776 |
| Cry1Aa17 | HQ439788 | Cry1Aa18 | HQ439790 |
| Cry1Aa19 | HQ685121 | Cry1Aa20 | JF340156 |
| Cry1Aa21 | JN651496 | Cry1Aa22 | KC158223 |
| Cry1Ab1 | AAA22330 | Cry1Ab2 | AAA22613 |
| Cry1Ab3 | AAA22561 | Cry1Ab4 | BAA00071 |
| Cry1Ab5 | CAA28405 | Cry1Ab6 | AAA22420 |
| Cry1Ab7 | CAA31620 | Cry1Ab8 | AAA22551 |
| Cry1Ab9 | CAA38701 | Cry1Ab10 | A29125 |
| Cry1Ab11 | I12419 | Cry1Ab12 | AAC64003 |
| Cry1Ab13 | AAN76494 | Cry1Ab14 | AAG16877 |
| Cry1Ab15 | AAO13302 | Cry1Ab16 | AAK55546 |
| Cry1Ab17 | AAT46415 | Cry1Ab18 | AAQ88259 |
| Cry1Ab19 | AAW31761 | Cry1Ab20 | ABB72460 |
| Cry1Ab21 | ABS18384 | Cry1Ab22 | ABW87320 |
| Cry1Ab23 | HQ439777 | Cry1Ab24 | HQ439778 |
| Cry1Ab25 | HQ685122 | Cry1Ab26 | HQ847729 |
| Cry1Ab27 | JN135249 | Cry1Ab28 | JN135250 |
| Cry1Ab29 | JN135251 | Cry1Ab30 | JN135252 |
| Cry1Ab31 | JN135253 | Cry1Ab32 | JN135254 |
| Cry1Ab33 | AAS93798 | Cry1Ab34 | KC156668 |
| Cry1Ab-like | AAK14336 | Cry1Ab-like | AAK14337 |
| Cry1Ab-like | AAK14338 | Cry1Ab-like | ABG88858 |
| Cry1Ac1 | AAA22331 | Cry1Ac2 | AAA22338 |
| Cry1Ac3 | CAA38098 | Cry1Ac4 | Cry1Ac4 |
| Cry1Ac5 | AAA22339 | Cry1Ac6 | AAA86266 |
| Cry1Ac7 | AAB46989 | Cry1Ac8 | AAC44841 |
| Cry1Ac9 | AAB49768 | Cry1Ac10 | CAA05505 |
| Cry1Ac11 | CAA10270 | Cry1Ac12 | I12418 |
| Cry1Ac13 | AAD38701 | Cry1Ac14 | AAQ06607 |
| Cry1Ac15 | AAN07788 | Cry1Ac16 | AAU87037 |
| Cry1Ac17 | AAX18704 | Cry1Ac18 | AAY88347 |
| Cry1Ac19 | ABD37053 | Cry1Ac20 | ABB89046 |
| Cry1Ac21 | AAY66992 | Cry1Ac22 | ABZ01836 |
| Cry1Ac23 | CAQ30431 | Cry1Ac24 | ABL01535 |
| Cry1Ac25 | FJ513324 | Cry1Ac26 | FJ617446 |
| Cry1Ac27 | FJ617447 | Cry1Ac28 | ACM90319 |
| Cry1Ac29 | DQ438941 | Cry1Ac30 | GQ227507 |
| Cry1Ac31 | GU446674 | Cry1Ac32 | HM061081 |
| Cry1Ac33 | GQ866913 | Cry1Ac34 | HQ230364 |
| Cry1Ac35 | JF340157 | Cry1Ac36 | JN387137 |
| Cry1Ac37 | JQ317685 | Cry1Ad1 | AAA22340 |
| Cry1Ad2 | CAA01880 | Cry1Ae1 | AAA22410 |
| Cry1Af1 | AAB82749 | Cry1Ag1 | AAD46137 |
| Cry1Ah1 | AAQ14326 | Cry1Ah2 | ABB76664 |
| Cry1Ah3 | HQ439779 | Cry1Ai1 | AAO39719 |
| Cry1Ai2 | HQ439780 | Cry1A-like | AAK14339 |
| Cry1Ba1 | CAA29898 | Cry1Ba2 | CAA65003 |
| Cry1Ba3 | AAK63251 | Cry1Ba4 | AAK51084 |
| Cry1Ba5 | ABO20894 | Cry1Ba6 | ABL60921 |
| Cry1Ba7 | HQ439781 | Cry1Bb1 | AAA22344 |
| Cry1Bb2 | HQ439782 | Cry1Bc1 | CAA86568 |
| Cry1Bd1 | AAD10292 | Cry1Bd2 | AAM93496 |
| Cry1Be1 | AAC32850 | Cry1Be2 | AAQ52387 |
| Cry1Be3 | ACV96720 | Cry1Be4 | HM070026 |
| Cry1Bf1 | CAC50778 | Cry1Bf2 | AAQ52380 |
| Cry1Bg1 | AAO39720 | Cry1Bh1 | HQ589331 |
| Cry1Bi1 | KC156700 | Cry1Ca1 | CAA30396 |
| Cry1Ca2 | CAA31951 | Cry1Ca3 | AAA22343 |

TABLE 2-continued

| Endotoxin | Accession # | Endotoxin | Accession # |
|---|---|---|---|
| Cry1Ca4 | CAA01886 | Cry1Ca5 | CAA65457 |
| Cry1Ca6 | AAF37224 | Cry1Ca7 | AAG50438 |
| Cry1Ca8 | AAM00264 | Cry1Ca9 | AAL79362 |
| Cry1Ca10 | AAN16462 | Cry1Ca11 | AAX53094 |
| Cry1Ca12 | HM070027 | Cry1Ca13 | HQ412621 |
| Cry1Ca14 | JN651493 | Cry1Cb1 | M97880 |
| Cry1Cb2 | AAG35409 | Cry1Cb3 | ACD50894 |
| Cry1Cb-like | AAX63901 | Cry1Da1 | CAA38099 |
| Cry1Da2 | I76415 | Cry1Da3 | HQ439784 |
| Cry1Db1 | CAA80234 | Cry1Db2 | AAK48937 |
| Cry1Dc1 | ABK35074 | Cry1Ea1 | CAA37933 |
| Cry1Ea2 | CAA39609 | Cry1Ea3 | AAA22345 |
| Cry1Ea4 | AAD04732 | Cry1Ea5 | A15535 |
| Cry1Ea6 | AAL50330 | Cry1Ea7 | AAW72936 |
| Cry1Ea8 | ABX11258 | Cry1Ea9 | HQ439785 |
| Cry1Ea10 | ADR00398 | Cry1Ea11 | JQ652456 |
| Cry1Eb1 | AAA22346 | Cry1Fa1 | AAA22348 |
| Cry1Fa2 | AAA22347 | Cry1Fa3 | HM070028 |
| Cry1Fa4 | HM439638 | Cry1Fb1 | CAA80235 |
| Cry1Fb2 | BAA25298 | Cry1Fb3 | AAF21767 |
| Cry1Fb4 | AAC10641 | Cry1Fb5 | AAO13295 |
| Cry1Fb6 | ACD50892 | Cry1Fb7 | ACD50893 |
| Cry1Ga1 | CAA80233 | Cry1Ga2 | CAA70506 |
| Cry1Gb1 | AAD10291 | Cry1Gb2 | AAO13756 |
| Cry1Gc1 | AAQ52381 | Cry1Ha1 | CAA80236 |
| Cry1Hb1 | AAA79694 | Cry1Hb2 | HQ439786 |
| Cry1H-like | AAF01213 | Cry1Ia1 | CAA44633 |
| Cry1Ia2 | AAA22354 | Cry1Ia3 | AAC36999 |
| Cry1Ia4 | AAB00958 | Cry1Ia5 | CAA70124 |
| Cry1Ia6 | AAC26910 | Cry1Ia7 | AAM73516 |
| Cry1Ia8 | AAK66742 | Cry1Ia9 | AAQ08616 |
| Cry1Ia10 | AAP86782 | Cry1Ia11 | CAC85964 |
| Cry1Ia12 | AAV53390 | Cry1Ia13 | ABF83202 |
| Cry1Ia14 | ACG63871 | Cry1Ia15 | FJ617445 |
| Cry1Ia16 | FJ617448 | Cry1Ia17 | GU989199 |
| Cry1Ia18 | ADK23801 | Cry1Ia19 | HQ439787 |
| Cry1Ia20 | JQ228426 | Cry1Ia21 | JQ228424 |
| Cry1Ia22 | JQ228427 | Cry1Ia23 | JQ228428 |
| Cry1Ia24 | JQ228429 | Cry1Ia25 | JQ228430 |
| Cry1Ia26 | JQ228431 | Cry1Ia27 | JQ228432 |
| Cry1Ia28 | JQ228433 | Cry1Ia29 | JQ228434 |
| Cry1Ia30 | JQ317686 | Cry1Ia31 | JX944038 |
| Cry1Ia32 | JX944039 | Cry1Ia33 | JX944040 |
| Cry1Ib1 | AAA82114 | Cry1Ib2 | ABW88019 |
| Cry1Ib3 | ACD75515 | Cry1Ib4 | HM051227 |
| Cry1Ib5 | HM070028 | Cry1Ib6 | ADK38579 |
| Cry1Ib7 | JN571740 | Cry1Ib8 | JN675714 |
| Cry1Ib9 | JN675715 | Cry1Ib10 | JN675716 |
| Cry1Ib11 | JQ228423 | Cry1Ic1 | AAC62933 |
| Cry1Ic2 | AAE71691 | Cry1Id1 | AAD44366 |
| Cry1Id2 | JQ228422 | Cry1Ie1 | AAG43526 |
| Cry1Ie2 | HM439636 | Cry1Ie3 | KC156647 |
| Cry1Ie4 | KC156681 | Cry1If1 | AAQ52382 |
| Cry1Ig1 | KC156701 | Cry1I-like | AAC31094 |
| Cry1I-like | ABG88859 | Cry1Ja1 | AAA22341 |
| Cry1Ja2 | HM070030 | Cry1Ja3 | JQ228425 |
| Cry1Jb1 | AAA98959 | Cry1Jc1 | AAC31092 |
| Cry1Jc2 | AAQ52372 | Cry1Jd1 | CAC50779 |
| Cry1Ka1 | AAB00376 | Cry1Ka2 | HQ439783 |
| Cry1La1 | AAS60191 | Cry1La2 | HM070031 |
| Cry1Ma1 | FJ884067 | Cry1Ma2 | KC156659 |
| Cry1Na1 | KC156648 | Cry1Nb1 | KC156678 |
| Cry1-like | AAC31091 | Cry2Aa1 | AAA22335 |
| Cry2Aa2 | AAA83516 | Cry2Aa3 | D86064 |
| Cry2Aa4 | AAC04867 | Cry2Aa5 | CAA10671 |
| Cry2Aa6 | CAA10672 | Cry2Aa7 | CAA10670 |
| Cry2Aa8 | AAO13734 | Cry2Aa9 | AAO13750 |
| Cry2Aa10 | AAQ04263 | Cry2Aa11 | AAQ52384 |
| Cry2Aa12 | ABI83671 | Cry2Aa13 | ABL01536 |
| Cry2Aa14 | ACF04939 | Cry2Aa15 | JN426947 |
| Cry2Ab1 | AAA22342 | Cry2Ab2 | CAA39075 |
| Cry2Ab3 | AAG36762 | Cry2Ab4 | AAO13296 |
| Cry2Ab5 | AAQ04609 | Cry2Ab6 | AAP59457 |
| Cry2Ab7 | AAZ66347 | Cry2Ab8 | ABC95996 |
| Cry2Ab9 | ABC74968 | Cry2Ab10 | EF157306 |
| Cry2Ab11 | CAM84575 | Cry2Ab12 | ABM21764 |
| Cry2Ab13 | ACG76120 | Cry2Ab14 | ACG76121 |
| Cry2Ab15 | HM037126 | Cry2Ab16 | GQ866914 |

TABLE 2-continued

| Endotoxin | Accession # | Endotoxin | Accession # |
|---|---|---|---|
| Cry2Ab17 | HQ439789 | Cry2Ab18 | JN135255 |
| Cry2Ab19 | JN135256 | Cry2Ab20 | JN135257 |
| Cry2Ab21 | JN135258 | Cry2Ab22 | JN135259 |
| Cry2Ab23 | JN135260 | Cry2Ab24 | JN135261 |
| Cry2Ab25 | JN415485 | Cry2Ab26 | JN426946 |
| Cry2Ab27 | JN415764 | Cry2Ab28 | JN651494 |
| Cry2Ac1 | CAA40536 | Cry2Ac2 | AAG35410 |
| Cry2Ac3 | AAQ52385 | Cry2Ac4 | ABC95997 |
| Cry2Ac5 | ABC74969 | Cry2Ac6 | ABC74793 |
| Cry2Ac7 | CAL18690 | Cry2Ac8 | CAM09325 |
| Cry2Ac9 | CAM09326 | Cry2Ac10 | ABN15104 |
| Cry2Ac11 | CAM83895 | Cry2Ac12 | CAM83896 |
| Cry2Ad1 | AAF09583 | Cry2Ad2 | ABC86927 |
| Cry2Ad3 | CAK29504 | Cry2Ad4 | CAM32331 |
| Cry2Ad5 | CAO78739 | Cry2Ae1 | AAQ52362 |
| Cry2Af1 | ABO30519 | Cry2Af2 | GQ866915 |
| Cry2Ag1 | ACH91610 | Cry2Ah1 | EU939453 |
| Cry2Ah2 | ACL80665 | Cry2Ah3 | GU073380 |
| Cry2Ah4 | KC156702 | Cry2Ai1 | FJ788388 |
| Cry2Aj | | Cry2Ak1 | KC156660 |
| Cry2Ba1 | KC156658 | Cry3Aa1 | AAA22336 |
| Cry3Aa2 | AAA22541 | Cry3Aa3 | CAA68482 |
| Cry3Aa4 | AAA22542 | Cry3Aa5 | AAA50255 |
| Cry3Aa6 | AAC43266 | Cry3Aa7 | CAB41411 |
| Cry3Aa8 | AAS79487 | Cry3Aa9 | AAW05659 |
| Cry3Aa10 | AAU29411 | Cry3Aa11 | AAW82872 |
| Cry3Aa12 | ABY49136 | Cry3Ba1 | CAA34983 |
| Cry3Ba2 | CAA00645 | Cry3Ba3 | JQ397327 |
| Cry3Bb1 | AAA22334 | Cry3Bb2 | AAA74198 |
| Cry3Bb3 | I15475 | Cry3Ca1 | CAA42469 |
| Cry4Aa1 | CAA68485 | Cry4Aa2 | BAA00179 |
| Cry4Aa3 | CAD30148 | Cry4Aa4 | AFB18317 |
| Cry4A-like | AAY96321 | Cry4Ba1 | CAA30312 |
| Cry4Ba2 | CAA30114 | Cry4Ba3 | AAA22337 |
| Cry4Ba4 | BAA00178 | Cry4Ba5 | CAD30095 |
| Cry4Ba-like | ABC47686 | Cry4Ca1 | EU646202 |
| Cry4Cb1 | FJ403208 | Cry4Cb2 | FJ597622 |
| Cry4Cc1 | FJ403207 | Cry5Aa1 | AAA67694 |
| Cry5Ab1 | AAA67693 | Cry5Ac1 | I34543 |
| Cry5Ad1 | ABQ82087 | Cry5Ba1 | AAA68598 |
| Cry5Ba2 | ABW88931 | Cry5Ba3 | AFJ04417 |
| Cry5Ca1 | HM461869 | Cry5Ca2 | ZP_04123426 |
| Cry5Da1 | HM461870 | Cry5Da2 | ZP_04123980 |
| Cry5Ea1 | HM485580 | Cry5Ea2 | ZP_04124038 |
| Cry6Aa1 | AAA22357 | Cry6Aa2 | AAM46849 |
| Cry6Aa3 | ABH03377 | Cry6Ba1 | AAA22358 |
| Cry7Aa1 | AAA22351 | Cry7Ab1 | AAA21120 |
| Cry7Ab2 | AAA21121 | Cry7Ab3 | ABX24522 |
| Cry7Ab4 | EU380678 | Cry7Ab5 | ABX79555 |
| Cry7Ab6 | ACI44005 | Cry7Ab7 | ADB89216 |
| Cry7Ab8 | GU145299 | Cry7Ab9 | ADD92572 |
| Cry7Ba1 | ABB70817 | Cry7Bb1 | KC156653 |
| Cry7Ca1 | ABR67863 | Cry7Cb1 | KC156698 |
| Cry7Da1 | ACQ99547 | Cry7Da2 | HM572236 |
| Cry7Da3 | KC156679 | Cry7Ea1 | HM035086 |
| Cry7Ea2 | HM132124 | Cry7Ea3 | EEM19403 |
| Cry7Fa1 | HM035088 | Cry7Fa2 | EEM19090 |
| Cry7Fb1 | HM572235 | Cry7Fb2 | KC156682 |
| Cry7Ga1 | HM572237 | Cry7Ga2 | KC156669 |
| Cry7Gb1 | KC156650 | Cry7Gc1 | KC156654 |
| Cry7Gd1 | KC156697 | Cry7Ha1 | KC156651 |
| Cry7Ia1 | KC156665 | Cry7Ja1 | KC156671 |
| Cry7Ka1 | KC156680 | Cry7Kb1 | BAM99306 |
| Cry7La1 | BAM99307 | Cry8Aa1 | AAA21117 |
| Cry8Ab1 | EU044830 | Cry8Ac1 | KC156662 |
| Cry8Ad1 | KC156684 | Cry8Ba1 | AAA21118 |
| Cry8Bb1 | CAD57542 | Cry8Bc1 | CAD57543 |
| Cry8Ca1 | AAA21119 | Cry8Ca2 | AAR98783 |
| Cry8Ca3 | EU625349 | Cry8Ca4 | ADB54826 |
| Cry8Da1 | BAC07226 | Cry8Da2 | BD133574 |
| Cry8Da3 | BD133575 | Cry8Db1 | BAF93483 |
| Cry8Ea1 | AAQ73470 | Cry8Ea2 | EU047597 |
| Cry8Ea3 | KC855216 | Cry8Fa1 | AAT48690 |
| Cry8Fa2 | HQ174208 | Cry8Fa3 | AFH78109 |
| Cry8Ga1 | AAT46073 | Cry8Ga2 | ABC42043 |
| Cry8Ga3 | FJ198072 | Cry8Ha1 | AAW81032 |
| Cry8Ia1 | EU381044 | Cry8Ia2 | GU073381 |
| Cry8Ia3 | HM044664 | Cry8Ia4 | KC156674 |

TABLE 2-continued

| Endotoxin | Accession # | Endotoxin | Accession # |
|---|---|---|---|
| Cry8Ib1 | GU325772 | Cry8Ib2 | KC156677 |
| Cry8Ja1 | EU625348 | Cry8Ka1 | FJ422558 |
| Cry8Ka2 | ACN87262 | Cry8Kb1 | HM123758 |
| Cry8Kb2 | KC156675 | Cry8La1 | GU325771 |
| Cry8Ma1 | HM044665 | Cry8Ma2 | EEM86551 |
| Cry8Ma3 | HM210574 | Cry8Na1 | HM640939 |
| Cry8Pa1 | HQ388415 | Cry8Qa1 | HQ441166 |
| Cry8Qa2 | KC152468 | Cry8Ra1 | AFP87548 |
| Cry8Sa1 | JQ740599 | Cry8Ta1 | KC156673 |
| Cry8-like | FJ770571 | Cry8-like | ABS53003 |
| Cry9Aa1 | CAA41122 | Cry9Aa2 | CAA41425 |
| Cry9Aa3 | GQ249293 | Cry9Aa4 | GQ249294 |
| Cry9Aa5 | JX174110 | Cry9Aa like | AAQ52376 |
| Cry9Ba1 | CAA52927 | Cry9Ba2 | GU299522 |
| Cry9Bb1 | AAV28716 | Cry9Ca1 | CAA85764 |
| Cry9Ca2 | AAQ52375 | Cry9Da1 | BAA19948 |
| Cry9Da2 | AAB97923 | Cry9Da3 | GQ249293 |
| Cry9Da4 | GQ249297 | Cry9Db1 | AAX78439 |
| Cry9Dc1 | KC156683 | Cry9Ea1 | BAA34908 |
| Cry9Ea2 | AAO12908 | Cry9Ea3 | ABM21765 |
| Cry9Ea4 | ACE88267 | Cry9Ea5 | ACF04743 |
| Cry9Ea6 | ACG63872 | Cry9Ea7 | FJ380927 |
| Cry9Ea8 | GQ249292 | Cry9Ea9 | JN651495 |
| Cry9Eb1 | CAC50780 | Cry9Eb2 | GQ249298 |
| Cry9Eb3 | KC156646 | Cry9Ec1 | AAC63366 |
| Cry9Ed1 | AAX78440 | Cry9Ee1 | GQ249296 |
| Cry9Ee2 | KC156664 | Cry9Fa1 | KC156692 |
| Cry9Ga1 | KC156699 | Cry9-like | AAC63366 |
| Cry10Aa1 | AAA22614 | Cry10Aa2 | E00614 |
| Cry10Aa3 | CAD30098 | Cry10Aa4 | AFB18318 |
| Cry10A-like | DQ167578 | Cry11Aa1 | AAA22352 |
| Cry11Aa2 | AAA22611 | Cry11Aa3 | CAD30081 |
| Cry11Aa4 | AFB18319 | Cry11Aa-like | DQ166531 |
| Cry11Ba1 | CAA60504 | Cry11Bb1 | AAC97162 |
| Cry11Bb2 | HM068615 | Cry12Aa1 | AAA22355 |
| Cry13Aa1 | AAA22356 | Cry14Aa1 | AAA21516 |
| Cry14Ab1 | KC156652 | Cry15Aa1 | AAA22333 |
| Cry16Aa1 | CAA63860 | Cry17Aa1 | CAA67841 |
| Cry18Aa1 | CAA67506 | Cry18Ba1 | AAF89667 |
| Cry18Ca1 | AAF89668 | Cry19Aa1 | CAA68875 |
| Cry19Ba1 | BAA32397 | Cry19Ca1 | AFM37572 |
| Cry20Aa1 | AAB93476 | Cry20Ba1 | ACS93601 |
| Cry20Ba2 | KC156694 | Cry20-like | GQ144333 |
| Cry21Aa1 | I32932 | Cry21Aa2 | I66477 |
| Cry21Ba1 | BAC06484 | Cry21Ca1 | JF521577 |
| Cry21Ca2 | KC156687 | Cry21Da1 | JF521578 |
| Cry22Aa1 | I34547 | Cry22Aa2 | CAD43579 |
| Cry22Aa3 | ACD93211 | Cry22Ab1 | AAK50456 |
| Cry22Ab2 | CAD43577 | Cry22Ba1 | CAD43578 |
| Cry22Bb1 | KC156672 | Cry23Aa1 | AAF76375 |
| Cry24Aa1 | AAC61891 | Cry24Ba1 | BAD32657 |
| Cry24Ca1 | CAJ43600 | Cry25Aa1 | AAC61892 |
| Cry26Aa1 | AAD25075 | Cry27Aa1 | BAA82796 |
| Cry28Aa1 | AAD24189 | Cry28Aa2 | AAG00235 |
| Cry29Aa1 | CAC80985 | Cry30Aa1 | CAC80986 |
| Cry30Ba1 | BAD00052 | Cry30Ca1 | BAD67157 |
| Cry30Ca2 | ACU24781 | Cry30Da1 | EF095955 |
| Cry30Db1 | BAE80088 | Cry30Ea1 | ACC95445 |
| Cry30Ea2 | FJ499389 | Cry30Fa1 | ACI22625 |
| Cry30Ga1 | ACG60020 | Cry30Ga2 | HQ638217 |
| Cry31Aa1 | BAB11757 | Cry31Aa2 | AAL87458 |
| Cry31Aa3 | BAE79808 | Cry31Aa4 | BAF32571 |
| Cry31Aa5 | BAF32572 | Cry31Aa6 | BAI44026 |
| Cry31Ab1 | BAE79809 | Cry31Ab2 | BAF32570 |
| Cry31Ac1 | BAF34368 | Cry31Ac2 | AB731600 |
| Cry31Ad1 | BAI44022 | Cry32Aa1 | AAG36711 |
| Cry32Aa2 | GU063849 | Cry32Ab1 | GU063850 |
| Cry32Ba1 | BAB78601 | Cry32Ca1 | BAB78602 |
| Cry32Cb1 | KC156708 | Cry32Da1 | BAB78603 |
| Cry32Ea1 | GU324274 | Cry32Ea2 | KC156686 |
| Cry32Eb1 | KC156663 | Cry32Fa1 | KC156656 |
| Cry32Ga1 | KC156657 | Cry32Ha1 | KC156661 |
| Cry32Hb1 | KC156666 | Cry32Ia1 | KC156667 |
| Cry32Ja1 | KC156685 | Cry32Ka1 | KC156688 |
| Cry32La1 | KC156689 | Cry32Ma1 | KC156690 |
| Cry32Mb1 | KC156704 | Cry32Na1 | KC156691 |
| Cry32Oa1 | KC156703 | Cry32Pa1 | KC156705 |
| Cry32Qa1 | KC156706 | Cry32Ra1 | KC156707 |

TABLE 2-continued

| Endotoxin | Accession # | Endotoxin | Accession # |
|---|---|---|---|
| Cry32Sa1 | KC156709 | Cry32Ta1 | KC156710 |
| Cry32Ua1 | KC156655 | Cry33Aa1 | AAL26871 |
| Cry34Aa1 | AAG50341 | Cry34Aa2 | AAK64560 |
| Cry34Aa3 | AAT29032 | Cry34Aa4 | AAT29030 |
| Cry34Ab1 | AAG41671 | Cry34Ac1 | AAG50118 |
| Cry34Ac2 | AAK64562 | Cry34Ac3 | AAT29029 |
| Cry34Ba1 | AAK64565 | Cry34Ba2 | AAT29033 |
| Cry34Ba3 | AAT29031 | Cry35Aa1 | AAG50342 |
| Cry35Aa2 | AAK64561 | Cry35Aa3 | AAT29028 |
| Cry35Aa4 | AAT29025 | Cry35Ab1 | AAG41672 |
| Cry35Ab2 | AAK64563 | Cry35Ab3 | AY536891 |
| Cry35Ac1 | AAG50117 | Cry35Ba1 | AAK64566 |
| Cry35Ba2 | AAT29027 | Cry35Ba3 | AAT29026 |
| Cry36Aa1 | AAK64558 | Cry37Aa1 | AAF76376 |
| Cry38Aa1 | AAK64559 | Cry39Aa1 | BAB72016 |
| Cry40Aa1 | BAB72018 | Cry40Ba1 | BAC77648 |
| Cry40Ca1 | EU381045 | Cry40Da1 | ACF15199 |
| Cry41Aa1 | BAD35157 | Cry41Ab1 | BAD35163 |
| Cry41Ba1 | HM461871 | Cry41Ba2 | ZP_04099652 |
| Cry42Aa1 | BAD35166 | Cry43Aa1 | BAD15301 |
| Cry43Aa2 | BAD95474 | Cry43Ba1 | BAD15303 |
| Cry43Ca1 | KC156676 | Cry43Cb1 | KC156695 |
| Cry43Cc1 | KC156696 | Cry43-like | BAD15305 |
| Cry44Aa | Cry44Aa | Cry45Aa | BAD22577 |
| Cry46Aa | BAC79010 | Cry46Aa2 | BAG68906 |
| Cry46Ab | BAD35170 | Cry47Aa | AAY24695 |
| Cry48Aa | CAJ18351 | Cry48Aa2 | CAJ86545 |
| Cry48Aa3 | CAJ86546 | Cry48Ab | CAJ86548 |
| Cry48Ab2 | CAJ86549 | Cry49Aa | CAH56541 |
| Cry49Aa2 | CAJ86541 | Cry49Aa3 | CAJ86543 |
| Cry49Aa4 | CAJ86544 | Cry49Ab1 | CAJ86542 |
| Cry50Aa1 | BAE86999 | Cry50Ba1 | GU446675 |
| Cry50Ba2 | GU446676 | Cry51Aa1 | ABI14444 |
| Cry51Aa2 | GU570697 | Cry52Aa1 | EF613489 |
| Cry52Ba1 | FJ361760 | Cry53Aa1 | EF633476 |
| Cry53Ab1 | FJ361759 | Cry54Aa1 | ACA52194 |
| Cry54Aa2 | GQ140349 | Cry54Ba1 | GU446677 |
| Cry55Aa1 | ABW88932 | Cry54Ab1 | JQ916908 |
| Cry55Aa2 | AAE33526 | Cry56Aa1 | ACU57499 |
| Cry56Aa2 | GQ483512 | Cry56Aa3 | JX025567 |
| Cry57Aa1 | ANC87261 | Cry58Aa1 | ANC87260 |
| Cry59Ba1 | JN790647 | Cry59Aa1 | ACR43758 |
| Cry60Aa1 | ACU24782 | Cry60Aa2 | EAO57254 |
| Cry60Aa3 | EEM99278 | Cry60Ba1 | GU810818 |
| Cry60Ba2 | EAO57253 | Cry60Ba3 | EEM99279 |
| Cry61Aa1 | HM035087 | Cry61Aa2 | HM132125 |
| Cry61Aa3 | EEM19308 | Cry62Aa1 | HM054509 |
| Cry63Aa1 | BAI44028 | Cry64Aa1 | BAJ05397 |
| Cry65Aa1 | HM461868 | Cry65Aa2 | ZP_04123838 |
| Cry66Aa1 | HM485581 | Cry66Aa2 | ZP_04099945 |
| Cry67Aa1 | HM485582 | Cry67Aa2 | ZP_04148882 |
| Cry68Aa1 | HQ113114 | Cry69Aa1 | HQ401006 |
| Cry69Aa2 | JQ821388 | Cry69Ab1 | JN209957 |
| Cry70Aa1 | JN646781 | Cry70Ba1 | ADO51070 |
| Cry70Bb1 | EEL67276 | Cry71Aa1 | JX025568 |
| Cry72Aa1 | JX025569 | Cyt1Aa | X03182 |
| Cyt1Ab | X98793 | Cyt1B | U37196 |
| Cyt2A | Z14147 | Cyt2B | U52043 |

* The amino acid and corresponding nucleotide sequences of the accession numbers in Table 2 are herein incorporated by reference.

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of cry proteins such as Cry1A, Cry3A) of U.S. Pat. Nos. 8,304,604, 8,304,605 and 8,476,226; Cry1B of U.S. patent application Ser. No. 10/525,318; Cry1C of U.S. Pat. No. 6,033,874; Cry1F of U.S. Pat. Nos. 5,188,960 and 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476, 781, 7,105,332, 7,378,499 and 7,462,760; a Cry9 protein such as such as members of the Cry9A, Cry9B, Cry9C, Cry9D, Cry9E and Cry9F families; a Cry15 protein of Naimov, et al., (2008) *Applied and Environmental Microbiology,* 74:7145-7151; a Cry22, a Cry34Ab1 protein of U.S. Pat. Nos. 6,127,180, 6,624,145 and 6,340,593; a CryET33 and cryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US Patent Application Publication Number 2008/0295207; ET29, ET37, TIC809, TIC810, TIC812, TIC127, TIC128 of PCT US 2006/033867; TIC853 toxins of U.S. Pat. No. 8,513,494, AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020 and AXMI-021 of WO 2006/083891; AXMI-010 of WO 2005/038032; AXMI-003 of WO 2005/021585; AXMI-008 of US Patent Application Publication Number 2004/0250311; AXMI-006 of US Patent Application Publication Number 2004/0216186; AXMI-007 of US Patent Application Publication Number 2004/0210965; AXMI-009 of US Patent Application Number 2004/0210964; AXMI-014 of US Patent Application Publication Number 2004/0197917; AXMI-004 of US Patent Application Publication Number 2004/0197916; AXMI-028 and AXMI-029 of WO 2006/119457; AXMI-007, AXMI-008, AXMI-0080r12, AXMI-009, AXMI-014 and AXMI-004 of WO 2004/074462; AXMI-150 of U.S. Pat. No. 8,084,416; AXMI-205 of US Patent Application Publication Number 2011/0023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063 and AXMI-064 of US Patent Application Publication Number 2011/0263488; AXMI-R1 and related proteins of US Patent Application Publication Number 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230 and AXMI231 of WO 2011/103247; AXMI-115, AXMI-113, AXMI-005, AXMI-163 and AXMI-184 of U.S. Pat. No. 8,334,431; AXMI-001, AXMI-002, AXMI-030, AXMI-035 and AXMI-045 of US Patent Application Publication Number 2010/0298211; AXMI-066 and AXMI-076 of US Patent Application Publication Number 2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US Patent Application Publication Number 2010/0005543, cry proteins such as Cry1A and Cry3A having modified proteolytic sites of U.S. Pat. No. 8,319,019; a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to plants expressing Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database, which can be accessed on the world-wide web using the "www" prefix).

The primary structure of a pesticidal polypeptide can be used in its native form or modified in order to introduce amino acid residues (either through addition or substitution) that contribute to or are suspected of contributing to the pesticidal activity of at least one pesticidal polypeptide. Functional data and results from structure-function analyses can be consulted to identify sequences and/or amino acid residues that contribute to pesticidal activity that should be retained or introduced into the candidate polypeptide sequence. Those residues that contribute to or are suspected of contributing to pesticidal activity include those residues that enhance efficacy or those that dictate pesticidal specificity, including those residues that narrow or broaden the range of pests of pesticidal proteins.

For example, the aromaticity of the tyrosine and phenylalanine residues at position 249 and 264, respectively, in helix 7 of the Bt Cry4Ba toxin has been found to be important for toxicity (Tiewsiri and Angsuthanasombat (2007) *J Biochem Mol Biol* 40:163-171). Thus, in those embodiments wherein the candidate polypeptide is homologous with the Bt Cry4Ba toxin, the residues at the positions corresponding to positions 249 and 264 of Cry4Ba should be maintained if they are aromatic or modified if they are non-aromatic.

Further, additional mutations can be introduced into pesticidal polypeptide sequence to improve the pesticidal activity. For example, as described in U.S. Pat. Nos. 7,462,760 and 7,105,332 (each of which are herein incorporated by reference in its entirety), mutations can be introduced into the candidate polypeptide sequence to destroy proteolytic sites to protect the polypeptide from degradative digestion, for example, by plant proteases. As a further example, the toxicity of Bt Cry proteins can be improved by introducing at least one more protease-sensitive site (e.g., trypsin cleavage site) into the region located between alpha helices 3 and 4 of domain 1 of the endotoxin protein (see U.S. Patent Application Publication No. US2004/0091505, which is herein incorporated by reference in its entirety). As another non-limiting example, a protease-sensitive site that is readily cleaved by insect chymotrypsin, e.g., a chymotrypsin found in the bertha armyworm or the corn earworm (Hegedus et al. (2003) *Arch. Insect Biochem. Physiol.* 53: 30-47; and Lenz et al. (1991) *Arch. Insect Biochem. Physiol.* 16: 201-212), may be added to the candidate polypeptide sequence to provide improved toxicity to the polypeptide.

In certain embodiments of the invention, the Cry protein comprises the amino acid sequence set forth in SEQ ID NO: 8, 10, 12 or 14 or fragment or variant thereof. Any nucleotide sequence encoding the amino acid sequence set forth in 8, 10, 12 or 14 or fragment or variant thereof, can be used in the methods and compositions of the present invention including, but not limited to the nucleotides sequences encoding SEQ ID NOS: 8, 10, 12, and 14 which are set forth in SEQ ID NOS: 7, 9, 11, and 13, respectively. In some embodiments of the invention, the nucleotide sequences of the invention will be optimized for expression in a host organism or cell of interest, particularly a plant, more particularly a crop plant, most particularly a maize plant.

Methods of measuring pesticidal activity by insect bioassays are well known in the art. See, e.g., Brooke et al. (2001) *Bull. Entomol. Res.* 91:265-272; Chen et al. (2007) *Proc. Natl. Acad. Sci. USA* 104:13901-13906; Crespo et al. (2008) *Appl. Environ. Microb.* 74:130-135; Khambay et al. (2003) *Pest Manag. Sci.* 59:174-182; Liu & Dean (2006) *Protein Eng. Des. Sel.* 19:107-111; Marrone et al. (1985) *J. Econ. Entomol.* 78:290-293; Robertson et al., *Pesticide Bioassays with Arthropods* (2$^{nd}$ ed., CRC Press 2007); Scott & McKibben (1976) *J. Econ. Entomol.* 71:343-344; Strickman (1985) *Bull. Environ. Contam. Toxicol.* 35:133-142; and Verma et al. (1982) *Water Res.* 16 525-529; as well as U.S. Pat. No. 6,268,181. Examples of insect bioassays include, but are not limited to, pest mortality, pest weight loss, pest repellency, pest attraction, and other behavioral and physical changes of the pest after feeding and exposure to a pesticide or pesticidal polypeptide for an appropriate length of time. General methods include addition of the pesticide, pesticidal polypeptide or an organism having the pesticidal polypeptide to the diet source in an enclosed container. See, e.g., U.S. Pat. Nos. 6,339,144 and 6,570,005.

Further, a nucleic acid encoding the novel chimeric pesticidal polypeptide can be derived from the amino acid sequence and can be generated using any method known in the art. Therefore, novel isolated pesticidal polypeptides and isolated nucleic acid molecules encoding the same are provided. An "isolated" or "purified" polynucleotide or protein or biologically active fragment thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5% or 1% (by dry weight) of contaminating protein. When the protein of the invention or biologically active fragment thereof is recombinantly produced, optimally culture medium represents less than about 30%, 20%, 10%, 5% or 1% (by dry weight) of chemical precursors or non-protein-of-interest chemicals.

Further provided are novel chimeric pesticidal polypeptides comprising fragments and variants of a solubility-enhancing polypeptide and/or pesticidal protein as well as nucleic acid molecules encoding such novel chimeric pesticidal polypeptides. Fragments and variants of the novel chimeric pesticidal polypeptides and chimeric pesticidal polypeptide-encoding nucleic acid molecules are also provided. By "fragment" is intended a portion of the polynucleotide or a portion of the amino acid sequence and hence protein encoded thereby. Fragments of a polynucleotide may encode protein fragments that retain solubility-enhancing activity and/or pesticidal activity. Alternatively, fragments of a polynucleotide that are useful as hybridization probes generally do not encode fragment proteins retaining a solubility-enhancing and/or pesticidal activity. Thus, fragments of a nucleotide sequence may range from at least about 20 nucleotides, about 50 nucleotides, about 100 nucleotides, and up to the full-length polynucleotide encoding the novel chimeric pesticidal polypeptides.

A fragment of a pesticide-encoding polynucleotide that encodes a biologically active fragment of a solubility-enhancing polypeptide or pesticidal protein will encode at least 15, 25, 30, 50, 100, 150, 200, 250, 300, 400, 500, 600, 700, 800, 900, 1000 or 1,100 contiguous amino acids or up to the total number of amino acids present in a chimeric pesticidal polypeptide, a solubility-enhancing polypeptide or a pesticidal protein of the invention. Fragments of a chimeric pesticidal polypeptide, solubility-enhancing polypeptide or a pesticidal protein that are useful as hybridization probes or PCR primers generally need not encode a biologically active fragment of a chimeric pesticidal polypeptide, a solubility-enhancing polypeptide or a pesticidal protein.

Thus, a fragment of a chimeric pesticidal polypeptide, a solubility-enhancing polypeptide or a pesticidal protein may encode a biologically active fragment of a pesticidal protein or it may be a fragment that can be used as a hybridization probe or PCR primer using methods well known in the art and disclosed elsewhere herein. A biologically active fragment of a pesticidal protein can be prepared by isolating a portion of one of the pesticide-encoding polynucleotides, expressing the encoded portion of the pesticidal protein (e.g., by recombinant expression in vitro), and assessing the activity of the encoded portion of the pesticidal protein. Polynucleotides that are fragments of a chimeric pesticidal polypeptide, a solubility-enhancing polypeptide or a pesticidal protein sequence comprise at least 16, 20, 50, 75, 100, 150, 200, 250, 300, 350, 400, 450, 500, 550, 600, 650, 700, 800, 900, 1000, 1100, 1200, 1300, 1400, 1500, 1600, 1700, 1800, 1900, 2000, 2500 or 3000 contiguous nucleotides or up to the number of nucleotides present in a full-length pesticide-encoding polynucleotide discovered using the methods disclosed herein.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the chimeric pesticidal polypeptide, solubility-enhancing polypeptides or pesticidal proteins of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a chimeric pesticidal polypeptide, a solubility-enhancing polypeptide or a pesticidal protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 2 is disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein, that is, pesticidal activity as described herein. Such variants may result from, for example, genetic polymorphism or from human manipulation. Biologically active variants of a chimeric pesticidal polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2 or even 1 amino acid residue.

The novel chimeric pesticidal polypeptide made using the presently disclosed methods may be altered in various ways including amino acid substitutions, deletions, truncations, and insertions to the solubility-enhancing polypeptide and/or the pesticidal polypeptide portion of the chimeric pesticidal polypeptide. Methods for such manipulations are generally known in the art. For example, amino acid sequence variants and fragments of the chimeric pesticidal polypeptides, pesticidal polypeptides, and solubility-enhancing polypeptide s can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

The deletions, insertions, and substitutions of the novel chimeric pesticidal polypeptide sequences, pesticidal polypeptide sequences and solubility-enhancing polypeptide sequences encompassed herein are not expected to produce radical changes in the characteristics of the protein. However, when it is difficult to predict the exact effect of the substitution, deletion or insertion in advance of doing so, one skilled in the art will appreciate that the effect will be evaluated by routine screening assays. That is, the pesticidal activity can be evaluated using an insect feeding bioassays as described elsewhere herein. Preferably, the biologically activity of a solubility-enhancing polypeptide or fragment or variant thereof is evaluated by operably linking the solubility-enhancing polypeptide, fragment or variant to a pesticidal polypeptide and assaying the pesticidal activity of the resulting chimeric pesticidal polypeptide using the methods disclosed herein or otherwise known in the art. The pesticidal activity of the chimeric pesticidal polypeptide can be compared to the pesticidal activity of the pesticidal peptide (i.e., without the solubility-enhancing polypeptide, fragment or variant) to determine if the solubility-enhancing polypeptide, fragment or variant increases the insecticidal activity the chimeric pesticidal polypeptide. Preferably, in any insect feeding assays in which the chimeric pesticidal polypeptide its corresponding pesticidal polypeptide, the amount of the respective polypeptides that are fed to the insects will be adjusted to take into the account the large molecular weight of the chimeric pesticidal polypeptide such that pesticidal activity comparisons will effectively be made on a per molecule or per mole basis. Furthermore, it is recognized that insecticidal activity of chimeric pesticidal polypeptides with different solubility-enhancing polypeptides or fragments or variants of a solubility-enhancing polypeptide can also evaluated and compared to one another in a like manner and preferably with adjustments for any differences in molecular weights between the chimeric pesticidal polypeptides that are being compared.

Variant polynucleotides and proteins also encompass sequences and proteins derived from a mutagenic and recombinogenic procedure such as DNA shuffling. With such a procedure, one or more different pesticide-coding sequences can be manipulated to create a new pesticidal polypeptide possessing the desired properties and these new pesticidal proteins can be used in the methods disclosed herein to make chimeric pesticidal polypeptides. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score =100, wordlength =12, to obtain nucleotide sequences homologous to a nucleotide sequence encoding a protein of the invention. BLAST protein searches can be performed with the BLASTX program, score =50, wordlength =3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See ncbi.nlm.nih.gov, which can be accessed on the world-wide web using the "www" prefix. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments or other oligonucleotides, and may be labeled with a detectable group such as $^{32}P$ or any other detectable marker. Thus, for example, probes for hybridization can be made by labeling synthetic oligonucleotides based on the babyboom polynucleotide. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire pesticide-encoding polynucleotide or one or more portions thereof, may be used as a probe capable of specifically hybridizing to corresponding pesticide-encoding polynucleotides and messenger RNAs. To achieve specific hybridization under a variety of conditions, such probes include sequences that are unique among pesticide-encoding polynucleotide sequences and are optimally at least about 10 nucleotides in length, and most optimally at least about 20 nucleotides in length. Such probes may be used to amplify corresponding pesticide-encoding polynucleotides from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$, can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

Nucleic acids encoding the novel chimeric pesticidal polypeptides can be used in DNA constructs for expression in various hosts, including plants. Thus, expression cassettes comprising the novel chimeric pesticidal polypeptide-encoding nucleic acids for expression in the organism of interest are provided. The cassette will include 5' and 3' regulatory sequences operably linked to a novel chimeric pesticidal polypeptide-encoding polynucleotide. "Operably linked" is intended to mean a functional linkage between two or more elements. For example, an operable linkage between a polynucleotide of interest and a regulatory sequence (i.e., a promoter) is a functional link that allows for expression of the polynucleotide of interest. In the case of fusion proteins or fusion polypeptides, an operable linkage between, for example, a first amino amino sequence of interest and a second amino acid of interest results in a single amino acid sequence, which comprises both the first and second amino acid sequences, and wherein the C-terminal amino acid the first amino amino sequence is covalently attached to the N-terminal amino acid of the second amino acid sequence by a peptide bond. Operably linked elements may be contiguous or non-contiguous. The cassette may additionally contain at least one additional polynucleotide of interest to be cotransformed into the organism. Alternatively, the additional polynucleotide(s) of interest can be provided on multiple expression cassettes. Such an expression cassette is provided with a plurality of restriction sites and/or recombination sites for insertion of the pesticide-encoding polynucleotide to be under the transcriptional regulation of the regulatory regions. The expression cassette may additionally contain selectable marker genes.

The chimeric pesticidal polypeptides of the present invention comprise an amino acid sequence of a solubility-enhancing polypeptide operably linked to an amino acid sequence of a Cry endotoxin. It is recognized that in such an operable linkage, the amino acid sequence of the solubility-enhancing polypeptide can be contiguous to the amino acid sequence of the Cry endotoxin or can be separated by an intervening linker or other amino acid sequence. Likewise, the chimeric pesticidal polypeptide-encoding nucleic acid molecules of the present invention comprise a nucleotide sequence encoding a solubility-enhancing polypeptide operably linked to a nucleotide sequence encoding a Cry endotoxin. It is further recognized that in such an operable linkage, the nucleotide sequence encoding the solubility-enhancing polypeptide can be contiguous to the nucleotide sequence encoding the Cry endotoxin or can be separated by an intervening linker-encoding nucleotide sequence or other nucleotide sequence.

The expression cassette will include in the 5'-3' direction of transcription, a transcriptional and translational initiation region (i.e., a promoter), a novel pesticide-encoding polynucleotide, and a transcriptional and translational termination region (i.e., termination region) functional in the organism to which the expression cassette is introduced. The regulatory regions (i.e., promoters, transcriptional regulatory regions, and translational termination regions) and/or the pesticide-encoding polynucleotide may be native/analogous to the host cell or to each other. Alternatively, the regulatory regions and/or the pesticide-encoding polynucleotide may be heterologous to the host cell or to each other. As used herein, "heterologous" in reference to a sequence is a sequence that originates from a foreign species or, if from the same species, is substantially modified from its native form in composition and/or genomic locus by deliberate human intervention. For example, a promoter operably linked to a heterologous polynucleotide is from a species different from the species from which the polynucleotide was derived or, if from the same/analogous species, one or both are substantially modified from their original form and/or genomic locus or the promoter is not the native promoter for the operably linked polynucleotide.

The termination region may be native with the transcriptional initiation region, may be native with the operably linked pesticidal polynucleotide of interest, may be native with the plant host or may be derived from another source (i.e., foreign or heterologous) to the promoter, the pesticidal polynucleotide of interest, the plant host or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

The chimeric pesticidal polypeptide-encoding nucleic acid molecules, expression cassettes comprising the same or the chimeric pesticidal polypeptides can be introduced into an organism or host cell, particularly a non-human host cell. Host cells may be prokaryotic cells such as *E. coli* or eukaryotic cells such as yeast, insect, amphibian or mammalian cells. In some examples, host cells are monocotyledonous or dicotyledonous plant cells.

The nucleic acid encoding the novel chimeric pesticidal polypeptides can be introduced into microorganisms that multiply on plants (epiphytes) to deliver chimeric pesticidal polypeptides to potential target pests. Alternatively, the chimeric pesticidal polypeptides can be directly introduced into such microorganisms. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Nucleic acids encoding the pesticidal proteins of the invention or the chimeric pesticidal polypeptides can be introduced into a root-colonizing *Bacillus cereus* by standard methods known in the art.

Nucleic acids encoding chimeric pesticidal polypeptides can be introduced, for example, into the root-colonizing *Bacillus* by means of electrotransformation. Specifically, nucleic acids encoding the pesticidal proteins can be cloned into a shuttle vector, for example, pHT3101 (Lerecius et al. (1989) *FEMS Microbiol. Letts.* 60: 211-218. The shuttle vector pHT3101 containing the coding sequence for the particular chimeric pesticidal polypeptide-encoding nucleic acid can, for example, be transformed into the root-colonizing *Bacillus* by means of electroporation (Lerecius et al. (1989) *FEMS Microbiol. Letts.* 60: 211-218).

Expression systems can be designed so that chimeric pesticidal polypeptides are secreted outside the cytoplasm of gram-negative bacteria, such as *E. coli*, for example. Advantages of having chimeric pesticidal polypeptides secreted are: (1) avoidance of potential cytotoxic effects of the chimeric pesticidal polypeptides expressed; and (2) improvement in the efficiency of purification of the chimeric pesticidal polypeptides, including, but not limited to, increased efficiency in the recovery and purification of the protein per volume cell broth and decreased time and/or costs of recovery and purification per unit protein.

Chimeric pesticidal polypeptides can be made to be secreted in *E. coli*, for example, by fusing an appropriate *E. coli* signal peptide to the amino-terminal end of the pesticidal protein. Signal peptides recognized by *E. coli* can be found in proteins already known to be secreted in *E. coli*, for example the OmpA protein (Ghrayeb et al. (1984) *EMBO J*, 3:2437-2442). OmpA is a major protein of the *E. coli* outer membrane, and thus its signal peptide is thought to be efficient in the translocation process. Also, the OmpA signal peptide does not need to be modified before processing as may be the case for other signal peptides, for example lipoprotein signal peptide (Duffaud et al. (1987) *Meth. Enzymol.* 153: 492).

Chimeric pesticidal polypeptides of the invention can be fermented in a bacterial host and the resulting bacteria processed and used as a microbial spray in the same manner that *Bacillus thuringiensis* strains have been used as insecticidal sprays. In the case of a chimeric pesticidal polypeptide(s) that is secreted from *Bacillus*, the secretion signal is removed or mutated using procedures known in the art. Such mutations and/or deletions prevent secretion of the chimeric pesticidal polypeptide(s) into the growth medium during the fermentation process. The chimeric pesticidal polypeptides are retained within the cell, and the cells are then processed to yield the encapsulated chimeric pesticidal polypeptides. Any suitable microorganism can be used for this purpose. *Pseudomonas* has been used to express *Bacillus thuringiensis* endotoxins as encapsulated proteins and the resulting cells processed and sprayed as an insecticide (Gaertner et al. (1993), in: *Advanced Engineered Pesticides*, ed. Kim).

Alternatively, the chimeric pesticidal polypeptides are produced by introducing a heterologous nucleic acid encoding the chimeric pesticidal polypeptide into a cellular host. Expression of the heterologous nucleic acid results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated chimeric pesticidal polypeptides may then be formulated in accordance with conventional techniques for application to the environment hosting a target pest, e.g., soil, water, and foliage of plants. See, for example EPA 0192319, and the references cited therein.

The novel chimeric pesticidal polypeptide-encoding polynucleotides and chimeric pesticidal polypeptides can be introduced into plant cells or plants to produce a transgenic plant that is resistant to pests that are susceptible to the chimeric pesticidal polypeptide.

The novel chimeric pesticidal polypeptide-encoding polynucleotides can be combined with constitutive, tissue-preferred or other promoters for expression in plants. The promoters can be selected based on the desired outcome.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced chimeric pesticidal polypeptide expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed roIC and roID root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and roIB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed; herein incorporated by reference.

Where low level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon, pp.* 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Bairn et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

In one embodiment, the polynucleotide of interest is targeted to the chloroplast for expression. In this manner, where the polynucleotide of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Chloroplast targeting sequences are known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6):789-810); tryptophan synthase (Zhao et al. (1995) *J. Biol. Chem.* 270(11):6081-6087); plastocyanin (Lawrence et al. (1997) *J. Biol. Chem.* 272 (33):20357-20363); chorismate synthase (Schmidt et al. (1993) *J. Biol. Chem.* 268(36):27447-27457); and the light harvesting chlorophyll a/b binding protein (LHBP) (Lamppa et al. (1988) *J. Biol. Chem.* 263:14996-14999). See also Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The polynucleotides of interest to be targeted to the chloroplast may be optimized for expression in the chloroplast to account for differences in codon usage between the plant nucleus and this organelle. In this manner, the polynucleotide of interest may be synthesized using chloroplast-preferred codons. See, for example, U.S. Pat. No. 5,380,831, herein incorporated by reference.

The methods of the invention involve introducing a polypeptide or polynucleotide into a plant or other organism. "Introducing" is intended to mean presenting to the organism the polynucleotide or polypeptide in such a manner that the sequence gains access to the interior of a cell of the organism. The methods of the invention do not depend on a particular method for introducing a sequence into an organism, only that the polynucleotide or polypeptides gains access to the interior of at least one cell of the organism. Methods for introducing polynucleotides or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Led transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the chimeric pesticidal polypeptide-encoding sequences of the invention can be provided to a plant using a variety of transient transformation methods. Such transient transformation methods include, but are not limited to, the introduction of the pesticidal protein or variants and fragments thereof directly into the plant or the introduction of the a pesticide-encoding transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the pesticide-encoding polynucleotide can be transiently transformed into the plant using techniques known in the art. Such techniques include a viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine.

In other embodiments, the novel chimeric pesticidal polypeptide-encoding polynucleotide may be introduced into plants by contacting plants with a virus or viral nucleic acids. Generally, such methods involve incorporating a nucleotide construct within a viral DNA or RNA molecule. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

As used herein, the term plant also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), *sorghum* (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), *citrus* trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), *hydrangea* (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*.

Conifers that may be employed in practicing the present invention include, for example, pines such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, *sorghum*, wheat, millet, tobacco, etc.). In other embodiments, corn and soybean and sugarcane plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, *sorghum*, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The present invention also provides a pesticidal composition comprising an effective amount of at least one chimeric pesticidal polypeptide of the invention to reduce pest damage to the plant and methods of protecting a plant from a pest involving providing to the plant or to the vicinity of the plant an effective amount of a pesticidal composition. By "effective amount" and "effective concentration" is intended an amount and concentration, respectively, that is sufficient to kill or inhibit the growth of a plant pest. Methods for determining an "effective amount" and "effective concentration" are known to those of ordinary skill in art and include, for example, assays involving placing varying amounts of concentrations of the active ingredient (e.g., a chimeric pesticidal polypeptide) in contact with and/or in the vicinity of a pest and monitoring the survival and/or growth of the pest over time.

As described above, the effective amount of a chimeric pesticidal polypeptide can vary depending on the formulation and method in which the formulation is applied to the plant or plant environment. As such, bacteria can be transformed with a nucleotide sequence encoding a chimeric pesticidal polypeptide and can be used in the pesticidal compositions as described herein. Thus, the pesticidal composition can be an organism that is transformed to express a chimeric pesticidal polypeptide. Alternatively, a chimeric pesticidal polypeptide can be purified from the bacteria as described above. In some embodiments, the pesticidal composition or pesticidal formulation can include other agricultural protectants, as described above. As used herein, the term "pesticidal composition" and "pesticidial formulation" are equivalent terms that have the same meaning unless indicated otherwise or apparent from the context as used.

As described above, the effective amount of a chimeric pesticidal polypeptide can vary depending on the formulation and method in which the formulation is applied to the plant or plant environment. As such, bacteria can be transformed with a nucleotide sequence encoding a chimeric pesticidal polypeptide and can be used in the pesticidal compositions as described herein. Thus, the pesticidal composition can be an organism that is transformed to express a chimeric pesticidal polypeptide. Alternatively, the chimeric pesticidal polypeptide can be purified from the bacteria as described above. In some embodiments, the pesticidal compositions or pesticidal formulation can include other agricultural protectants, as described above.

As described above, the pesticidal composition can be, for example, a dust, emulsion, solid (e.g., particle or pellets) or liquid.

The pesticidal composition can be provided to the plant by applying the pesticidal composition directly to the environment of the plant or to the vicinity of the plant such as, for example, in the soil or other growth medium surrounding the plant to protect the plant from pest attacks. For example, the pesticidal composition can be applied directly to the plant by atomizing, broadcasting, coating or pouring, dusting spraying, scattering, soil drenching, sprinkling or seed coating at the time when the pest such as, for example, an insect pest has begun to appear on the plant or before the appearance of insect pests as a protective measure.

Alternatively, the pesticidal composition can be introduced into irrigation water and then applied to the plant during watering. It is preferred to obtain good control of pest in the early stages of plant growth as this is the time when the plant can be most severely damaged. To maintain protection as plants grow and to obtain the greatest protection of large plants, repeated applications of the pesticidal composition can be beneficial.

The number of applications and the rate of application depend on the intensity of infestation by the corresponding pest. When the pesticidal composition not only includes the chimeric pesticidal polypeptide and/or a chimeric pesticidal polypeptide-expressing bacteria, but also includes another agricultural protectant, the formulation can be applied to the crop area or plant to be treated simultaneously or in succession (i.e., sequentially).

The pesticidal composition will reduce pest-related damage by at least about 5% to about 50%, at least about 10% to about 60%, at least about 30% to about 70%, at least about 40% to about 80% or at least about 50% to about 90% or greater. Hence, the methods can be utilized to protect plants from pests. Protection may vary from a slight decrease in plant damage caused by the pest (e.g., partial inhibition) to total decrease such that the plant is unaffected by the presence of the pest.

The present invention therefore provides methods of protecting plants, plant parts and plant host cells by providing a pesticidal composition comprising a chimeric pesticidal polypeptide.

In certain embodiments the polynucleotides of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981,722), and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the present invention can also be stacked with traits desirable for disease or herbicide resistance (e.g., fumonisin detoxification genes, U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs,* ed. Applewhite (American Oil Chemists Society, Champaign, Ill.), pp. 497-502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene); glyphosate (e.g., the EPSPS gene and the GAT gene; see, for example, U.S. Publication No. 20040082770 and WO 03/092360); or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, when an amount, concentration or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the presently disclosed subject matter be limited to the specific values recited when defining a range.

The following examples are offered by way of illustration and not by way of limitation.

EXAMPLE 1

Enhancement of the Insecticidal Activity of Cry Proteins Against Western Corn Rootworms and Black Cutworms when Fused to MBP A computer-designed and artificially synthesized Cry3Aa-type protein called IP3-1 (SEQ ID NO: 8), a truncated RX002 protein (SEQ ID NO: 12) cloned from a Bt strain, a shuffled Cry8Bb-type protein called 2A-12 (SEQ ID NO: 10), and a truncated native Cry1Bd protein called 4c6 (SEQ ID NO: 14) were expressed in *E. coli* BL21 as fusion proteins comprising an operably linked MBP. The amino acid sequences of the MBP-IP3-1, MBP-RX002, MBP-2A-12, and MBP-4c6 fusion proteins are set forth in SEQ ID NOS: 21, 23, 25, and 27, respectively. Nucleotide sequences encoding the MBP-IP3-1, MBP-RX002, MBP-2A-12, and MBP-4c6 fusion proteins are set forth in SEQ ID NOS: 20, 22, 24, and 26, respectively.

To express MBP with these Bt Cry proteins, corresponding genes were cloned in an NEB pMAL vector and the proteins were purified using amylose resin following the manufacturer's recommended method (New England Biolabs, Inc., Ipswich, Mass., USA; Catalog No. E8021 L). The target protein eluted from amylase resin was concentrated in Amicon Centricon concentrator (10 kDa cutoff). The final fusion proteins were dissolved in 25 mM HEPES-NaOH buffer pH8 at a concentration around 2 mg/ml. The protein concentration was determined by SDS-PAGE using bovine serum albumin as the reference. The pMAL vector has a protease site specific to Factor Xa that cleaves MBP and the linker off the Cry protein. All Cry proteins included in this application were resistant to Factor Xa. The protease digestion was carried out in the HEPES buffer at 1:25 protease and substrate ration at 20° C. for 16 hr. The digestion leading to the complete MBP removal was confirmed by SDS-PAGE.

MBP fusion and MBP free Cry proteins were diluted in 25 mM HEPES-NaOH buffer pH 8 and 10 μL of diluted samples were mixed with 40 μL of molten artificial insect diet made with low temperature melting agarose. The diet mixture was then placed in each well of a 96-well micro-titer plate and allowed to feed with neonate insect larvae. After 4 days at 27° C., the responses of insects towards the Cry proteins were scored using a 0-3 numerical scoring system based on the size and mortality. If no response or normal growth was seen, Score 0 was given. When the growth was somewhat retarded without any mortality, it was Score 1. Score 2 meant partial death (multiple insects were used in each well) and strong growth inhibition. Score 3 indicated the complete mortality. Each treatment was repeated 6 times for possible highest score of 18 (3×6). In this scoring system, Score 9 with 6 repeats of one treatment means the 50% response (9 out of 18) of the treatment and called ILC50 (growth Inhibition and Lethal Concentration for 50% response). The results of these assays are shown in Tables 3 and 4.

The results shown in Tables 3 and 4 with four different Cry proteins demonstrate that MBP-Cry fusion proteins have significantly increased insecticidal activity against both Coleopteran (Western Corn Rootworm) and Lepidopteran (Black Cutworm) insect species, when compared to the insecticidial activity of their respective free Cry proteins. These results further demonstrate the general applicability of the methods of the present invention to enhancing the insecticidal activity of Cry proteins. Table 3 shows ILC50 (based on the size or weight of the Cry protein portion) values for insecticidal activity against Western Corn Rootworm of MBP-Cry Fusion Proteins and Free Cry Proteins.

TABLE 3

| IP3-1 | | RX002 | | 2A-12 | |
|---|---|---|---|---|---|
| MBP-fusion | free Cry | MBP-fusion | free Cry | MBP-fusion | free Cry |
| 7 ppm | 103 ppm | 89 ppm | No activity* | 32 ppm | 152 ppm |

*Only an 11% response was observed at 2480 ppm.

Table 4 shows the ILC50 values for insecticidal activity against Black Cutworm of a MBP-4c6 Cry Fusion Protein and Free 4c6 Cry Protein.

TABLE 4

| MBP-4c6 fusion | free 4c6 |
|---|---|
| 75 ppm | 148 ppm |

EXAMPLE 2

MBP-Cry Fusion Protein with Increased Activity Against WCRW

A new vector, pMAL-SA (SEQ ID NO: 19), was constructed for making MBP-Cry fusion proteins. This vector is based on NEB pMAL vector. It has the cry gene cloning site delineated with SphI and BamHI recognition sequences at the end of MBP and a specially designed linker called "SA" linker between MBP and the Cry cloning site.

In order to clone a Bt cry gene, the cry coding region is amplified by PCR using appropriate forward and reverse primers. In the forward primer, there is an SphI site over the ATG translation initiation site. In the reverse primer, there is a stop codon at the end of the cry gene coding region and a BamHI site.

A computer-designed cry3Aa sequence, IP3-1, was synthesized and used as the PCR template. The IP3-1 nucleotide sequence is set forth in SEQ ID NO: 7. This IP3-1 gene was cloned in pMAL-SA as described above to produce a plasmid that contains MBP, the SA linker and IP3-1 coding region (SEQ ID NO: 1). The second amino acid residue of IP3-1 was mutated back to Asn from His to produce the MBP-SA-IP3-1 nucleotide sequence set forth in SEQ ID NO: 2.

The MBP-SA-IP3-1 fusion protein was expressed in *E. coli* BL21 and purified by amylose resin affinity chromatography according to the method described in Example 1. The column eluate was concentrated in Amicon Centricon and its buffer was exchanged to 25 mM HEPES-NaOH buffer pH 8. The fusion protein was digested with trypsin at 1:25 trypsin-substrate ratio at 37° C. for 1 hr. Trypsin cleaves the protein at the end of the linker to liberate the Cry protein from MBP and the SA linker. IP3-1 was resistant to trypsin under this digestion condition. The digestion was confirmed with SDS-PAGE. Both the fusion and MBP-free IP3-1 proteins were assayed against WCRW. Table 5 shows ILC50 values for insecticidal activity against Western Corn Rootworm of a MBP-SA-IP3-1 and MBP-free IP3-1. The assay results in Table 5 demonstrate that there is a significant enhancement of WCRW activity when IP3-1 is operable linked to MBP-SA (i.e., MBP-SA-IP3-1), when compared to the insecticidal activity of MBP-free IP3-1 against WCRW.

TABLE 5

| Protein | ICL50 |
|---|---|
| MBP-SA-IP3-1 | 6 ppm |
| MBP-free IP3-1 | 269 ppm |

EXAMPLE 3

Enhancement of Cry3Aa Protein Activity when Fused to NusA and Trx

A computer-designed and artificially synthesized cry3Aa-type gene called IP3-1 was cloned in pET-43.1 EK/LIC for NusA fusion and pET-32 for TrxA fusion by following the manufacturer's directions (EMD Biosciences, Madison, Wis., USA). These vectors were used to express NusA-IP3-1 and TrxA-IP3-1 fusion proteins. The amino acid sequences of the NusA-IP3-1 and TrxA-IP3-1 fusion proteins are set forth in SEQ ID NOS: 16 and 18, respectively. Nucleotide sequences encoding the NusA-IP3-1 and TrxA-IP3-1 fusion proteins are set forth in SEQ ID NOS: 15 and 17, respectively. The amino acid sequence of IP3-1 is set forth in SEQ ID NO: 8. A nucleotide sequence encoding IP3-1 is set forth in SEQ ID NO: 7.

The fusion proteins were purified by affinity chromatography using Ni-NTA agarose (Qiagen Inc., Valencia, Calif., USA) according to the manufacturer's directions. The Cry3Aa protein was then digested away from the tags including NusA, TrxA, 6×His etc. with enterokinase and the insecticidal activity of the free Cry3A protein was compared with its NusA and TrxA fusion proteins. The insect assay was conducted using WCRW as described above. Table 6 shows the ILC50 values for insecticidal activity against Western Corn Rootworm of a MBP-SA-IP3-1 and MBP-free IP3-1 protein. The IP3-1 protein sample was produced from the NusA-Cry3Aa fusion by enterokinase digestion. As demonstrated in the results in Table 6, both the NusA-IP3-1- and TrxA-IP3-1-fusion proteins, which comprise a solubility-enhancing polypeptide and a Cry3A protein (IP3-1), have an increased insecticidal activity against WCRW as evidenced by the significantly lower ICL50 values, when compared to insecticidal activity of free IP3-1.

TABLE 6

| Protein | ICL50 |
|---|---|
| NusA-IP3-1-fusion | 26 ppm |
| TrxA-IP3-1-fusion | 31 ppm |
| Tag free IP3-1 | 554 ppm |

EXAMPLE 4

Generation of a MBP-SA-RX002 Transformation Construct

The maltose-binding protein (MBP-SA) (SEQ ID NO: 4) was fused to the N-terminus of RX002 (SEQ ID NO:11) in a synthetic gene designed for this invention (SEQ ID NO:32 encoding SEQ ID NO:33). The gene was cloned as a BamHI-StuI fragment into a Gateway entry vector containing a plant expression cassette with the BSV(AY) TR PROMOTER-ADH1 INTRON1 sequence and the potato PIN II terminator sequence. The resulting plant expression cassette contains the following components operatively linked together in this order; BSV (AY) TR PRO-ADH1-INTRON1, the MBP-SA-RX002 gene, and the PIN II terminator. The expression cassette is flanked by Gateway attL3 and attL4 recombination sites and this entry vector was used to transfer the expression cassette into an attR3 and attR4 containing binary destination transformation vector. The final transformation vector contains the MBP-SA-RX002 expression cassette upstream of a cassette containing the maize Ubiquitin) promoter-5'UTR-Ubiquitin intron) controlling expression of a PAT selectable marker gene with the 35S terminator sequence.

EXAMPLE 5

*Agrobacterium*-Mediated Transformation of Maize and Regeneration of Transgenic Plants For *Agrobacterium*-mediated transformation of maize with a promoter sequence of the invention, the method of Zhao was employed (U.S. Pat. No. 5,981,840, and PCT patent publication WO98/32326; the contents of which are hereby incorporated by reference). Briefly, immature embryos were isolated from maize and the embryos contacted with a suspension of *Agrobacterium* under conditions whereby the bacteria were capable of transferring the promoter sequence of the invention to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following the co-cultivation period and an optional "resting" step was performed. In this resting step, the embryos were incubated in the presence of at least one antibiotic known to inhibit the growth of *Agrobacterium* without the addition of a selective agent for plant transformants (step 3: resting step). The immature embryos were cultured on solid medium with antibiotic, but without a selecting agent, for elimination of *Agrobacterium* and for a resting phase for the infected cells. Next, inoculated embryos were cultured on medium containing a selective agent and growing transformed callus was recovered (step 4: the selection step). The immature embryos were cultured on solid medium with a selective agent resulting in the selective growth of transformed cells. The callus was then regenerated into plants (step 5: the regeneration step), and calli grown on selective medium were cultured on solid medium to regenerate the plants.

EXAMPLE 6

Expression of MBP-RX002 Fusion in Transgenic Maize Tissue

Transgenic events derived from the testing vector were evaluated for expression of MBP-RX002 by Western analysis. Leaf and root material for transgenic maize expressing MBP-RX002 were lyophilized then powdered with 5/32 inch BBs (i.e., birdshot) using a Geno/Grinder 2000 homogenizer at 1700 beats per minute for 30 seconds. 80 μL of grinding buffer (1×PBS+0.1% Tween-20+1% 2-mercaptoethanol containing Roche cOmplete protease inhibitor (Roche Applied Science, Indianapolis, Ind., USA; Catalog No. 04693124001; at one tablet per 7 mL) was added to each sample. Pulverization was repeated for an additional 30 seconds, then the samples were sonicated for 5 minutes at room temperature in a VWR 75D sonicator. After centrifugation at 21,000 g/4° C. for 15 minutes, supernatants were collected. Protein concentrations were determined from the supernatants using Thermo Scientific Coomassie Plus Kit (23236) and a SpectraMAX 190 spectrophotometer. Samples were normalized for total protein in 21 μL using grinding buffer as diluent. Seven microliters of 4×LDS dye containing 1% 2-mercaptoethanol was added to each sample prior to heating at 80° C. for 10 minutes. Twenty-five microliters of sample was loaded per lane on a NuPAGE Novex 4-12% Bis-Tris midi gel (Invitrogen WB1402BOX) and electrophoresed at 200 V for 1 hour. Protein was transferred to a nitrocellulose membrane using an Invitrogen iBlot with a transfer stack (1B301001). The membrane was blocked for 30 minutes in 1×PBS+0.1% Tween-20+5% powdered milk w/v (blocking buffer), then incubated overnight at 4° C. with rabbit polyclonal antibody against RX002, diluted in blocking buffer at 1:4000. Membrane was washed 4×5 minutes in PBST (1×PBS+0.1% Tween-20), then incubated for 2 hours with goat anti-rabbit HRP conjugated secondary antibody (Pierce 31460; 10 μg/mL working stock) at a 1:5000 dilution in blocking buffer. The membrane was washed 4×5 minutes in PBST and developed using Thermo Super Signal West Dura Extended Duration Substrate (34076). Visualization of hybridization signal was accomplished using a Fujifilm LAS-4000 imaging system.

The results of this analysis are shown in Table 7. Accumulation of MBP-RX002 was detected in 8 of the 10 events sampled for Western analysis in either root or leaf and root tissue. An 118 kD protein band corresponding to the expected size of the MBP-RX002 fusion was observed in both leaf and root or root tissue demonstrating that the fusion can be expressed in planta. In addition to the full length protein, a 75 kD immunoreactive protein band corresponding to the expected size of RX002 was also observed in some events indicating that some proportion of the full-length fusion protein was processed in planta to release RX002.

TABLE 7

| Event No. | Expression in leaf | Expression in root |
|---|---|---|
| Control | − | − |
| 123434603 | − | − |
| 123434607 | +++ | ++++ |
| 123434610 | − | − |
| 123434613 | ++++ | ++++ |
| 123434614 | − | + |
| 123434615 | − | ++ |
| 123434616 | ++++ | ++++ |
| 123434617 | ++++ | ++++ |
| 123434618 | ++++ | ++++ |
| 123434619 | − | +++ |

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of enhancing pesticidal activity of a Cry endotoxin, the method comprising operably linking a first amino acid sequence of maltose binding protein to a second amino acid sequence of a Cry endotoxin comprising an amino acid sequence selected from the group consisting of SEQ ID NOS: 8, 10, 12 and 14; whereby a chimeric pesticidal polypeptide is produced; and wherein the chimeric pesticidal polypeptide comprising the first amino acid sequence operably linked to the second amino acid sequence exhibits enhanced pesticidal activity.

2. The method of claim 1, wherein the maltose binding protein comprises an amino acid sequence selected from the group consisting of SEQ ID NO: 6 and 34.

3. The method of claim 1 or 2, wherein the chimeric pesticidal polypeptide comprises an amino acid sequence selected from the group consisting of the amino acid sequences set forth in SEQ ID NOS: 2, 21, 23, 25, 27 and 33.

* * * * *